(12) United States Patent
Armani et al.

(10) Patent No.: US 9,487,528 B2
(45) Date of Patent: Nov. 8, 2016

(54) COMPOUNDS

(71) Applicant: CHIESI FARMACEUTICI S.p.A., Parma (IT)

(72) Inventors: Elisabetta Armani, Parma (IT); Carmelida Capaldi, Parma (IT); Jonathan Mark Sutton, Harlow (GB); Robert Andrew Heald, Harlow (GB)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 14/731,786

(22) Filed: Jun. 5, 2015

(65) Prior Publication Data

US 2015/0353561 A1    Dec. 10, 2015

(30) Foreign Application Priority Data

Jun. 9, 2014   (EP) ..................................... 14172176

(51) Int. Cl.
*C07D 487/04*   (2006.01)
*A61K 31/519*   (2006.01)

(52) U.S. Cl.
CPC ........... *C07D 487/04* (2013.01); *A61K 31/519* (2013.01)

(58) Field of Classification Search
CPC .................................................. C07D 400/01
See application file for complete search history.

(56) References Cited

U.S. PATENT DOCUMENTS

| | | | |
|---|---|---|---|
| 8,198,288 B2 | 6/2012 | Ray et al. |
| 8,691,826 B2 | 4/2014 | Blench et al. |
| 8,957,082 B2 | 2/2015 | Ray et al. |
| 9,023,855 B2 | 5/2015 | Blench et al. |
| 9,120,802 B2 | 9/2015 | Edwards et al. |
| 2013/0065913 A1 | 3/2013 | Blench et al. |
| 2013/0150380 A1 | 6/2013 | Edwards et al. |
| 2014/0018345 A1 | 1/2014 | Capaldi et al. |
| 2014/0171414 A1 | 6/2014 | Alcaraz et al. |
| 2015/0166548 A1 | 6/2015 | Alcaraz et al. |

FOREIGN PATENT DOCUMENTS

| | | |
|---|---|---|
| WO | 2011/110858 | 9/2011 |
| WO | 2011/110859 | 9/2011 |

OTHER PUBLICATIONS

European Search Report in Application No. 14172176.1 issued Dec. 9, 2014.

*Primary Examiner* — Paul V Ward
(74) *Attorney, Agent, or Firm* — Oblon, McClelland, Maier & Neustadt, L.L.P

(57) ABSTRACT

Compounds of formula (I), described herein, exhibit human neutrophil elastase inhibitory properties, and are useful for the treatment of diseases and conditions in which HNE is implicated.

27 Claims, No Drawings

COMPOUNDS

CROSS REFERENCES TO RELATED APPLICATIONS

This application claims priority to European Patent Application No. 14172176.1, filed on Jun. 9, 2014, which is incorporated herein by reference in its entirety.

BACKGROUND OF THE INVENTION

1. Field of the Invention

The present invention relates to pyrimidinone derivatives which exhibit human neutrophil elastase inhibitory properties. The present invention also relates to the use of such a compound in therapy.

2. Discussion of the Background

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (Bieth, G. In *Regulation of Matrix accumulation*, Mecham, R. P. (Eds), Academic Press, NY, USA 1986, 217-306, which is incorporated herein by reference in its entirety). HNE has long been considered to play an important role in homeostasis through repair and disposal of damaged tissues via degradation of the tissue structural proteins. It is also relevant in the defense against bacterial invasion by means of degradation of the bacterial body. As for its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure both small molecule inhibitors and protein inhibitors of HNE inhibit the inflammatory response and the development of emphysema (Wright, J. L. et al. *Am. J. Respir. Crit. Care Med.* 2002, 166, 954-960; and Churg, A. et al. *Am. J. Respir. Crit. Care Med.* 2003, 168, 199-207, which are incorporated herein by reference in their entireties). Thus, HNE may play a role both in matrix destruction and in amplifying inflammatory responses in chronic respiratory diseases where neutrophil influx is a characteristic feature. Indeed, HNE is believed to play a role in several pulmonary diseases, including chronic obstructive pulmonary disease (COPD), cystic fibrosis (CF), acute respiratory distress syndrome (ARDS), pulmonary emphysema, pneumonia and lung fibrosis. It is also implicated in several cardiovascular diseases in which tissue remodelling is involved, for example, in heart failure and the generation of ischaemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (Thompson, A. B.; Daughton, D.; et al. *Am. Rev. Respir. Dis.* 1989, 140, 1527-1537, which is incorporated herein by reference in its entirety). The major pathogenic determinant in COPD has long been considered to be the protease-anti-protease balance (also known as the "elastase:anti-elastase hypothesis"), in which an imbalance of HNE and endogenous antiproteases such as α1-antitrypsin ($\alpha_1$-AT), secretory leukocyte protease inhibitor (SLPI) and pre-elafin leads to the various inflammatory disorders of COPD. Individuals that have a genetic deficiency of the protease inhibitor α1-antitrypsin develop emphysema that increases in severity over time (Laurrell, C. B.; Erikkson, S *Scand. J. Clin. Invest.* 1963 15, 132-140, which is incorporated herein by reference in its entirety). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Several human neutrophil inhibitors have need disclosed so far in the art. In particular, International Patent Applications No. WO2011/110858 and No. WO2011/110859, both of which are incorporated herein by reference in their entireties, describe some pyrimidine derivatives having human neutrophil elastase inhibitory properties and their use in therapy. Other HNE inhibitors are described in the International Patent Application No. WO2014/095700, which is incorporated herein by reference in its entirety.

Although several HNE inhibitors have been disclosed so far as above reported, there is still a need for further FINE inhibitors. Particularly, there is still a need for further HNE inhibitors endowed with a high potency for HNE enzyme inhibition. Particularly advantageous would also be the identification of further FINE inhibitors endowed with a high potency for HNE enzyme inhibition and which would show an appropriate developability profile as an inhalation treatment.

SUMMARY OF THE INVENTION

Accordingly, it is one object of the present invention to provide novel pyrimidinone derivatives which exhibit human neutrophil elastase inhibitory properties.

It is another object of the present invention to provide novel therapeutic uses of such a compound.

It is another object of the present invention to provide novel methods of preparing such a compound.

It is another object of the present invention to provide novel pharmaceutical compositions which contain such a compound.

It is another object of the present invention to provide novel metered dose inhalers and kits which contain such a compound.

These and other objects, which will become apparent during the following detailed description, have been achieved by the inventors' discovery of the compounds of the present invention.

Thus, in one aspect the present invention provides a compound of formula (I), or a pharmaceutically acceptable salt thereof:

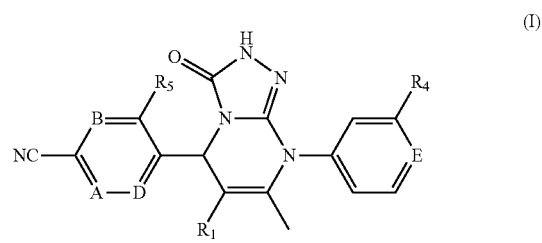

wherein
A is CH or N;
B is CH or N;
D is CH or N;
E is CH or N;
$R_1$ is —CN or a group —C(O)—V$R_2$;

V is selected from the group consisting of —O—, —(CH$_2$)—, and —NH—;

R$_2$ is hydrogen or —(C$_1$-C$_6$)alkyl, optionally substituted with one or more substituents selected from the group consisting of halogen, OR$_3$ and —NR$_3$R$_7$;

R$_3$ is hydrogen or optionally substituted (C$_1$-C$_6$)alkyl;

R$_4$ is selected from —CF$_3$ and —CHF$_2$,

R$_5$ is a group selected from

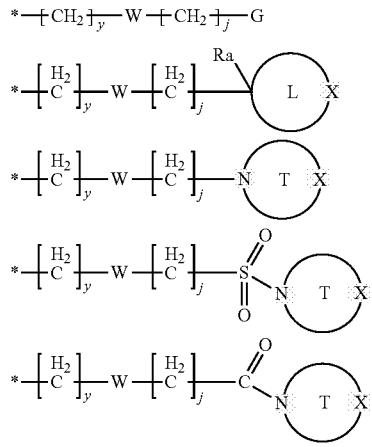

j is 0 or an integer ranging from 1 to 4;

y is 0 or an integer ranging from 1 to 4;

L and T are independently a 4 to 8-membered heterocycloalkyl ring bringing an —X— group in any of the free position;

X is selected from —O—, —S—, —S(O$_2$)— and —NR$_6$;

W is selected from the group consisting of —N(R$_3$)—, —O—, —C(O)—, —OC(O)N(R$_3$)—, —N(R$_3$)C(O)N (R$_3$)—, —C(O)N(R$_3$)—, —NR$_3$C(O)—, —SO$_2$—, —SO$_2$N (R$_3$)—, —NR$_3$S(O$_2$)—, —S—, —C(O)O—, —OC(O)—, optionally substituted (C$_1$-C$_6$)alkylene, optionally substituted (C$_3$-C$_6$)cycloalkylene and optionally substituted (C$_4$-C$_7$)heterocycloalkylene;

G is hydrogen or is selected from the group consisting of halogen, —CN, —N(R$_3$)(R$_7$), —OR$_3$, —OC(O)OR$_3$, —OC(O)NR$_3$R$_7$, —N(R$_3$)C(N)N(R$_3$)(R$_7$), —N(R$_3$)C(O)N(R$_3$) (R$_7$), —C(O)N(R$_3$)(R7), —N(R$_3$)C(O)R$_7$, —S(O$_2$)R$_3$, —S(O$_2$)N(R$_3$)(R$_7$), —N(R$_3$)S(O$_2$)(R$_7$), —SR$_3$, —C(O) OR$_3$, —OC(O)R$_3$, optionally substituted (C$_1$-C$_6$)alkyl, optionally substituted (C$_3$-C$_6$)cycloalkyl and optionally mono or bi-substituted (C$_4$-C$_7$)heterocycloalkyl;

Ra is hydrogen or is selected from the group consisting of —OH, —NH$_2$ and optionally substituted (C$_1$-C$_6$)alkyl;

R$_6$ is hydrogen or is selected in the group consisting of —S(O$_2$)R$_7$, —CO$_2$R$_7$, —CONR$_3$R$_7$, —SO$_2$NR$_3$R$_7$ and optionally substituted (C$_1$-C$_6$)alkyl;

R$_7$ is hydrogen or is optionally substituted (C$_1$-C$_6$)alkyl; wherein, unless otherwise specified, optionally substituted means optionally substituted by one or more substituents selected from the group consisting of (C$_1$-C$_6$)alkyl, (C$_1$-C$_6$) alkoxy, (C$_1$-C$_6$)hydroxyalkyl, —OH, —NH$_2$, halogen, —CF$_3$ and —OCF$_3$; —NR$_3$R$_7$ and pharmaceutically acceptable salts thereof, with the provisos that when y is an integer ranging from 1 to 4, W is —O— and j is 0, then G is not hydrogen or (C$_1$-C$_6$)alkyl optionally substituted by one or more (C$_1$-C$_6$)alkoxy;

when y is an integer ranging from 1 to 4, W is —N(R$_3$)—, R$_3$ is hydrogen or (C$_1$-C$_6$)alkyl and j is 0, then G is not hydrogen or (C$_1$-C$_6$)alkyl;

when y is 0, W is —C(O)N(R$_3$)—, R$_3$ is hydrogen or (C$_1$-C$_6$)alkyl and j is 0, then G is not H or (C$_1$-C$_6$)alkyl optionally substituted with —NR$_3$R$_7$, wherein R$_3$ and R$_7$ are independently H or (C$_1$-C$_6$)alkyl;

when y is 0, W is —S(O$_2$)— and j is 0, then G is not (C$_1$-C$_6$)alkyl optionally substituted with —OH;

when y is 0, W is —S(O$_2$)N(R$_3$)—, R$_3$ is H and j is 0, then G is not hydrogen; and when y is 0, W is —S(O$_2$)N(R$_3$)—, R$_3$ is H or (C$_1$-C$_4$) alkyl and j is 0, then G is not hydrogen or (C$_1$-C$_6$)alkyl.

Compounds of formula (I) may be prepared in the form of salts, particularly pharmaceutically acceptable salts, N-oxides, hydrates, solvates and polymorphs thereof. Any reference to a compound herein, or reference to "compounds of the invention", "compounds of formula (I)", and the like includes such compounds whether or not in salt, N-oxide, hydrate, solvate or polymorphic form.

Compounds of the present invention may be used in the treatment or prevention of diseases in which HNE is implicated, for example chronic obstructive pulmonary disease (COPD), bronchiectasis, chronic bronchitis, lung fibrosis, pneumonia, acute respiratory distress syndrome (ARDS), pulmonary emphysema, smoking-induced emphysema and cystic fibrosis.

Hence other aspects of the present invention are (i) a pharmaceutical composition comprising a compound of the invention and a pharmaceutically acceptable carrier or excipient; and (ii) the use of a compound of the invention for the manufacture of a medicament for the treatment or prevention of a disease or condition in which HNE is implicated.

DETAILED DESCRIPTION OF THE PREFERRED EMBODIMENTS

The term "(C$_a$-C$_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl. and n-hexyl.

By analogy, the expression "(C$_a$-C$_b$)alkylene" refers to a divalent alkyl radical as above defined.

The term "(C$_a$-C$_b$)cycloalkyl", wherein a and b are integers, refers to saturated monocyclic, bicyclic or tricyclic hydrocarbon groups containing from a to b ring carbon atoms, as appropriate. Examples include cyclopropyl, cyclobutyl, cyclopentyl, cyclohexyl, cycloheptyl, and adamantyl.

By analogy, the expression "(C$_a$-C$_b$)cycloalkylene", wherein a and b, are integers refers to a divalent cyclic radical as above defined.

As used herein, the term "(C$_a$-C$_b$)heterocycloalkyl", wherein a and b are integers, relates to a saturated mono- or bi-cyclic non-aromatic radical in which at least one ring carbon atom is replaced by a heteroatom (e.g. —N—, —NH—, —S—, —O— or —S(O$_2$)—). Examples of (C$_a$-C$_b$)heterocycloalkyl include pyrrolidinyl, thiazolidinyl, piperazinyl, piperidinyl, morpholinyl, thiomorpholinyl.

By analogy, the expression "(C$_a$-C$_b$)heterocycloalkylene", wherein a and b are integers, refers to a divalent heterocyclic radical as above defined. In particular, the expression "(C$_a$-C$_b$)heterocycloalkylene" refers to a divalent (C$_a$-C$_b$)heterocycloalkyl radical (such as for example pyrrolidinene) wherein "(C$_a$-C$_b$)heterocycloalkyl group is as above defined.

L is a 4 to 8-membered heterocycloalkyl ring linked to the rest of the molecule through a carbon atom substituted with a Ra group, wherein said heterocycloalkyl ring brings an —X— group, selected from —O—, —S—, —S(O₂)— and —NR₆, in any of the free position;

T is a 4 to 8-membered heterocycloalkyl ring linked to the rest of the molecule through a nitrogen atom, wherein said heterocycloalkyl ring brings an —X— group, selected from —O—, —S—, —S(O₂)— and —NR₆, in any of the free position;

The term "(C$_a$-C$_b$) alkoxy" wherein a and b are integers, refers to straight-chained and branched alkoxy groups wherein the number of constituent carbon atoms is in the range from a to b. Particular alkyl groups are methoxyl, ethoxyl, n-propoxyl, isopropoxyl, and t-butoxyl.

The term "salt" includes base addition and acid addition salts.

The term "pharmaceutically acceptable salts" refers to derivatives of compounds of formula (I) wherein the parent compound is suitably modified by converting any of the free acid or basic group, if present, into the corresponding addition salt with any base or acid conventionally intended as being pharmaceutically acceptable.

Compounds of the present invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine, and the like. Those compounds which are basic can form salts, including pharmaceutically acceptable salts with inorganic acids, e.g. with hydrohalic acids such as hydrochloric or hydrobromic acids, sulphuric acid, nitric acid or phosphoric acid, and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids, and the like. Those compounds which have quaternary nitrogen can also form quaternary salts with a pharmaceutically acceptable counter-ion such as chloride, bromide, acetate, formate, p-toluenesulfonate, succinate, hemi-succinate, naphthalene-bis sulfonate, methanesulfonate, xinafoate, and the like.

Where the compounds of the present invention have at least one stereogenic center, they may exist as enantiomers. When the compounds according to the invention possess two or more stereogenic centers, they may additionally exist as diastereoisomers. It is to be understood that all such isomers and mixtures thereof in any proportion are encompassed within the scope of the present invention.

It will be apparent that compounds of general formula (I) at least contain one stereogenic center, namely represented by the carbon atom (1) with an asterisk below, and therefore exist as optical stereoisomers:

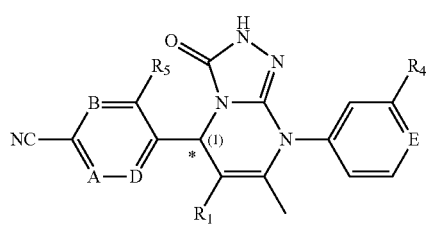

(I)

In one embodiment, the present invention is directed to compounds of formula (I)', which are compounds of formula (I) as above defined where the absolute configuration of carbon (1) is that shown here below:

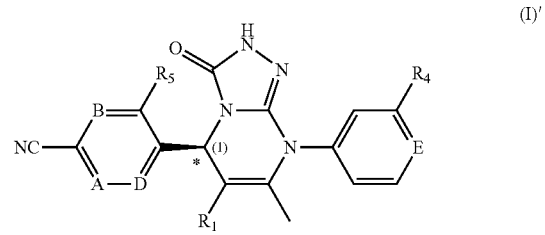

(I)'

In another embodiment, the present invention is directed to compounds of formula (I)″, which are compounds of formula (I) as above defined where the absolute configuration of carbon (1) is that shown herebelow:

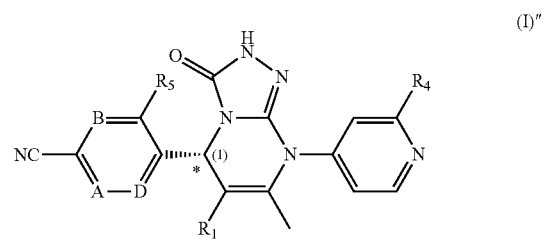

(I)″

The absolute configuration for carbon (1) is assigned on the basis of Cahn-Ingold-Prelog nomenclature based on groups' priorities.

It is to be understood that all preferred groups or embodiments described here below for compounds of formula (I) may be combined among each other and apply as well to compounds of formula (I)' and (I)″ mutatis mutandis.

In one embodiment, for compounds of formula (I), A is CH, B is CH and D is CH.

In one embodiment, for compounds of formula (I), R₅ is a group

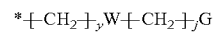

wherein W is selected from the group consisting of —C(O)—, —OC(O)N(R₃)—, —N(R₃)C(O)N(R₃)—, —NR₃C(O)—, —NR₃S(O₂)—, —S—, —C(O)O—, —OC(O)—, optionally substituted (C₁-C₆)alkylene, optionally substituted (C₃-C₆)cycloalkylene and optionally substituted (C₄-C₇)heterocycloalkylene.

In one embodiment, for compounds of formula (I), R₅ is a group

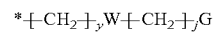

wherein y is 2, W is —NR₃S(O₂)—, R₃ is hydrogen or optionally substituted (C₁-C₆)alkyl, j is 1 and G is hydrogen.

In another embodiment, for compounds of formula (I), R₅ is a group

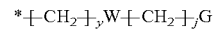

wherein y is 2 or 3, W is —S—, j is 0 and G is optionally substituted (C₁-C₆)alkyl.

In another embodiment, for compounds of formula (I), R₅ is a group

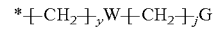

wherein y is 2 or 3, W is —SO₂—, j is 0 and G is optionally substituted (C₁-C₆)alkyl.

In another embodiment, for compounds of formula (I), $R_5$ is a group

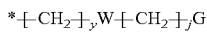

wherein y is 2 or 3, W is $-NR_3C(O)-$, $R_3$ is hydrogen or optionally substituted $(C_1-C_6)$alkyl, j is 1 and G is hydrogen.

In one embodiment, for compounds of formula (I), $R_5$ is a group selected from

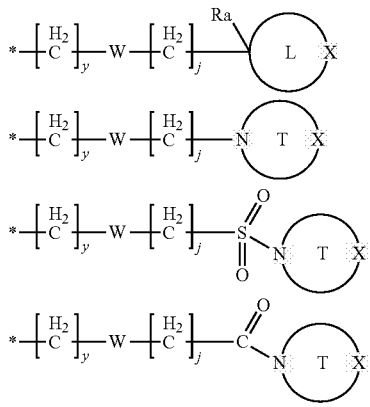

wherein Ra is hydrogen or is selected from the group consisting of $-OH$, $-NH_2$ and optionally substituted $(C_1-C_6)$alkyl; L and T are independently a 4 to 8-membered heterocycloalkyl ring bringing an $-X-$ group in any of the free position; X is selected from $-O-$, $-S-$, $-S(O_2)-$ and $-NR_6$; $R_6$ is hydrogen or is selected in the group consisting of $-SO_2R_7$, $-CO_2R_7$, $-CONR_3R_7$, $-SO_2NR_3R_7$ and optionally substituted $(C_1-C_6)$alkyl; $R_3$ and $R_7$ are independently hydrogen or optionally substituted $(C_1-C_6)$alkyl.

In one embodiment, for compounds of formula (I), $R_4$ is selected from $-CF_3$ and $-CHF_2$.

In one embodiment, for compounds of formula (I), $R_1$ is $-CN$ or a group $-C(O)-VR_2$; V is $-O-$; $R_2$ is $-(C_1-C_6)$alkyl optionally substituted with one or more substituents selected from the group consisting of halogen, $-OR_3$ and $-NR_3R_7$.

In one embodiment, for compounds of formula (I), $R_5$ is a group

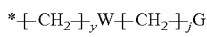

wherein y is 0, W is $-C(O)N(R_3)-$, j is 2, G is $-OR_3$ and $R_3$ is hydrogen or optionally substituted $(C_1-C_6)$alkyl.

In one embodiment, for compounds of formula (I), $R_5$ is a group

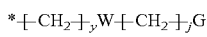

wherein y is 0, W is $-C(O)N(R_3)-$, j is 0, G is $(C_1-C_6)$ alkyl optionally substituted by $-OH$ and $R_3$ is hydrogen or optionally substituted $(C_1-C_6)$alkyl.

In one embodiment, for compounds of formula (I), $R_5$ is a group

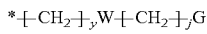

wherein y is 0, W is $-C(O)N(R_3)-$, j is 0, G is $(C_3-C_6)$ cycloalkyl and $R_3$ is hydrogen or optionally substituted $(C_1-C_6)$alkyl.

In one embodiment, for compounds of formula (I), $R_5$ is a group

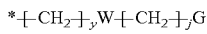

wherein y is 0, W is $-C(O)N(R_3)-$, j is 2, G is $-S(O_2)R_3$ and $R_3$ is hydrogen or optionally substituted $(C_1-C_6)$alkyl.

In one embodiment, for compounds of formula (I), $R_5$ is a group

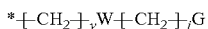

wherein y is 1, W is $-C(O)N(R_3)-$, j is 0, G is $(C_1-C_6)$ alkyl and $R_3$ is hydrogen or optionally substituted $(C_1-C_6)$ alkyl.

In one embodiment, for compounds of formula (I) $R_5$ is a group

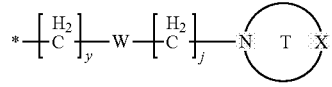

wherein y is 1, W is $-C(O)-$, j is 0, T is a 4 to 8-membered heterocycloalkyl ring bringing an $-X-$ group wherein X is $-O-$.

In one embodiment, for compounds of formula (I), $R_5$ is a group

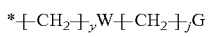

wherein y is 2, W is $-N(R_3)-$, $R_3$ is hydrogen or optionally substituted $(C_1-C_6)$alkyl, j is 1, G is $(C_4-C_7)$heterocycloalkyl.

In one embodiment, for compounds of formula (I), $R_5$ is a group

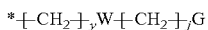

wherein y is 2, W is $(C_4-C_7)$heterocycloalkylene, j is 1, G is $-N(R_3)(R_7)$, wherein $R_3$ and $R_7$ are independently hydrogen or optionally substituted $(C_1-C_6)$alkyl.

In one embodiment, for compounds of formula (I), $R_5$ is a group

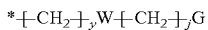

wherein y is 2, W is $-N(R_3)-$, $R_3$ is $(C_1-C_6)$alkyl, j is 0, G is $(C_4-C_7)$heterocycloalkyl.

In one embodiment, for compounds of formula (I), $R_5$ is a group

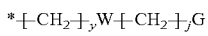

wherein y is 2, W is $(C_4-C_7)$heterocycloalkylene, j is 0, G is $-N(R_3)(R_7)$, wherein $R_3$ and $R_7$ are independently hydrogen or optionally substituted $(C_1-C_6)$alkyl.

In one embodiment, for compounds of formula (I), $R_5$ is a group

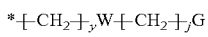

wherein y is 2, W is $-N(R_3)-$, $R_3$ is $(C_1-C_6)$alkyl, j is 3, G is $-N(R_3)(R_7)$, wherein $R_3$ and $R_7$ are independently hydrogen or optionally substituted $(C_1-C_6)$alkyl.

In one embodiment, for compounds of formula (I), $R_5$ is a group

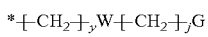

wherein y is 0, W is $-N(R_3)C(O)N(R_3)-$, j is 0, G is $(C_1-C_6)$alkyl and $R_3$ is $(C_1-C_6)$alkyl optionally substituted by $-OH$ or $-NR_3R_7$ wherein $R_3$ and $R_7$ are independently hydrogen or optionally substituted $(C_1-C_6)$alkyl.

In one embodiment, for compounds of formula (I), $R_5$ is a group

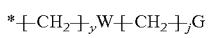

wherein y is 0, W is —N(R₃)—, j is 0, G is —C(O)OR₃ wherein R₃ is hydrogen or (C₁-C₆)alkyl optionally substituted by NR₃R₇ wherein R₃ and R₇ are independently hydrogen or optionally substituted (C₁-C₆)alkyl.

In one embodiment, for compounds of formula (I), R₅ is a group

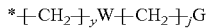

wherein y is 0, W is —NR₃C(O)—, j is 0, G is (C₁-C₆)alkyl and R₃ is hydrogen.

In one embodiment, for compounds of formula (I), R₅ is a group

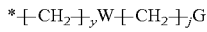

wherein y is 0, W is —O—, j is 0, G is (C₁-C₆)alkyl.

In one embodiment, for compounds of formula (I), R₅ is a group

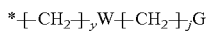

wherein y is 0, W is —O—, j is 2, G is —OR₃ and R₃ is hydrogen or optionally substituted (C₁-C₆)alkyl.

In one embodiment, for compounds of formula (I), R₅ is a group

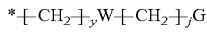

wherein y is 0, W is (C₁-C₆)alkylene optionally substituted by —OH, j is 2, G is —OR₃ wherein R₃ is hydrogen or optionally substituted (C₁-C₆)alkyl.

In one embodiment, for compounds of formula (I), R₅ is a group

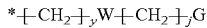

wherein y is 0, W is (C₁-C₆)alkylene optionally substituted by —OH, j is 0, G is —OR₃ wherein R₃ is hydrogen or optionally substituted (C₁-C₆)alkyl.

In one embodiment, for compounds of formula (I), R₅ is a group

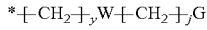

wherein y is 0, W is (C₁-C₆)alkylene optionally substituted by —OH, j is 0, G is —S(O₂)R₃ wherein R₃ is hydrogen or optionally substituted (C₁-C₆)alkyl.

In one embodiment, for compounds of formula (I), R₅ is a group

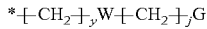

wherein y is 0, W is (C₁-C₆)alkylene optionally substituted by —OH, j is 0, G is (C₁-C₆)alkyl.

In another embodiment, the compound of the present invention is selected in the group consisting of:

(R)-5-[4-Cyano-2-(R)-1,2-dihydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-(S)-1,2-dihydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[2-(2-Acetylamino-propyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-{2-(3-Acetyl-methyl-amino)-propyl]-4-cyano-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-{4-Cyano-2-[3-(methanesulfonyl-1-methylamino)-propyl]-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[2-(2-Acetylamino-ethyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[2-(2-Acetylamino-ethyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-{2-[2-(Acetyl-methyl-amino)-ethyl]-4-cyano-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-(2-methanesulfonylamino-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-{4-Cyano-2-[3-(methanesulfonyl-1-methylamino)-ethyl]-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-(2-methylsulfanyl-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-(2-methanesulfonyl-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-(2-methylsulfanyl-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-(2-methanesulfonyl-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester.

(R)-5-[4-Cyano-2-(2-hydroxy-ethylcarbamoyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-((R)-2-hydroxy-1-methyl-ethylcarbamoyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-((S)-2-hydroxy-1-methyl-ethylcarbamoyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-(4-Cyano-2-cyclopropylcarbamoyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-(2-methanesulfonyl-ethylcarbamoyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-((R)-1-hydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-((S)-1-hydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-(4-Cyano-2-methylcarbamoylmethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-(4-Cyano-2-dimethylcarbamoylmethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-(2-morpholin-4-yl-2-oxo-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-{2-[2-(Azetidin-3-ylmethyl-methyl-amino)-ethyl]-4-cyano-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester formate salt;

(R)-5-{4-Cyano-2-[2-(3-methylaminomethyl-azetidin-1-yl)-ethyl]-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester formate salt;

(R)-5-{4-Cyano-2-[2-(methyl-piperidin-4-yl-amino)-ethyl]-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester formate salt;

(R)-5-{4-Cyano-2-[2-(4-dimethylamino-piperidin-1-yl)-ethyl]-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-(4-Cyano-2-{2-[(3-dimethylamino-propyl)-methyl-amino]-ethyl}-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-(3-ethyl-ureido)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-{4-Cyano-2-[3-(2-hydroxy-ethyl)-ureido]-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-{4-Cyano-2-[3-(2-dimethylamino-ethyl)-ureido]-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-(2-Acetylamino-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-(4-Cyano-2-ethoxycarbonylamino-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-[4-Cyano-2-(2-dimethylamino-ethoxycarbonylamino)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-(2-Acetylamino-4-cyano-phenyl)-7-methyl-3-oxo-8-(3-trifluoro methyl-phenyl)-2,3,5,8-tetrahydro-[1,2,4]triazolo[4,3-a]pyrimidine-6-carboxylic acid methyl ester;

(S)-5-(2-Acetylamino-4-cyano-phenyl)-7-methyl-3-oxo-8-(3-trifluoro methyl-phenyl)-2,3,5,8-tetrahydro-[1,2,4]triazolo[4,3-a]pyrimidine-6-carboxylic acid methyl ester;

(R)-5-[4-Cyano-2-(2-methoxy-ethoxy)-phenyl]-7-methyl-3-oxo-8-(3 trifluoromethyl-phenyl)-2,3,5,8-tetrahydro-[1,2,4]triazolo[4,3-a]pyrimidine-6-carboxylic acid methyl ester;

(S)-5-[4-Cyano-2-(2-methoxy-ethoxy)-phenyl]-7-methyl-3-oxo-8-(3 trifluoromethyl-phenyl)-2,3,5,8-tetrahydro-[1,2,4]triazolo[4,3-a]pyrimidine-6-carboxylic acid methyl ester;

(R)-5-[4-Cyano-2-((S)-1,2-dihydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carbonitrile;

(R)-5-[4-Cyano-2-((R)-1,2-dihydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carbonitrile;

(R)-5-[4-Cyano-2-(2-hydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carbonitrile;

(R)-5-[4-Cyano-2-(2-methanesulfonyl-ethyl)-phenyl]-7-methyl-3-oxo-8-(3-trifluoromethyl-phenyl)-2,3,5,8-tetrahydro-[1,2,4]triazolo[4,3-a]pyrimidine-6-carbonitrile;

(R)-5-[4-Cyano-2-(2-hydroxy-ethyl)-phenyl]-8-(3-difluoromethyl-phenyl)-7-methyl-3-oxo-2,3,5,8-tetrahydro-[1,2,4]triazolo[4,3-a]pyrimidine-6-carbonitrile;

(S)-5-[4-Cyano-2-(2-hydroxy-ethyl)-phenyl]-8-(3-difluoromethyl-phenyl)-7-methyl-3-oxo-2,3,5,8-tetrahydro-[1,2,4]triazolo[4,3-a]pyrimidine-6-carbonitrile;

(R) and (S)-5-[4-Cyano-2-(1,2-dihydroxy-ethyl)-phenyl]-8-(3-difluoromethyl-phenyl)-7-methyl-3-oxo-2,3,5,8-tetrahydro-[1,2,4]triazolo[4,3-a]pyrimidine-6-carbonitrile;

(R) and (S)-5-[4-Cyano-2-(1,2-dihydroxy-ethyl)-phenyl]-8-(3-difluoromethyl-phenyl)-7-methyl-3-oxo-2,3,5,8-tetrahydro-[1,2,4]triazolo[4,3-a]pyrimidine-6-carbonitrile The therapeutic utility of the present compounds is pertinent to any disease that is known to be at least partially mediated by the action of human neutrophil elastase. For example, the present compounds may be beneficial in the treatment of chronic obstructive pulmonary disease (COPD), cystic fibrosis (CF), bronchiectasis, acute respiratory distress syndrome (ARDS), pulmonary emphysema, pneumonia and lung fibrosis.

Compounds of the present invention are useful for treatment of inflammatory respiratory disorders, for example asthma (mild, moderate or severe), steroid resistant asthma, bronchitis, chronic obstructive pulmonary disease (COPD), cystic fibrosis (CF), pulmonary edema, pulmonary embolism, pneumonia, pulmonary sarcoidosis, pulmonary emphysema, silicosis, pulmonary fibrosis, pulmonary hypertension, respiratory failure, acute respiratory distress syndrome (ARDS), emphysema, chronic bronchitis, tuberculosis, aspergillosis and other fungal infections, hypersensitivity pneumonitis, vasculitic and thrombotic disorders of the lung vasculature, antitussive activity including treatment of chronic cough associated with inflammatory and secretory conditions of the airways, infection due to respiratory syncytial virus, influenza, coronavirus (including severe acute respiratory syndrome, SARS) and adenovirus, bronchiectasis and lung cancer.

The present invention also provides pharmaceutical formulations comprising, as an active ingredient, a compound of the invention. Other compounds may be combined with compounds of this invention for the prevention and treatment of inflammatory diseases of the lung. Thus, the present invention also provides pharmaceutical compositions for preventing and treating inflammatory diseases of the lung comprising a therapeutically effective amount of a compound of the invention and one or more other therapeutic agents.

Suitable therapeutic agents for a combination therapy with compounds of the invention include: (1) a corticosteroid, for example budesonide, beclomethasone, beclomethasone (e.g., as the mono or the dipropionate ester), flunisolide, fluticasone (e.g. as the propionate or furoate ester), Ciclesonide, mometasone (e.g. as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocortisone, desoxycorticosterone, rofleponide, etiprednol dicloacetate and the like. Steroid drugs can additionally include steroids in clinical or pre-clinical development for respiratory diseases such as GW-685698, GW-799943, GSK 870086, QAE397, NCX-1010, NCX-1020, NO-dexamethasone, PL-2146, NS-126 (formerly ST-126). Steroid drugs can also additionally include next generation molecules in development with reduced side effect profiles such as selective glucocorticoid receptor agonists (SEGRAs), including ZK-216348 and AZD5423; (2) a β2-adrenoreceptor agonist, such as albuterol, bambuterol, terbutaline, fenoterol, formoterol, formoterol fumarate, salmeterol, salmeterol xinafoate, arformoterol, arformoterol tartrate, indacaterol (QAB-149), carmoterol, BI 1744 CL, GSK159797 (milvetrol), GSK59790, GSK159802, GSK642444 (vilanterol), GSK678007, GSK96108, clenbuterol, procaterol, bitolterol, LAS 100977 (abediterol), BI1744 CL (olodaterol) and brodxaterol; (3) a leukotriene modulator, for example montelukast, zafirlukast or pranlukast; (4) anticholinergic agents, for example selective muscarinic-3 (M3) receptor antagonists such as ipratropium bromide, tiotropium, tiotropium bromide (Spiriva®), glycopyrronium bromide, aclidinium bromide, LAS34273, GSK656398, GSK233705, GSK 573719 (umeclidinium), LAS35201, QAT370 and oxytropium bromide; (5) phosphodiesterase-IV (PDE-IV) inhibitors, for example roflumilast, cilomilast or theophylline; (6) an antitussive agent, such as codeine or dextramorphan; and (7) a non-steroidal anti-inflammatory agent (NSAID), for example ibuprofen or ketoprofen; (8) a mucolytic, for example N acetyl cysteine or fudostein; (9) a expectorant/mucokinetic modulator, for example ambroxol, hypertonic solutions (e.g. saline or mannitol) or surfactant; (10) a peptide mucolytic, for example recombinant human deoxyribonoclease I (dornase-alfa and rhDNase) or helicidin; (11) antibiotics, for example azithromycin, tobramycin and aztreonam; and (12) p38 Mitogen Activated Protein (MAP) kinase inhibitors, such as GSK 856553 and GSK 681323; (12) inhibitors of Janus Kinases (JAK) such as CP-690550 or GLPG0634; (13) Spleen Tyrosine Kinase (SYK) inhibitors such as R406, R343 or PRT062607; (14) inhibitors of delta and/or gamma isoforms of Phosphatidylinositol 3-kinase (PI3K).; (15) anti-retroviral agents such as ribavirin, zanamivir or laninamivir; (16) PPAR-γ agonists such as pioglitazone and rosiglitazone.

In one aspect, the present invention provides for the use of inhaled administration of compounds of the invention in combination with other anti-inflammatory drugs and bronchodilator drug combinations (i.e. triple combination product), including but not limited to salmeterol xinafoate/fluticasone propionate (Advair/Seretide®), vilanterol/fluticasone furoate (BREO ELLIPTA™), formoterol fumarate/budesonide (Symbicort®), formoterol fumarate/mometasone furoate, formoterol fumarate/beclometasone dipropionate (Foster®), formoterol fumarate/fluticasone propionate (FlutiForm®), Indacaterol/mometasone furoate, Indacaterol/QAE-397, GSK159797/GSK 685698, GSK159802/GSK 685698, GSK642444/GSK 685698, formoterol fumarate/ciclesonide, and arformoterol tartrate/ciclesonide.

In another aspect, the present invention provides for the use of inhaled administration of compounds of the invention in combination with other bronchodilator drug combinations, particularly β2 agonist/M3 antagonist combinations (i.e. triple combination product), including but not limited to salmeterol xinafoate/tiotropium bromide, formoterol fumarate/tiotropium bromide, formoterol fumarate/glycopyrrolate (PT003), BI 1744 CL/tiotropium bromide, indacaterol/NVA237, indacaterol/QAT-370, formoterol/LAS34273, umeclidinium/vilanterol (Anoro™), GSK159797/GSK 573719, GSK159802/GSK 573719, GSK642444/GSK 573719, GSK159797/GSK 233705, GSK159802/GSK 233705, GSK642444/GSK 233705.

The weight ratio of the first and second active ingredients may be varied and will depend upon the effective dose of each ingredient. Generally, an effective dose of each will be used.

The magnitude of prophylactic or therapeutic dose of a compound of the invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

Another aspect of the present invention provides pharmaceutical compositions which comprise a compound of the invention and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the invention encompass any composition made by admixing a compound of the invention, additional active ingredient(s), and pharmaceutically acceptable excipients.

The pharmaceutical compositions of the present invention comprise a compound of the invention as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Any suitable route of administration may be employed for providing a mammal, especially a human, with an effective dosage of a compound of the present invention. In therapeutic use, the active compound may be administered by any convenient, suitable or effective route. Suitable routes of administration are known, and include oral, intravenous, rectal, parenteral, topical, ocular, nasal, buccal and pulmonary (by inhalation).

Compositions suitable for administration by inhalation are known, and may include carriers and/or diluents that are known for use in such compositions. The composition may contain 0.01-99% by weight of active compound. Preferably, a unit dose comprises the active compound in an amount of 1 µg to 10 mg.

The most suitable dosage level may be determined by any known suitable method. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease to be treated.

For delivery by inhalation, the active compound is preferably in the form of microparticles. They may be prepared by a variety of techniques, including spray-drying, freeze-drying and micronization.

By way of example, a composition of the present invention may be prepared as a suspension for delivery from a nebulizer or as an aerosol in a liquid propellant, for example for use in a pressurized metered dose inhaler (PMDI). Propellants suitable for use in a PMDI are known to the skilled person, and include CFC-12, HFA-134a, HFA-227, HCFC-22 (CCl2F2) and HFA-152 (CH4F2 and isobutane).

In a preferred embodiment of the present invention, a composition of the present invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 µm.

In the case of an aerosol-based formulation, a preferred composition is:

| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

Compounds of the present invention may be used in combination with other drugs that are used in the treatment/prevention/suppression or amelioration of the diseases or conditions for which present compounds are useful. Such other drugs may be administered, by a route and in an amount commonly used therefore, contemporaneously or sequentially with a compound of the invention. When a compound of the present invention is used contemporaneously with one or more other drugs, a pharmaceutical composition containing such other drugs in addition to the compound of the invention is preferred. Accordingly, the pharmaceutical compositions of the invention include those that also contain one or more other active ingredients, in addition to a compound of the invention.

The agents of the present invention may be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321, which is incorporated herein by reference in its entirety).

Methods of Synthesis

In one aspect of the present invention, a process for the preparation of compounds of the invention (Ia), i.e. compounds of formula (I) wherein $R_1$ is —C(O)—V$R_2$ is provided, according to general synthetic routes reported in Scheme A-J here below. E and $R_4$ are as defined above.

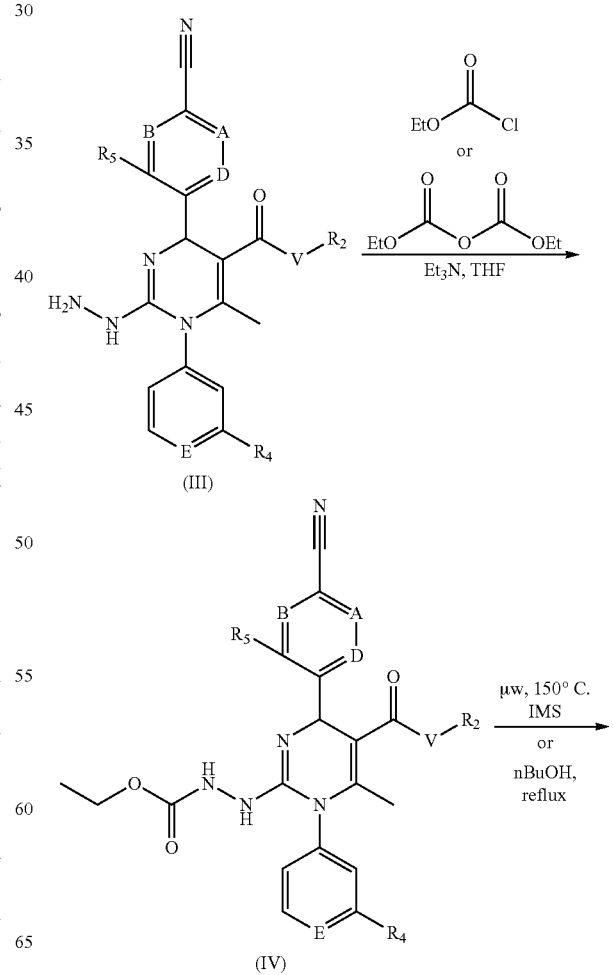

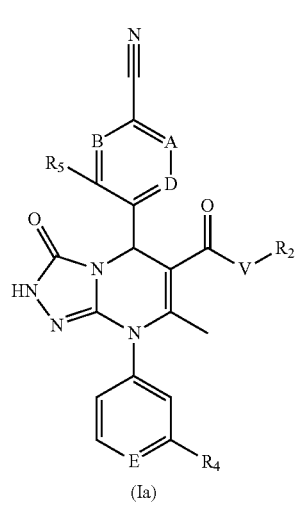

(Ia)

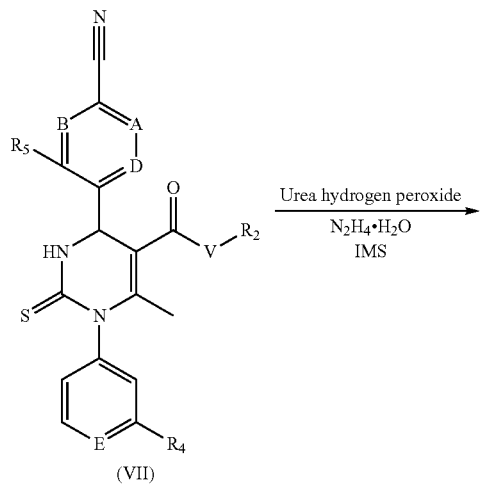

(VII)

Compounds of formula (IV) may be prepared from compounds of formula (III) by reaction with ethyl chloroformate (or ethyl pyrocarbonate) in the presence of a base such as triethylamine in a solvent such as THF at a temperature of from 0° C. to reflux. Compounds of formula (IV) may be transformed into compounds of formula (Ia) by heating in an appropriate solvent. Suitable conditions include the use of a solvent such as IMS and heating using microwave irradiation at a temperature of up to 150° C. or conventional heating in a solvent such as n-butanol at reflux.

Compounds of formula (III) wherein $R_2$ is $(C_1$-$C_6)$alkyl, may be prepared according to Scheme B below:

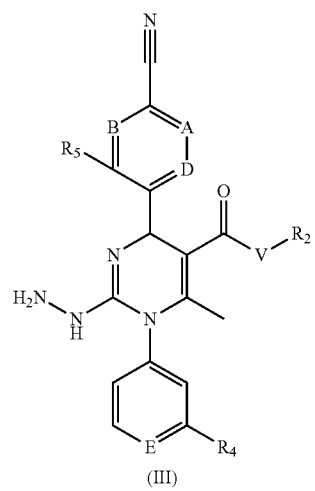

(III)

Compounds of formula (V) may be reacted with a benzaldehyde (VI), such as 3-bromo-4-formyl-benzonitrile and an acetoacetate such as ethyl acetoacetate in the presence of an acid such as TMS-polyphosphate or polyphosphoric acid in a solvent such as THF at a temperature of from room temperature to reflux to give compounds of formula (VII), wherein $R_2$ is $(C_1$-$C_6)$alkyl and the other groups are as defined for compounds of formula (I). Compounds of formula (III) may be prepared from compounds of formula (VII) by reaction with an oxidizing agent such as urea hydrogen peroxide followed by in-situ treatment with hydrazine hydrate in IMS.

Furthermore compounds of formula (Ia)', which are compounds of formula (I)' as above defined where the absolute configuration of carbon (1) is that shown herebelow can be prepared according to Scheme C.

Scheme B

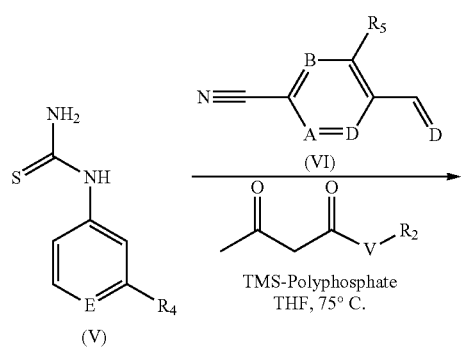

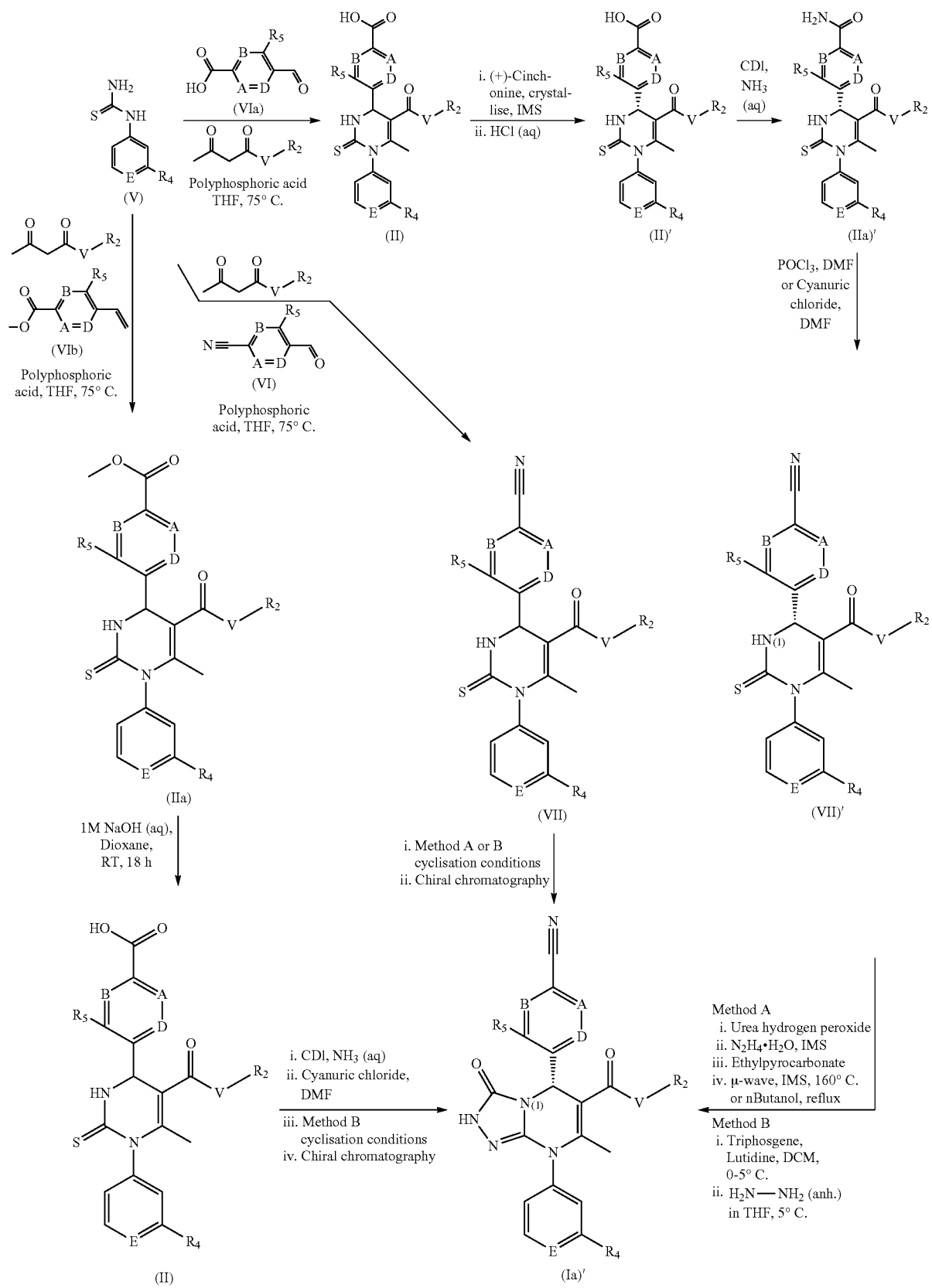
Scheme C

By way of example, compounds of formula (II) where E=CH and $R_4$=$CF_3$ may be obtained from compounds of formula (V) by reacting with 3-bromo-4-formyl-benzoic acid (VIa) using a similar method described for the transformation of compounds of formula (V) to compounds of formula (VII) in Scheme B. Compounds of formula (II)', which are compounds of formula (II) wherein the absolute configuration at stereogenic center (1) is as reported in Scheme C, may be obtained from compounds of formula (II) by forming a chiral diastereomeric salt with a suitable chiral amine such as (+)-Cinchonine in a suitable solvent such as dioxane, followed by treatment of the salt with an acid such as hydrochloric acid to give the enantiomerically pure compounds of formula (II)'. Compounds of formula (VII)', which are compounds of formula (VII) wherein the absolute configuration at stereogenic center (1) is as reported in Scheme C, may be prepared from compounds of formula (II)' by reaction with aqueous ammonia in the presence of a coupling agent such as carbonyl diimidazole in a solvent such as THF at a temperature of from 0° C. to room temperature to give the intermediate primary amide (IIa)'. Conversion of compounds of formula (IIa)' to compounds of formula (VII)' may be carried out using a dehydrating agent. Suitable conditions include the use of a solvent such as DMF and a dehydrating agent such as phosphorus oxychloride or cyanuric chloride at a temperature of from 0° C. to room temperature.

Compounds of formula (Ia)', which are compounds of formula (Ia) as above defined and wherein the absolute configuration of carbon (1) is that shown in Scheme C (Method A), may be obtained from compounds of formula (VII)' using similar methods described for the transformation of compounds of formula (VII) to compounds of formula (Ia) in Schemes B and A. Alternatively, compounds of formula (Ia)', which are compounds of formula (Ia) as above defined and wherein the absolute configuration of carbon (1) is that shown in Scheme C may be also be obtained from compounds of formula (VII)' using method B; wherein compounds of formula (VII)' may be reacted with a chlorocarbonyl-containing/releasing compound such as phosgene or triphosgene and anhydrous hydrazine in the presence of a base such as 2,6-lutadine in a solvent such as dichloromethane at a temperature of from −5-5° C. to give compounds of formula (Ia)' wherein $R_2$ is ($C_1$-$C_6$)alkyl and the other groups are as define for compounds of formula (I). Similarly, compounds of the invention (Ia)' may also be prepared from compounds of formula (VII) following cyclisation using either method A or B (see Scheme C) and separation of the desired enantiomer (Ia)' using chiral chromatography.

The skilled person would understand that by selecting of the appropriate chiral amine and its absolute configuration, derivatives of formula (II)', (IIa)', (VII)' and (Ia)' (which are compounds of formula (II), (VII), and (Ia) respectively wherein the absolute configuration at stereogenic center (1) is opposite to that reported in Scheme C) may be obtained.

Compounds of formula (X), wherein $R_1$ is a group —C(O)—$VR_2$ (wherein $R_2$=Me), A, B and D are CH and $R_5$ is bromine or other suitable activating group taken from the group, but not exclusively, Cl, I, OTf, may be prepared from compounds of formula (VIII) according to Scheme D here below reported:

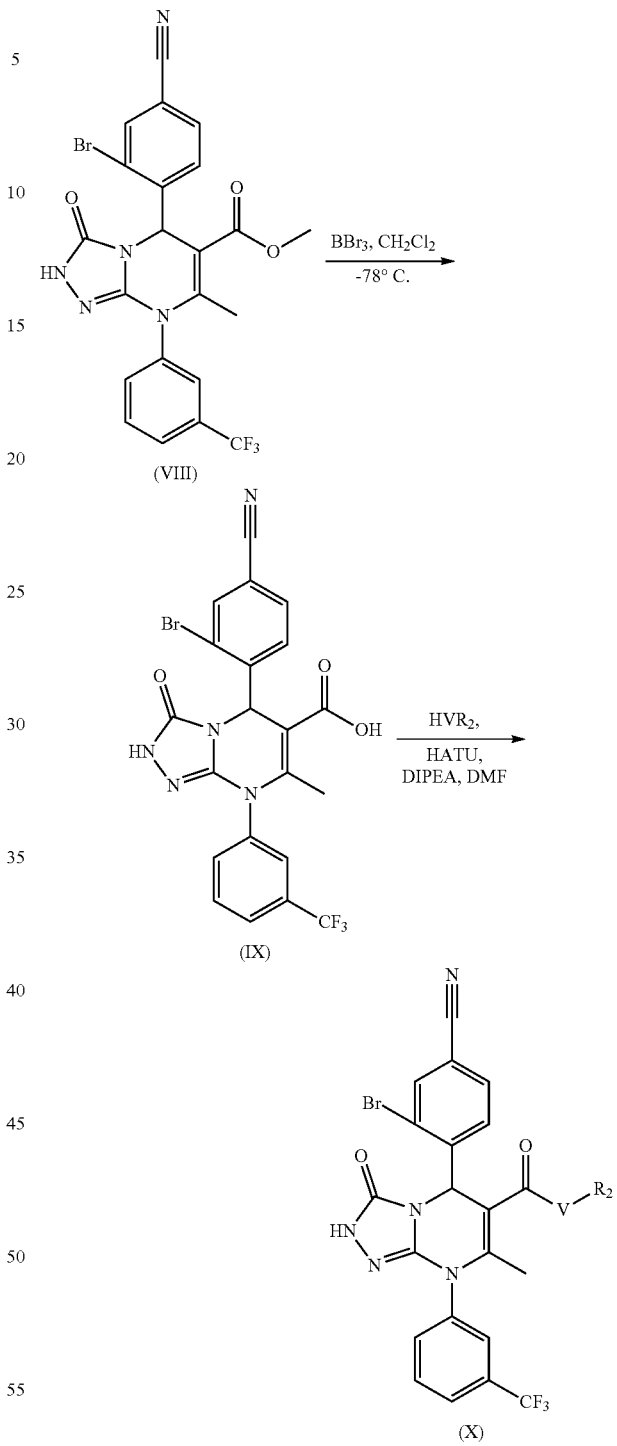

Scheme D

Treatment of a compound of formula (VIII) with a strong Lewis acid such as boron tribromide in a solvent such as DCM at a temperature of from −78° C. to room temperature followed by quench with water or methanol can provide compounds of formula (IX). In Scheme D it will be apparent to a person skilled in the art that one can start from the racemate (VIII) or from the single enantiomer.

It should be clear to the skilled person that other appropriate protecting group strategies may be contemplated and that the acid (IX) represents a versatile intermediate for further functionalization as well as for preparation of compounds of formula (X).

It is in fact to be underlined that many of the synthetic routes herebelow described starting from compounds of formula (VIII) (i.e. in Schemes F, G and H) or (VIII)' may be applicable, as the skilled person would understand, to compounds of formula (IX) and (X) also, to get to additional compounds of formula (I), (Ia) and (Ia)'.

By way of example, the derivatization of a compound of formula (IX), as above defined, into a compound of formula (X), wherein $R_2$ is not hydrogen, may be prepared by reaction with an alcohol or amine $HVR_2$ such as ammonia or 2-methoxy-ethanol in the presence of a coupling agent such as HATU in a solvent such as DMF in the presence of a base such as triethylamine at a temperature of from room temperature to 80° C. The synthetic route shown in Scheme D would be of benefit in introducing—$VR_2$ substituents at a late stage.

Scheme E

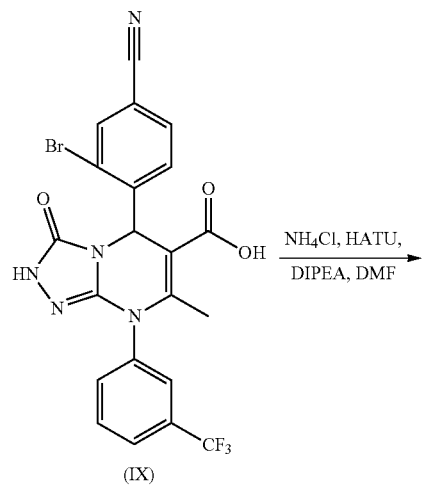

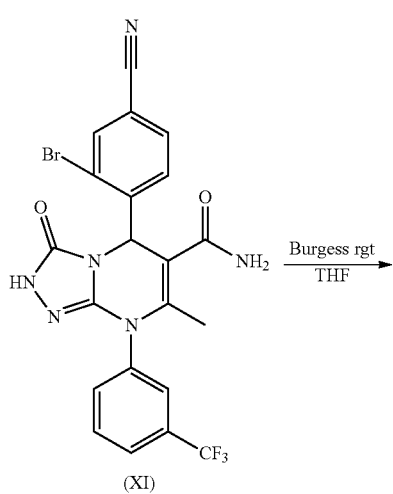

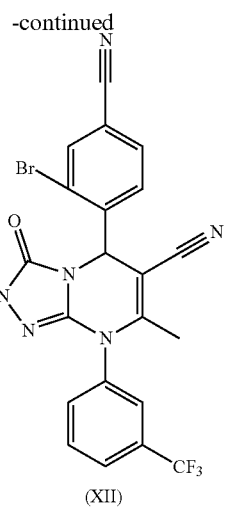

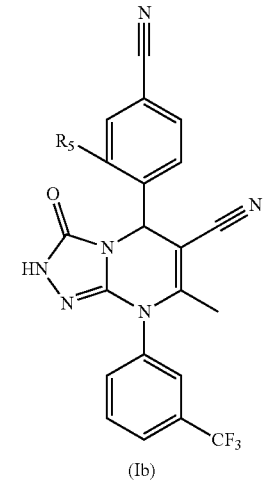

Compounds of formula (XII), i.e. compounds of formula (X) wherein $R_1$ (—C(O)—$VR_2$) is a group —CN, may be prepared according to Scheme E from compounds of formula (IX). Compounds of formula (XI), which are compounds of formula (X) wherein $VR_2$ is $NH_2$, may be prepared by reaction with ammonia in the presence of a coupling agent such as HATU in a solvent such as DMF in the presence of a base such as triethylamine at a temperature of from room temperature to 80° C.

Compounds of formula (XII) may be prepared from compounds of formula (XI) by reaction with a dehydrating agent such as Burgess reagent in a solvent such as THF at a temperature of from room temperature to reflux. In Scheme E it will be apparent to a person skilled in the art that one can start from the racemate (IX) or from the single enantiomer, which may be prepared from the single enantiomer of compounds of formula (VIII) according to Scheme D.

It will then be apparent to the skilled person that by adaptation of synthetic routes herebelow described in schemes F-J and starting from compounds of formula (XII), compounds of formula (Ib), i.e. compounds of formula (I) wherein $R_1$ is a cyano group, may be prepared Compounds of formula (Iq), i.e. compounds of formula (Ia) wherein $R_1$ (—C(O)—$VR_2$) is a group —CN and $R_4$ is a difluoromethyl group, may be prepared according to Scheme E' from compounds of formula (Va).

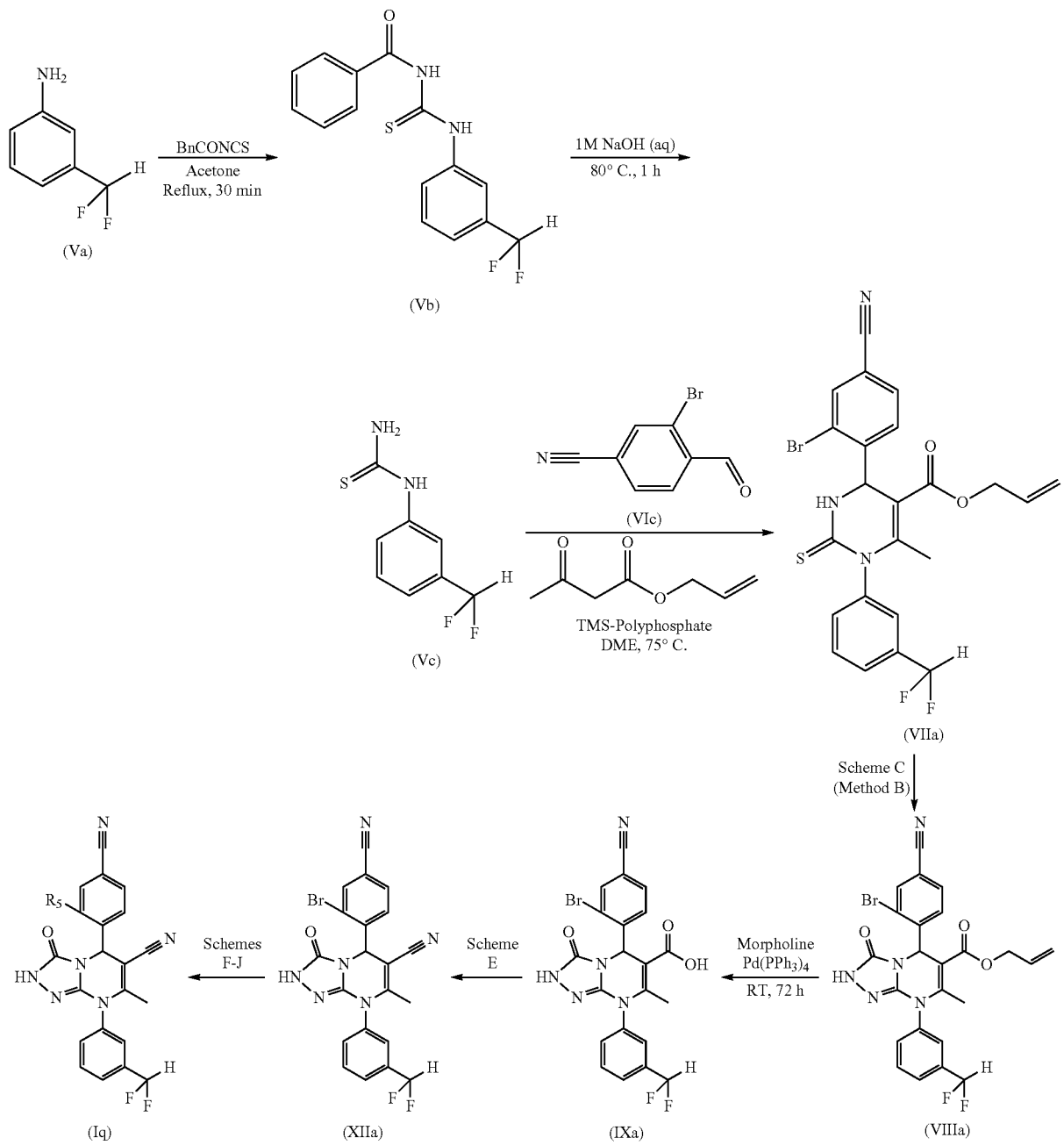

Compounds of formula (Vc) can be prepared following a 2 step procedure from compounds of formula (Va). Compounds of formula (Vb) are prepared from compounds of formula (Va) by reaction with benzoyl isocyante in a solvent such as acetone at a temperature from RT to reflux. Compounds of formula (Vc) can be obtained from compounds of formula (Vb) following hydrolysis with a suitable base such as 1 M aqueous sodium hydroxide at a temperature of between 50-80° C. Compounds of formula (VIIa) can be prepared by reaction of compounds of formula (Vc) with compounds of formula (VIc) and 3-oxo-butyric acid allyl ester, using similar conditions used to prepare compounds of formula (VII), (Scheme B). Compounds of formula (VIIIa) may be prepared from compounds of formula (VIIa) using a similar method to that used to prepare compounds of formula (Ia)' (Scheme C, Method B). Compounds of formula (IXa) can be obtained from compounds of formula (VIIIa) following treatment with a palladium catalyst such as tetrakis(triphenylphosphine)palladium(0) in the presence of an amine such as morpholine in a solvent such as THF at temperatures of between RT and 50° C.

It will then be apparent to the skilled person that by adaptation of the synthetic route shown in scheme E and those herebelow described in schemes F-J, starting from compounds of formula (IXa), compounds of formula (Iq), i.e. compounds of formula (I) wherein $R_1$ is a cyano group and $R_4$ is a difluoromethyl group, may be prepared.

Compounds of formula (Ic), (Id), (Ie) and (If) i.e. compounds of formula (I) wherein $R_1$ is a group —C(O)—VR$_2$, V is oxygen, $R_2$ is a methyl group, A, B and D are CH and $R_5$ is respectively a group as reported in Scheme F where $R_x$ may have different meanings according to those described for compounds of formula (I), may be prepared from compounds of formula (VIII) according to Scheme F here below reported:

Scheme F

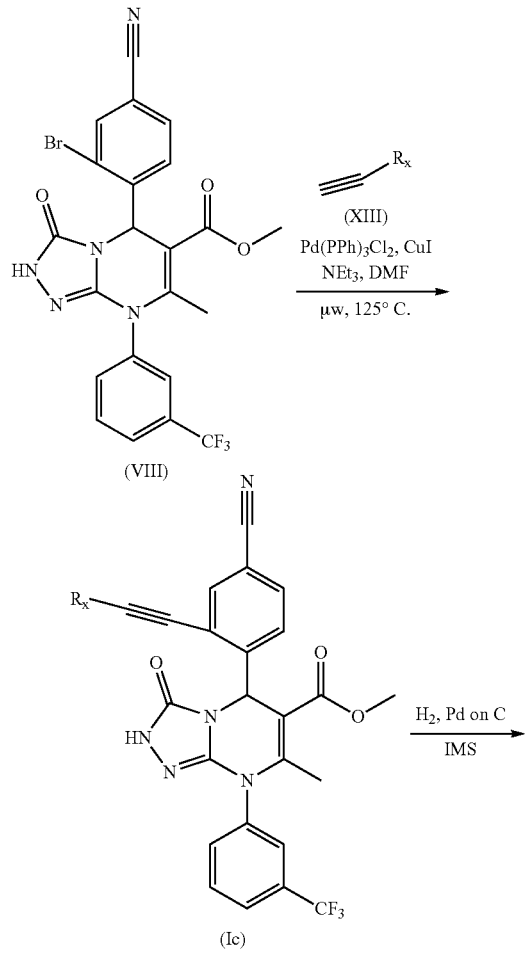

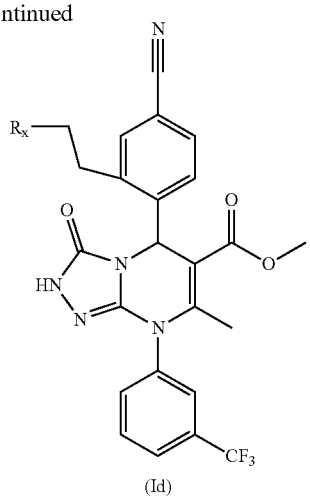

The transformation of compounds of formula (VIII) into compounds of formula (Ic) may be achieved by reaction with a suitably unsubstituted acetylic compound (XIII) in the presence of a catalytic mixture such as bis(triphenylphosphine) palladium(II) dichloride and copper (1) iodide with a base such as triethylamine in a solvent such as DMF at a temperature of up to 120° C., typically using microwave irradiation. Compounds of formula (Id) may be prepared from compounds of formula (Ic) by hydrogenation using a catalyst such as Pd/C in a solvent such as IMS.

Compounds of formula (Ie-Ih) i.e. compounds of formula (I) wherein $R_1$ is a group —C(O)—$VR_2$, V is oxygen, $R_2$ is a methyl group, A, B and D are CH and $R_5$ can be the ethylene glycol (Ie), a methylene linked tertiary amine —$NR_{18}R_{19}$ (If), an amide —$NR_{18}R_{19}CO$— (Ig) or a sulfonamide —$NR_{18}SO_2R_{20}$ (Ih), as defined above, may be prepared from compounds of formula (VIII) according to Scheme G below:

Scheme G

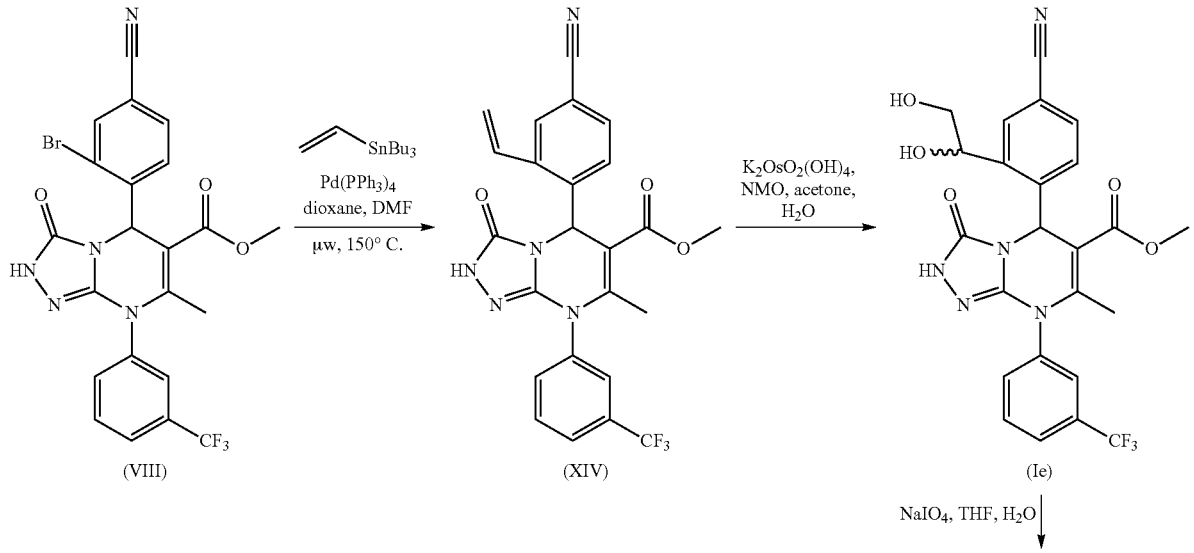

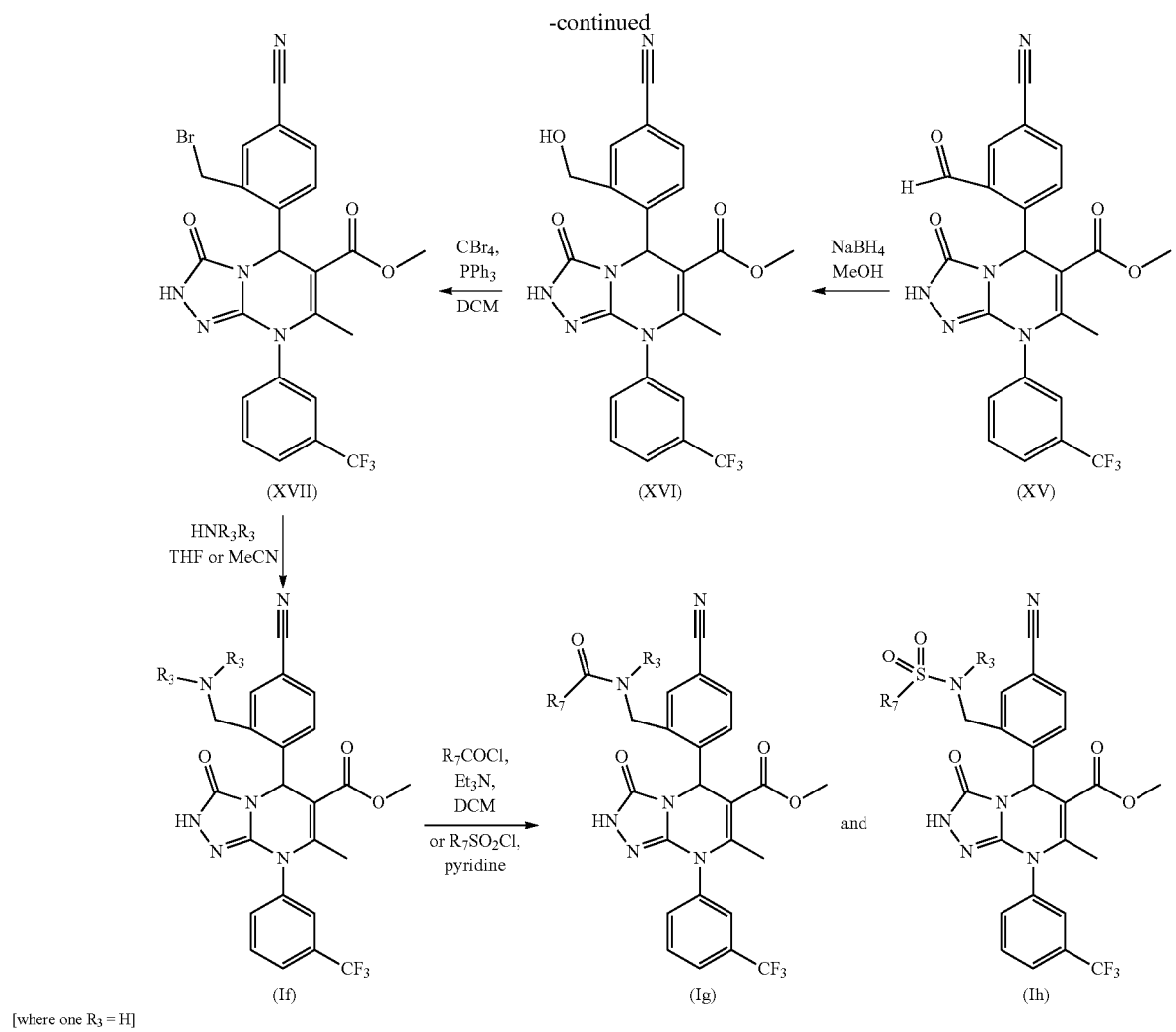

[where one R₃ = H]

The transformation of compounds of formula (VIII) into compounds of formula (XIV) may be achieved by reaction with a suitable nucleophile such as vinyltributyl stannane in the presence of a catalyst such tetrakis(triphenylphosphine) palladium(0) in a solvent such as dioxane or DMF at a temperature of up to 150° C., typically using microwave irradiation. Compounds of formula (Ie) may be prepared from compounds of formula (XIV) following oxidation using a catalyst such as potassium osmate dihydrate with a co-oxidant such as N-methylmopholine-N-oxide in a solvent mixture such as acetone/water at room temperature. Compounds of formula (XV) are thus obtained following cleavage of the diol (Ie) using a suitable reagent such as sodium periodate in an appropriate solvent mixture such as THF/water. Compounds of formula (XVI) may be obtained from compounds of formula (XV) by reduction, typically using a reducing agent such as sodium borohydride in a solvent such as MeOH. Compounds of formula (XVII) may be obtained from compounds of formula (XVI) by bromination. Suitable conditions involve reaction with an appropriate brominating agent such as carbon tetrabromide with triphenyl phosphine in a solvent such as dichloromethane at a temperature of from 0° C. to room temperature. Conversion of compounds of formula (XVI) to the amines of formula (If) can be achieved by reaction with a suitable amine of formula $HNR_3R_3$ in a suitable solvent such as THF or MeCN. Furthermore, where one or both of $R_3$=H, conversion of compounds of formula (If) to compounds of formula (Ig) or compounds of formula (Ih) can be achieved by reaction with a suitably substituted acid chloride ($R_7COCl$) or sulfonyl chloride ($R_7$—$SO_2Cl$), respectively. Suitable conditions for the preparation of compounds of formula (Ig) involve reaction of compounds of formula (If) with an appropriate acid chloride ($R_7COCl$) and an base such as triethylamine in a solvent such as dichloromethane at a temperature of from 0° C. to room temperature. Suitable conditions for the preparation of compounds of formula (Ih) involve reaction of compounds of formula (If) with an appropriate sulfonyl chloride ($R_7$—$SO_2Cl$) in a solvent such as pyridine at a temperature of from 0° C. to 100° C.

In Scheme G it will be apparent to a person skilled in the art that one can start from the racemate (VIII) or from the single enantiomer, which may be obtained using a similar method as for compounds of formula (Ia) starting from compounds of formula (II), according to Scheme C.

It should be clear to the skilled person that the aldehyde (XV) represents a versatile intermediate for further functionalisation as well as for preparation of compounds of formula (If-Ih).

Compounds of formula (Ir-Iv) i.e. compounds of formula (I) wherein $R_1$ is a group —C(O)—V$R_2$, V is oxygen, $R_2$ is a methyl group, A, B and D are CH and $R_5$ can be an amide —C(O)N($R_3$)($R_7$), (Ir), a urea —N($R_3$)C(O)N($R_3$)($R_7$), (Is), a reverse amide —N($R_3$)C(O)$R_7$ (It), a carbamate N($R_3$)C(O)O($R_7$)— or an alcohol —CH(OH)$R_3$, as defined above, may be prepared from compounds of formula (XV) according to Scheme G' below:

(Is) can be achieved by reaction with diphenylphosphoryl azide and a suitable alcohol of formula $R_7$OH (XXVI) in the presence a suitable base such as DIPEA, in suitable solvent mixtures such as toluene/dioxane at temperatures of between 50-100° C. Furthermore, conversion of compounds of formula (XXVI), where $R_7$=$^t$Bu, to compounds of formula (It) can be obtained following removal of the "Boc" protecting group using a suitable acid such as trifluoroacetic in a

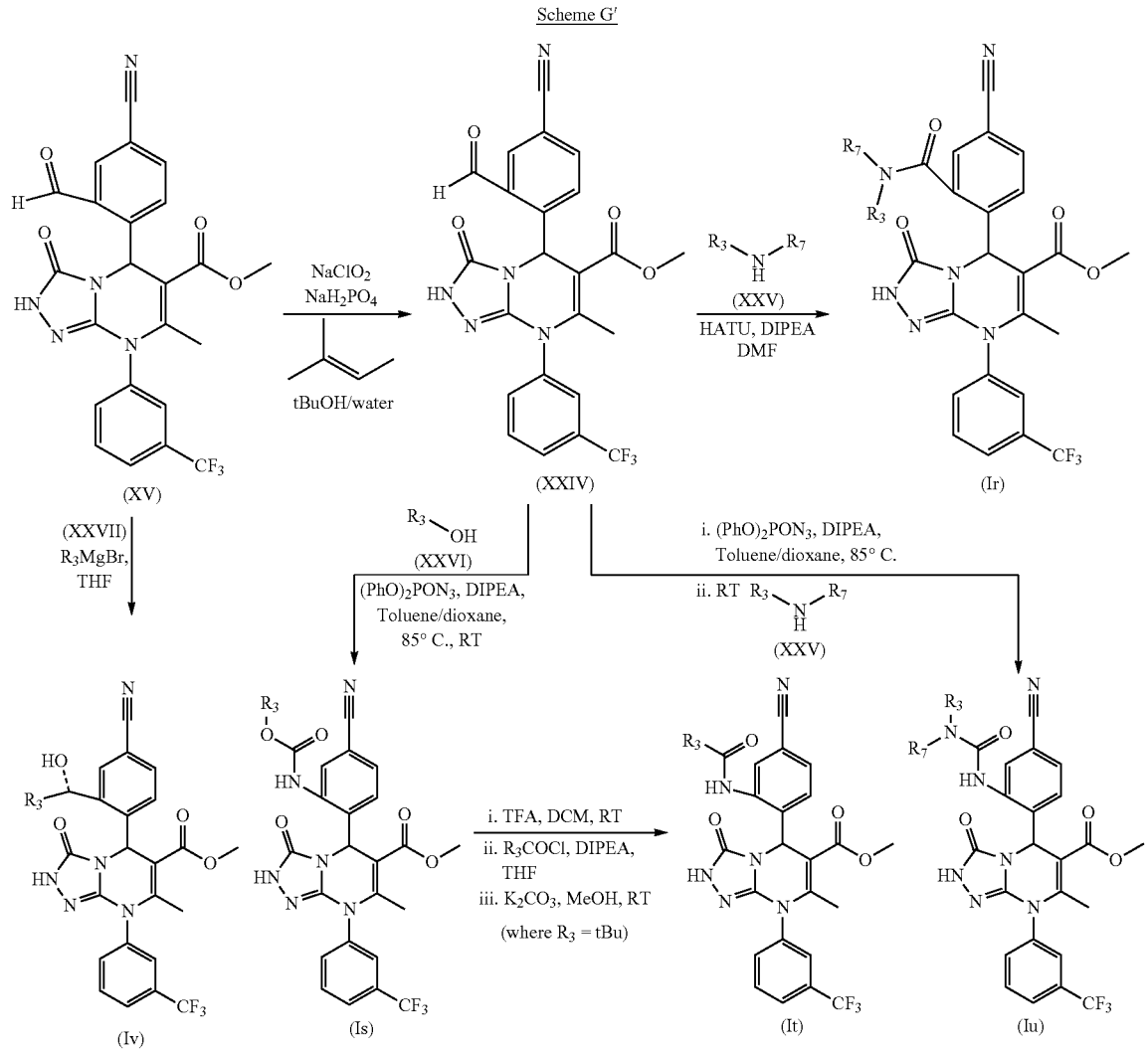

Scheme G'

The transformation of compounds of formula (XV) to compounds of formula (XXIV) may be obtained from compounds of formula (XV) by oxidation, typically using an oxidizing agent such as sodium chlorite in a solvent mixture such as t-butanol and water in the presence of a sacrificial alkene such as 2-methyl-2-butene. Compounds of formula (Ir) may be obtained from compounds of formula (XXIV) following reaction with compounds of formula (XXV). Suitable conditions involve reaction with an appropriate coupling agent such as HATU, in the presence of a suitable base such as DIPEA and in a solvent such as DMF at a temperature of from 0° C. to room temperature. Conversion of compounds of formula (XXIV) to carbamates of formula suitable solvent such as dichloromethane. The intermediate amino compound may be converted into reverse amides of formula (It) following reaction with a suitable acid chloride ($R_3$COCl) in the presence of a suitable base such as DIPEA, in a suitable solvent such as THF. Conversion of compounds of formula (XXIV) to ureas of formula (Iu) can be achieved by reaction with diphenylphosphoryl azide in the presence of a suitable base such as DIPEA in suitable solvent mixtures such as toluene/dioxane, at temperatures of between 50-100° C., followed by reaction with a suitable amine of formula $R_3R_7$NH (XXV) at room temperature.

Compounds of formula (Iv) can be prepared from compounds of formula (XV) following reaction with a suitable Grignard reagent (XXVII) such as methylmagnesium bromide in a suitable solvent such as THF at a temperature of from −78° C. to RT.

In Scheme G' it will be apparent to a person skilled in the art that one can start from the racemate (XV) or from the single enantiomer.

Compounds of formula (Ii-Io) may be prepared according to Scheme H from a compound of formula (VIII). A compound of formula (XIX) may be prepared using Heck coupling chemistry by reaction with an appropriately substituted vinyl compound (XVIII) in the presence of an appropriate catalyst/ligand system such as Herrmann-Beller catalyst/tributylphosphine tetrafluoroborate in a solvent such as tetraethylene glycol or dimethoxyethane in the presence of a base such as pentamethylpiperidine at a temperature of from room temperature to 160° C. A compound of formula (XX) may be prepared from compounds of formula (XIX) following hydrolysis and reduction steps using an acid such as trifluoroacetic acid in a solvent such as DCM at −10° C. to give the intermediate aldehyde, and a reducing agent such as sodium borohydride in a solvent such as MeOH at a temperature of from 0° C. to room temperature to give a compound of formula (XX). A compound of formula (XX) can be prepared from a compound of formula (XIX) using a mixture of carbon tetrabromide/triphenyl phosphine in a solvent such as DCM at a temperature of from 0° C. to 50° C. Compounds of the formula (Ii-Ik) may be prepared similarly to those described for compounds of formula (If-Ih) (Scheme G), using compounds of formula (XXI).

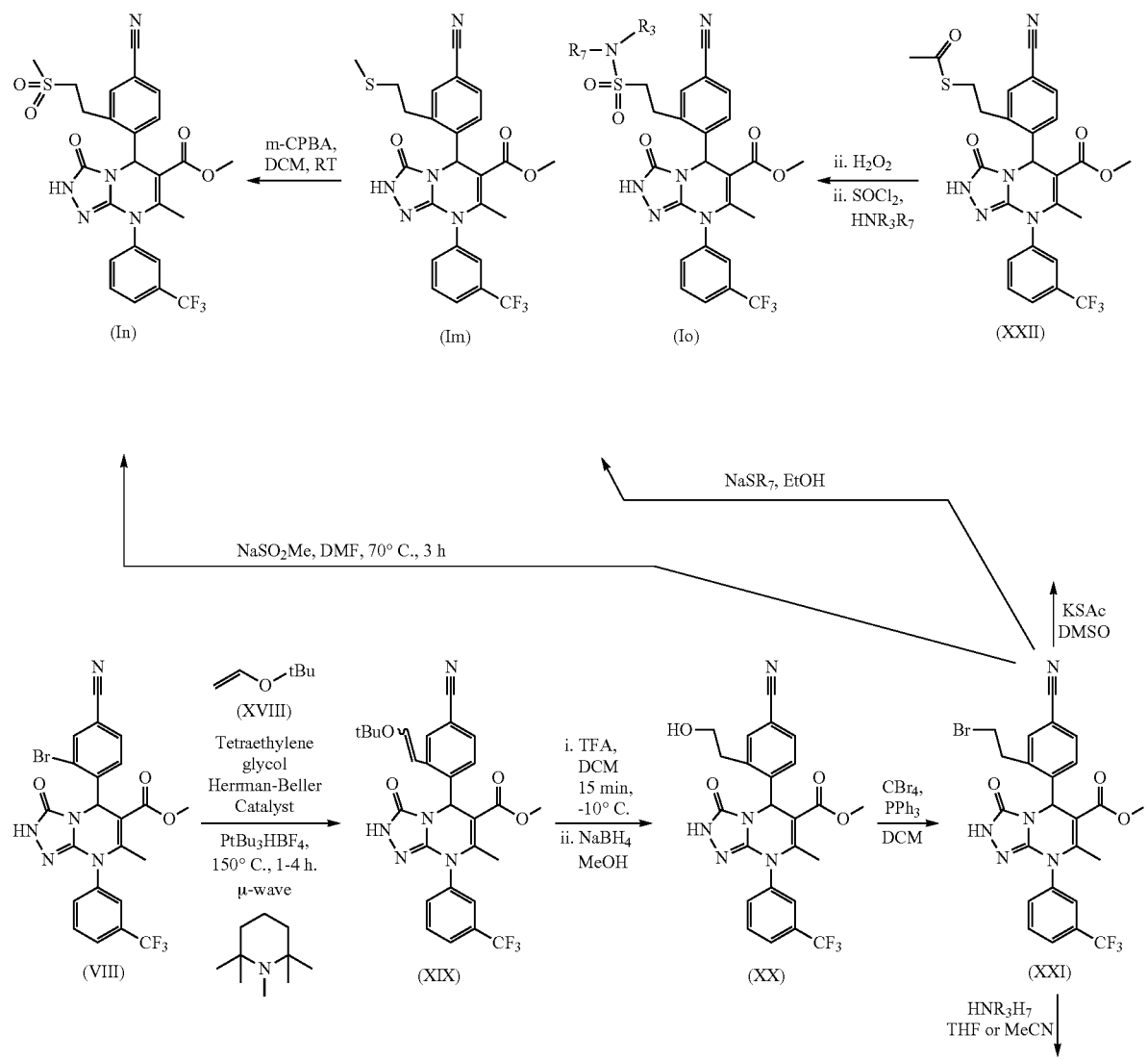

Scheme H

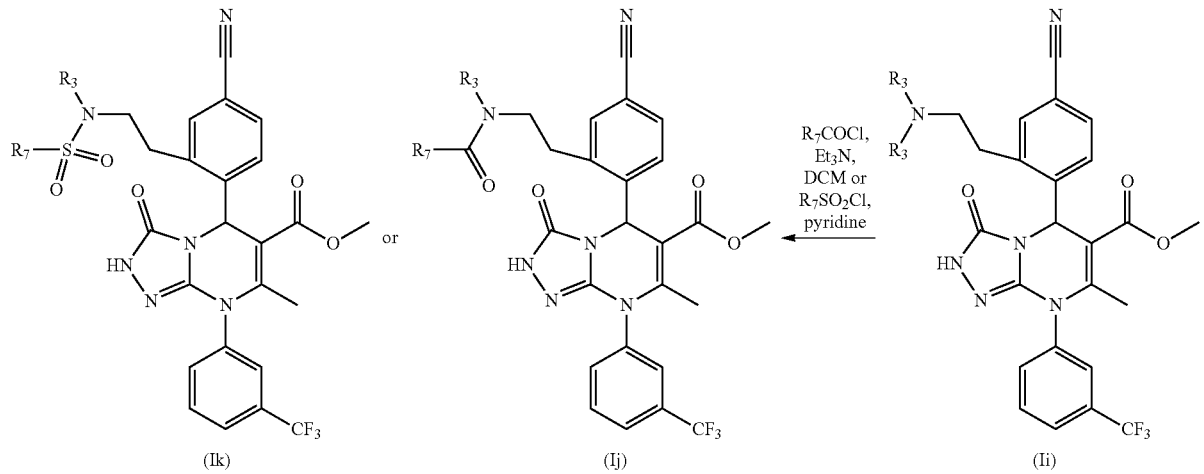

[Where one R₃ or R₇ = H]

Compounds of formula (Im) may also be prepared from compounds of formula (XXI) using a suitable thiolate (NaSR₇) in a suitable solvent such as ethanol at a temperature of from 0° C. to room temperature to give a compound of formula (Im). Compounds of formula (In) may be prepared from compounds of formula (Im) using a suitable oxidizing agent such as m-chlorobenzoic acid in a suitable solvent such as dichloromethane at a temperature of from 0° C. to room temperature to give a compound of formula (In). Compounds of formula (In) or compounds of the invention (I) wherein R₁ is defined as CN, can also be prepared directly from compounds of formula (XXI) or similar (wherein R₁ is defined as CN) following reaction with a suitable sulfinate salt such as sodium methanesulfonate in a suitable solvent such as DMF at temperatures of from RT to 100° C.

Furthermore, compounds of formula (Io) may also be prepared from compounds of formula (XXI) using KSAc in a suitable solvent such as DMSO at a temperature of from 0° C. to room temperature to give a compound of formula (XXII). Compounds of formula (Io) can be prepared from compounds of formula (XXII) following oxidation with a suitable oxidizing agent such as hydrogen peroxide followed by chlorination with a suitable chlorinating agent such as thionyl chloride followed by reaction of the intermediate sulfonyl chloride with an amine compound of the invention (HNR₃R₇).

In Scheme H it will be apparent to a person skilled in the art that one can start from the racemate (VIII) or from the single enantiomer.

Compounds of the formula (Iw-Iy) may be prepared from compounds of formula (VIII). Compounds of formula (XXVIII) can be prepared from compounds of formula (VIII) using Heck coupling chemistry by reaction with an appropriately substituted vinyl compound such as allyl alcohol in the presence of an appropriate catalyst/ligand system such as tris(dibenzylideneacetone)dipalladium(0)/tributylphosphine tetrafluoroborate in a solvent such as dioxane in the presence of a base such as N,N-dicyclohexylmethylamine at a temperature of from room temperature to 100° C. A compound of formula (XXIX) may be prepared from compounds of formula (XXVIII) following reduction using a reducing agent such as sodium borohydride in a solvent such as MeOH at a temperature of from 0° C. to room temperature to give a compound of formula (XXIX). A compound of formula (XXX) can be prepared from a compound of formula (XXIX) using a mixture of carbon tetrabromide/triphenyl phosphine in a solvent such as DCM at a temperature of from 0° C. to 50° C.

In Scheme H' it will be apparent to a person skilled in the art that one can start from the racemate (VIII) or from the single enantiomer.

Compounds of the formula (Iw-Iy) may be prepared similarly to those described for compounds of formula (If-Ih) (Scheme G), using compounds of formula (XXX).

Scheme H'

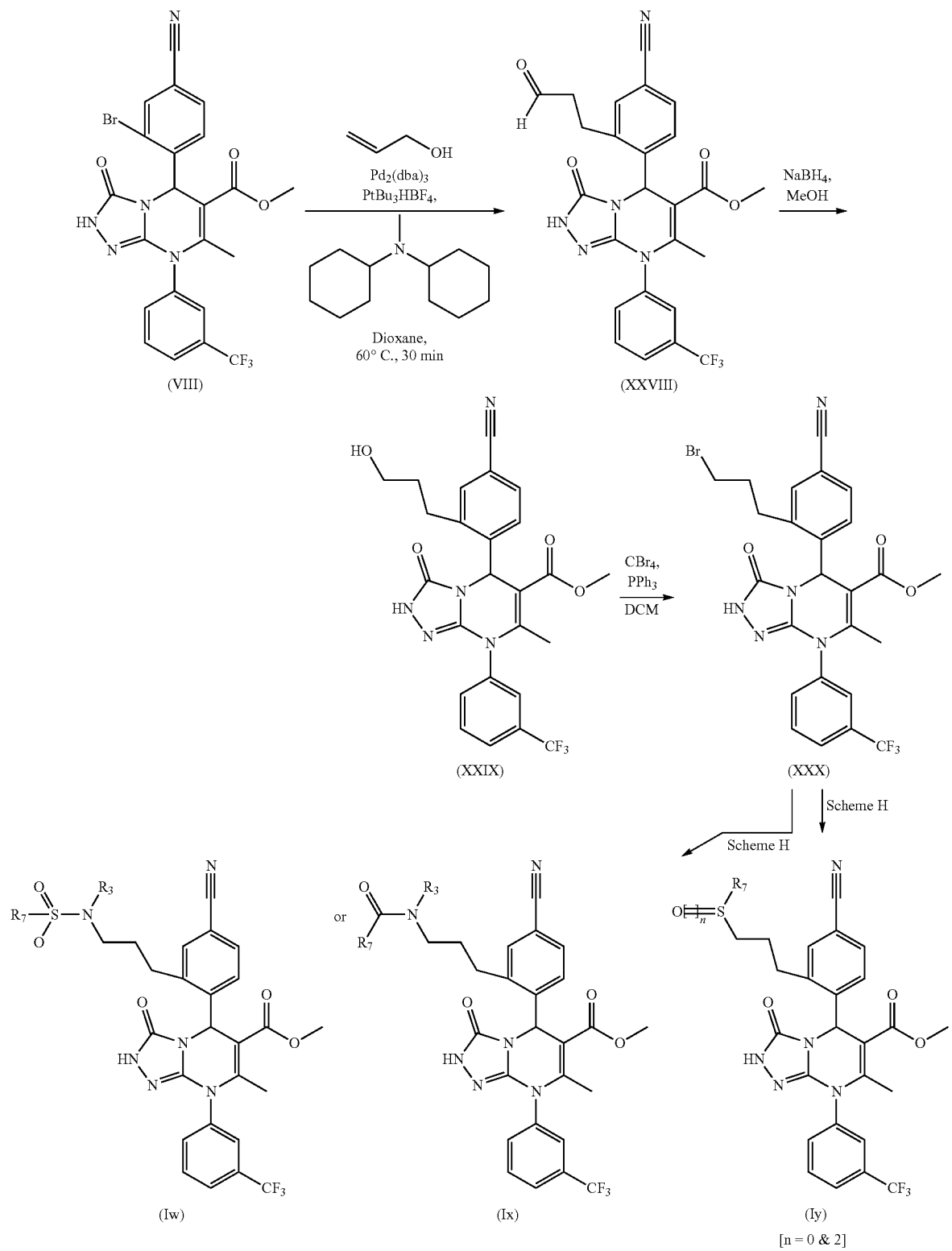

Compounds of formula (Ip), i.e. compounds of formula (I) wherein $R_1$ is a group —C(O)—V$R_2$, A, B and D are CH, V is oxygen, $R_2$ is a methyl group, and $R_5$ is an amide-linked group as reported in Scheme J where $R_3$ and $R_7$ may have different meanings according to those described for compounds of formula (I), may be prepared from compounds of formula (XX) according to Scheme J below:

Scheme J

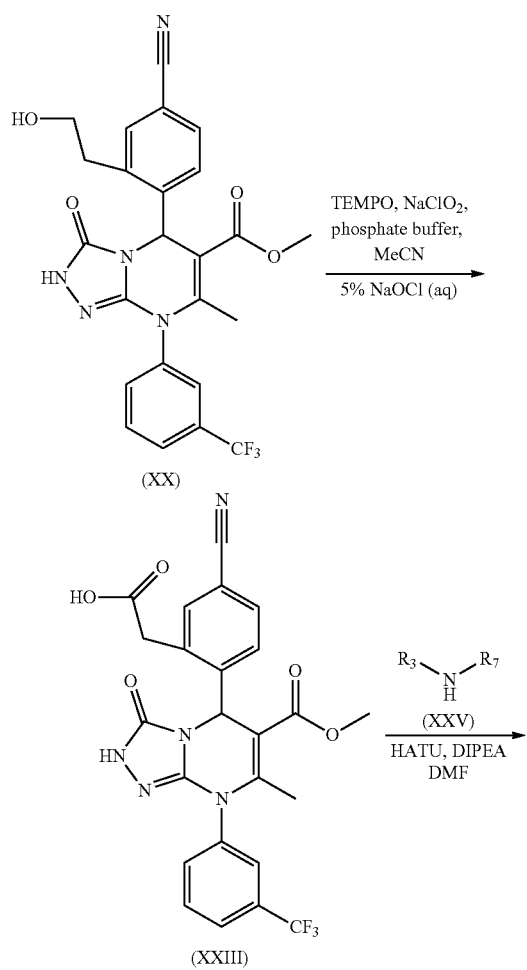

Compounds of formula (XXIII) may be prepared from compounds of formula (XX) using suitable oxidizing reagent agent such as sodium chlorite and an appropriate co-oxidant such as TEMPO in a suitable solvent mixture such as acetonitrile/water and using an appropriate base such as sodium dihydrogenphosphate at room temperature. Typically, compounds of formula (Ip) may be obtained from compounds of formula (XXIII) by reaction with an amine (XXV) in the presence of a coupling agent such as HATU in a solvent such as DMF in the presence of a base such as triethylamine at a temperature of from room temperature to 80° C.

In Scheme J it will be apparent to a person skilled in the art that one can start from the racemate (XX) or from the single enantiomer.

Alternatively, compounds of formula (Ip) can be prepared from compounds of formula (VIII) according to Scheme J' below.

Scheme J'

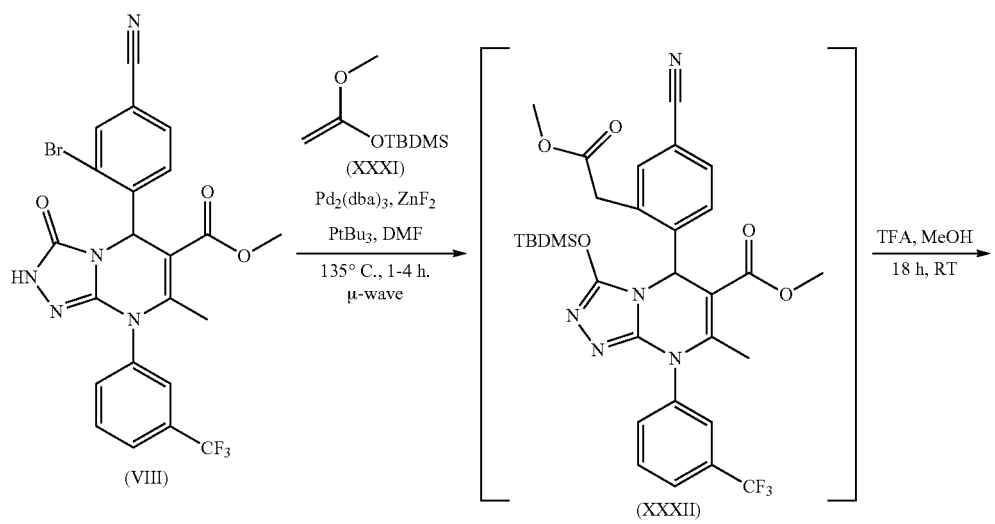

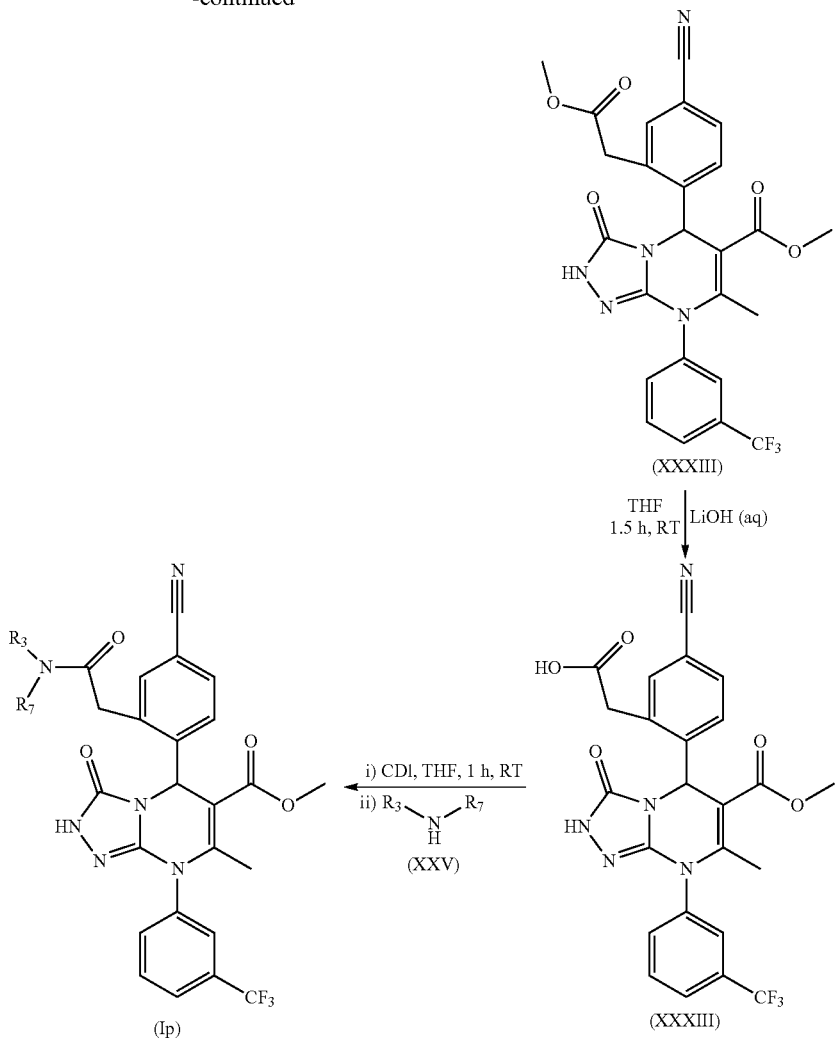

Compounds of formula (XXXII) may be prepared from compounds of formula (VIII) using a palladium-mediated cross-coupling reaction with 1-(tert-butyldimethylsilyloxy)-1-methoxyethene (XXXI) and an appropriate fluoride ligand such as $ZnF_2$ in a suitable solvent such as DMF. A suitable palladium catalyst may be formed by using palladium(0)bis (dibenzylideneacetone) with the tri(tert-butyl)phosphine ligand. The intermediate compound (XXXII) can be hydrolyzed to a compound of formula (XXXIII) typically using a mixture of an acid such as trifluoroacetic acid in a protic solvent such as methanol. Compounds of formula (XXIII) may be obtained from compounds of formula (XXXIII) by hydrolysis with a suitable base such as lithium hydroxide in a mixture of solvents such as THF and water at room temperature. Compounds of formula (Ip) may be obtained from compounds of formula (XXIII) by reaction with an amine (XXV) in the presence of a coupling agent such as 1,1'-carbonyldiimidazole (CDI) in a solvent such as DMF in the presence of a base such as triethylamine at a temperature of from room temperature to 80° C.

In Scheme J' it will be apparent to a person skilled in the art that one can start from the racemate (VIII) or from the single enantiomer.

Furthermore, it should be clear to the skilled person that an appropriate protecting group strategy may be contemplated at the triazolinone moiety, and that the incorporation of a suitable protecting group can be possible at any intervening step in the synthesis of compounds of the invention, (Ia-Iy).

The skilled person may introduce, where appropriate, suitable variations to the conditions specifically described in the examples below in order to adapt the synthetic routes to the provision of further compounds of the invention. Such variations may include, but are not limited to, use of appropriate starting materials to generate different compounds, changes in the solvent and temperature of reactions, replacement of reagents and/or starting materials with analogous chemical role, introduction or removal of protection/de-protection stages of functional groups sensitive to reaction conditions and reagents, as well as introduction or removal of specific synthetic steps oriented to further functionalization of the chemical scaffold.

Processes which can be used and are described and reported in Examples should not be viewed as limiting the scope of the synthetic methods available for the preparation of the compounds of the invention.

Compounds used as starting materials or intermediates may be commercially available, their preparation may be specifically described in the literature, or they may be prepared according to methods available in the literature and well known to the person skilled in the art.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form. In particular, functional groups present in the Intermediates and Examples and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1981), which is incorporated herein by reference in its entirety).

Likewise, selective protection and de-protection of any of the said groups, for instance including carbonyl, hydroxyl or amino groups, may be accomplished according to very well-known methods commonly employed in organic synthetic chemistry.

Optional salt formation of the compounds of formula (I) may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

The diastereoisomers of compounds of formula (I), where available, may be obtained according to methods well known in the art, such as for example by preparative HPLC or by chromatographic purifications. A racemic mixture of compounds of formula (I) may as well be separated using preparative HPLC and a column with a chiral stationary phase, or resolved to yield individual enantiomers using methods well known in the art. Furthermore, chiral intermediates may be resolved and used to prepare chiral compounds of the invention.

From all of the above, it should be clear to the skilled person that the above process, comprehensive of any variant thereof for the preparation of suitable compounds of the invention, may be conveniently modified so as to adapt the reaction conditions to the specific needs, for instance by choosing appropriate condensing agents, solvents and protective groups, as the case may be.

Other features of the invention will become apparent in the course of the following descriptions of exemplary embodiments which are given for illustration of the invention and are not intended to be limiting thereof

EXAMPLES

General Experimental Details

Reactions were not carried out under an inert atmosphere unless specified and all solvents and commercial reagents were used as received.

Purification by chromatography refers to purification using the CombiFlash® Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 µm and nominal 60 Å porosity. Fractions containing the required product (identified by TLC and/or LCMS analysis) were pooled, the organic fraction removed by evaporation, and the remaining aqueous fraction lyophilized, to give the final product. Where thin layer chromatography (TLC) has been used, it refers to silica gel TLC using plates, typically 3×6 cm silica gel on aluminum foil plates with a fluorescent indicator (254 nm), (e.g. Fluka 60778). Microwave experiments were carried out using a Biotage Initiator 60™ which uses a single-mode resonator and dynamic field tuning. Temperature from 40-250° C. can be achieved, and pressures of up to 30 bar can be reached.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Compound names were generated using the Autonom 2000 feature in MDL ISIS™/Draw 2.5 SP2 software.

Analytical LC-MS Conditions.

LC-MS Method 1.

The Waters ZQ quadrupole mass spectrometer with a C18-reverse-phase column (30×4.6 mm Phenomenex Luna 3 µm particle size), elution with A: water+0.1% formic acid; B: MeCN+0.1% formic acid. Gradient:

| Gradient - Time | flow (mL/min) | % A | % B |
| --- | --- | --- | --- |
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (200 µl/min split to the ESI source with in-line HP1100 PDA detector)

MS ionization method—Electrospray (positive and negative ion)

LC-MS Method 2.

Waters Micromass ZMD quadrupole mass spectrometer with a C18-reverse-phase column (30×4.6 mm Phenomenex Luna 3 µm particle size), elution with A: water+0.1% formic acid; B: MeCN+0.1% formic acid. Gradient:

| Gradient - Time | flow (mL/min) | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection— MS, ELS, UV (100 µl split to MS with in-line UV detector)

MS ionization method—Electrospray (positive and negative ion)

LC-MS Method 3.

Waters Micromass ZQ2000 mass spectrometer with a C18-reverse-phase column (100×2.1 mm Acquity BEH with 1.7 μm particle size) maintained at 40° C., elution with A: water+0.1% formic acid; B: MeCN+0.1% formic acid. Alternatively, where specified, a C18-reverse-phase (100× 2.1 mm Acquity UPLC BEH Shield 1.7 μm particle size) column was used.

Gradient:

| Gradient - Time | flow (mL/min) | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA

MS ionization method—Electrospray (positive/negative ion).

LC-MS Method 4.

Waters Platform LC quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow (mL/min) | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (Split—200 μl/min split to the ESI source with in-line HP 1100 DAD detection)

MS ionization method—Electrospray (positive and negative ion).

LC-MS Method 5.

Waters VG Platform II quadrupole spectrometer with a C18-reverse-phase column (30×4.6 mm Luna 3 μm particle size), elution with A: water+0.1% formic acid; B: MeCN+ 0.1% formic acid.

Gradient:

| Gradient - Time | flow | % A | % B |
| --- | --- | --- | --- |
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (Split—200 μl/min split to the ESI source with in-line HP1050 DAD detection)

MS ionization method—Electrospray (positive and negative ion)

MDAP System:

Instrumentation: Agilent 1260 infinity purifications system. Agilent 6100 series single Quadrupole LC/MS Column: XSELECT CSH Prep C18 5 μm OBD, 30×150 mm, RT Mobile Phase A: 0.1% aqueous formic acid Mobile Phase B: 0.1% formic acid in acetonitrile Flow: 60 ml/min Gradient Program: 10%-95%, 22 min, centered around a specific focused gradient Sample Injection of a 20-60 mg/ml solution in DMSO (+ optional formic acid and water).

ABBREVIATIONS USED IN THE EXPERIMENTAL SECTION

AIBN Azobisisobutyronitrile
CDI 1,1'-Carbonyldiimidazole
DCM Dichloromethane
DIPEA Di-isopropylethylamine
DMF N,N-dimethylformamide
DMSO Dimethylsulphoxide
$Et_2O$ Diethyl ether
EtOAc Ethyl acetate
HATU (1-[Bis(dimethylamino)methylene]-1H-1,2,3-triazolo[4,5-b]pyridinium 3-oxid hexafluorophosphate)
HPLC High performance liquid chromatography
IMS Industrial methylated spirits
LC-MS Liquid chromatography-mass spectrometry
MeCN Acetonitrile
MDAP Mass Directed Automatic Purification
NBS N-Bromosuccinimide
Rt Retention time
RT Room temperature
THF Tetrahydrofuran In the procedures that follow, some of the starting materials are identified through an "Intermediate" or "Example" number. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Examples 1a/1 b

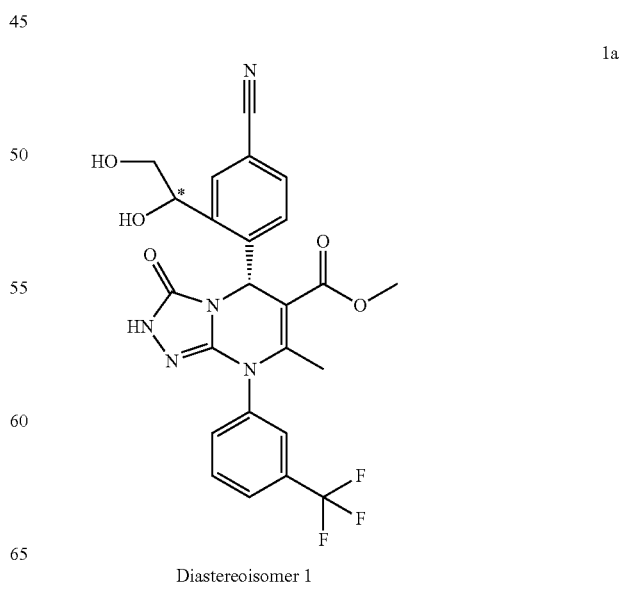

Diastereoisomer 1

1a

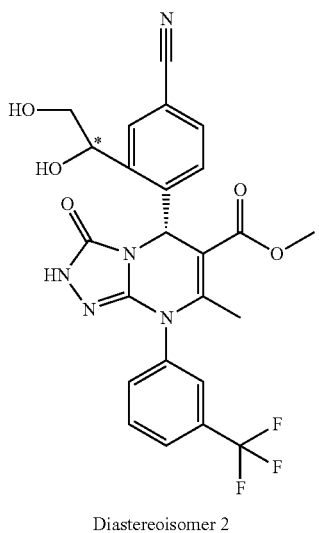

Diastereoisomer 2

(R)-5-[4-Cyano-2-(1,2-dihydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester (diastereoisomers 1a and 1 b)

Intermediate 1

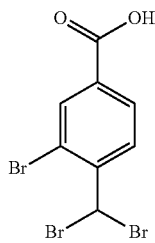

3-Bromo-4-dibromomethylbenzoic acid

3-Bromo-4-methylbenzoic acid (910 g, 4.23 mol, 1.0 eq.) and NBS (2010 g, 11.29 mol, 2.67 eq.) were dissolved in DCM (8.5 L) in a 20 L flange flask fitted with a mechanical stirrer. A slurry of AIBN (50 g, 0.3 mol, 0.07 eq.) in DCM (1 L) was then added, and the mixture irradiated under strong light (500 W) under a reflux condenser under an $N_2$ atmosphere. The internal temperature of the reaction rose from 17° C. to 41° C. and the initial white suspension became a pale orange suspension as it reached gentle reflux. After a total of 72 h. the reaction was complete and water (5 L) was added to the cloudy orange solution, which was stirred at RT for 1 h. The orange biphasic mixture was then left to stand overnight and was then concentrated in vacuo to give an orange distillate and a tan suspended solid. The solid was then collected by filtration, washed with water (2 L) and suction dried for 2 h to give the title compound as a tan coloured damp solid (1860 g).

LCMS (Method 1): Rt=3.39 min, m/z 369, 371, 373, 375 [M−H]

$^1$H NMR (300 MHz, d$_6$-DMSO): δ8.14-8.03 (3H, m), 7.36 (1H, s).

Intermediate 2

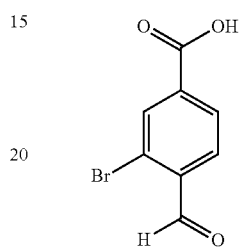

3-Bromo-4-formylbenzoic acid

Intermediate 1 (1860 g, 4.23 mol, 1.0 eq.) was suspended in water (5 L) and the slurry was heated to an internal temperature of 40° C. Solid Na$_2$CO$_3$ (1460 g, 13.77 mol, 3.25 eq.) was then added in small portions over a period of 20 min. Foaming resulted on initial addition, so EtOAc (0.2 L) was added to collapse the foam and suppress any further foaming. Once addition was complete, the brown suspension was heated to 90° C. over 40 min, then stirred at 90° C. for 90 min, then cooled to 40° C. over 90 min. EtOAc (1.5 L) was added, followed by addition of aqueous concentrated HCl via dropping funnel (0.7 L), resulting in vigorous evolution of CO$_2$ gas and evaporation of most of the EtOAc. Further EtOAc (1 L) was added to wash the foaming product from the condenser and the walls of the reactor, then additional EtOAc (0.3 L) was added and the thick slurry was stirred at RT overnight. The slurry was then heated to 40° C. and further aqueous concentrated HCl was added via dropping funnel with vigorous stirring over 45 min, resulting in CO$_2$ gas evolution, evaporation of most of the EtOAc and formation of a solid. Stirring was ceased, and the solid floated to the top of the aqueous mixture (pH 1). The majority of the aqueous layer was separated (ca. 5 L) and then 2-MeTHF (5 L) was added. The clear aqueous layer was then removed, and the organic layer diluted to 10 L with additional 2-MeTHF, and warmed to 50° C. to give a dark orange solution. The organic layer was then washed with 1 M HCl (0.5 L), evaporated, and azeotroped with toluene to afford the title compound as a tan coloured solid (960.3 g).

LCMS (Method 4): Rt 2.73 min, m/z 227 [M($^{79}$Br)+H]$^+$ $^1$H NMR (300 MHz, d$_6$-DMSO): δ10.26 (1H, d, J=0.8 Hz), 8.20 (1H, d, J=1.5 Hz), 8.08-8.04 (1H, m), 7.95 (1H, d, J=8.0 Hz).

Intermediate 3

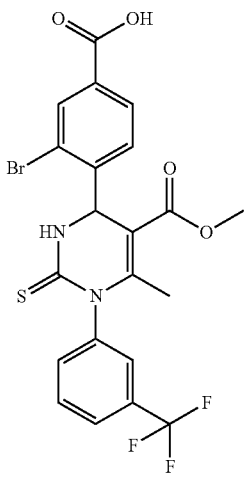 [SMILES: COC(=O)C1=C(C)N(c2cccc(C(F)(F)F)c2)C(=S)NC1c1ccc(C(=O)O)cc1Br]

4-(2-Bromo-4-carboxyphenyl)-6-methyl-2-thioxo-1-(3-trifluoromethylphenyl)-1,2,3,4-tetrahydropyrimidine-5-carboxylic acid methyl ester Intermediate 2 (458 g, 2 mol, 1.0 eq.), methyl acetoacetate (274.4 g, 255 mL, 2.36 mol, 1.18 eq.) and 3-trifluoromethylphenyl thiourea (519 g, 2.36 mol, 1.18 eq.), were charged to a 10 L jacketed reactor under a $N_2$ atmosphere, and suspended in THF (4.6 L) and while stirring, was cooled to −10° C. (internal temperature −3° C.). Polyphosphoric acid (1650 g, 3.6 wt eq.), was prewarmed in a water bath at 50° C., then added in one portion, resulting in an immediate exotherm, and the internal temperature rose to 19° C. The resulting orange mixture was then warmed to 75° C. in 10° C. increments to a gentle reflux, and the reaction stirred at this temperature for 20 h. The reaction was then cooled to 20° C. and the bulk of THF removed in vacuo to give a dark orange viscous oil, which was then diluted with water (5 L) and $Et_2O$ (5 L). The aqueous layer was separated and extracted again with $Et_2O$ (2×2 L) and the combined organics were subsequently washed with water (1 L), brine (1 L) and dried ($Na_2SO_4$) and filtered through Celite to remove any fine particulates. The filtered solution was then concentrated in vacuo to give a viscous orange gum which was resuspended in $Et_2O$ (ca. 1.5 L) and left to stand overnight. The resulting suspension was filtered and the solid collected was rinsed with $Et_2O$ (0.5 L) and dried in a vacuum oven at 50° C. (8 mbar) for 4 days to afford the title compound (754 g).

LCMS (Method 1): Rt 3.52 min, m/z 529 [M($^{79}$Br)+H]$^+$ $^1$H NMR (300 MHz, $d_6$-DMSO): δ10.15 (1H, d, J=3.5 Hz), 8.11 (1H, d, J=1.6 Hz), 8.05 (1H, dd, J=8.1, 1.7 Hz), 7.92-7.64 (5H, m), 5.80 (1H, d, J=2.9 Hz), 3.53 (3H, s), 2.07 (3H, s).

Intermediate 4

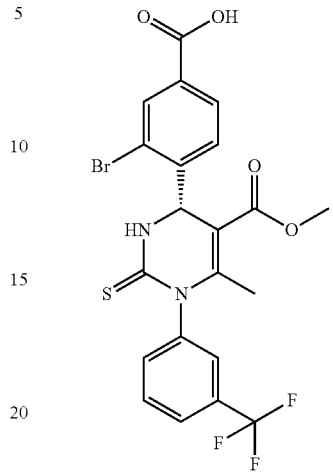

(S)-4-(2-Bromo-4-carboxy-phenyl)-6-methyl-2-thioxo-1-(3-trifluoromethyl-phenyl)-1,2,3,4-tetrahydro-pyrimidine-5-carboxylic acid methyl ester Intermediate 3 (151.7 g, 0.29 mol, 1.0 eq.) was dissolved in dioxane (2 L) and heated to 80° C. The resulting suspension was filtered to remove any inorganic residues and the clear solution was again heated to 80° C. and (+)-Cinchonine (88 g, 0.29 mol, 1.0 eq,) was added, resulting in a clear solution. The resultant mixture was allowed to cool slowly and crystallise. After 3 h, the resulting solid was filtered and washed with cold dioxane. The solid was resuspended in hot dioxane (85° C.) and allowed to cool and crystallise overnight. The resulting crystals were filtered off, washed with cold dioxane, and the solid recrystallised again from hot dioxane. The final recrystallization solids were filtered off and air-dried to give the intermediate (+)-Cinchonine salt as a white solid 83.2 g (68%).

The optical purity of the resolved (+)-Cinchonine salt was determined by partitioning between 1 M HCl and EtOAc; the organic layer was separated, concentrated in vacuo and then redissolved in 20% IPA/n-heptane with 0.1% TFA and subjected to chiral analytical HPLC (ChiralPak IA, 5 μM 4.6×250 mm), eluting with 20% IPA/n-heptane (+0.1% TFA) at 1 mL/min and a wavelength of 254 nm. The racemic product was also checked by chiral HPLC; Retention times of 14.8 and 42.5 mins were observed for a racemic sample and the desired enantiomer was eluted at 42.5 mins and was found to be greater than 99.5 ee %.

The intermediate (+)-Cinchonine salt (83.2 g, 101.75 mmol) was liberated by partitioning between EtOAc (1 L) and 1 M HCl (1 L). The aqueous layer was extracted again with EtOAc (2×0.5 L) and the combined organic layers washed with 1 M HCl (0.5 L), then brine (0.25 L), dried ($Na_2SO_4$) and concentrated in vacuo to give the title compound as a white solid (45.45 g).

Intermediate 5

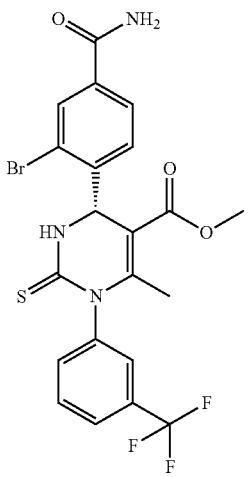 [SMILES: COC(=O)C1=C(C)N(c2cccc(C(F)(F)F)c2)C(=S)N[C@@H]1c1ccc(C(=O)O)cc1Br]

(S)-4-(2-Bromo-4-carbamoyl-phenyl)-6-methyl-2-thioxo-1-(3-trifluoromethyl-phenyl)-1,2,3,4-tetra-hydro-pyrimidine-5-carboxylic acid methyl ester Intermediate 4 (93.8 g, 0.18 mol) was dissolved in THF (1 L) and 1,1'-carbonyldiimidazole (57.5 g, 0.35 mol, 2.0 eq.) was added portion-wise and left to stir at RT until gas evolution had ceased. Aqueous ammonia solution (33%, 330 mL) was then added drop-wise, ensuring the internal temperature did not exceed 10° C. (exotherm observed on initial addition). The reaction was left to stir at RT for 2 h, then brine was added and the layers were separated. The organic phase was washed with aqueous 1 M HCl (2×) and the acidic layer further extracted with EtOAc. The combined organic layers were washed with brine, dried (Na$_2$SO$_4$), filtered and concentrated in vacuo to afford the title compound as a colourless foam (87.3 g).

LCMS (Method 2): Rt 3.44 min, m/z 528 [M($^{79}$Br)+H]$^+$ $^1$H NMR (300 MHz, d$_6$-DMSO): δ10.12 (1H, d, J=2.6 Hz), 8.12 (1H, s), 8.11 (1H, d, J=1.7 Hz), 7.96 (1H, dd, J=8.1, 1.7 Hz), 7.88-7.77 (2H, m), 7.75-7.63 (3H, m), 7.54 (1H, s), 5.78 (1H, s), 3.54 (3H, s), 2.07 (3H, s).

Intermediate 6

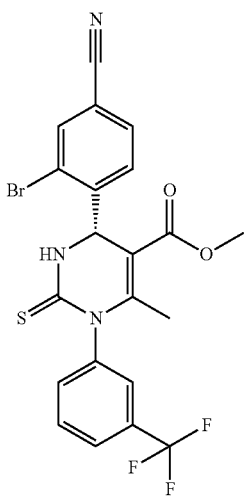 [SMILES: COC(=O)C1=C(C)N(c2cccc(C(F)(F)F)c2)C(=S)N[C@@H]1c1ccc(C#N)cc1Br]

(S)-4-(2-Bromo-4-cyanophenyl)-6-methyl-2-thioxo-1-(3-trifluoromethylphenyl)-1,2,3,4-tetrahydropyrimidine-5-carboxylic acid methyl ester Intermediate 5 (87.3 g, 0.165 mol) was dissolved in DMF (400 mL) and cooled to 0-5° C. in an ice bath. Phosphorous oxychloride (62.0 g, 37.0 mL, 2.5 eq.) was then added drop-wise, ensuring the internal temperature did not exceed 10° C. Once addition was complete, the yellow solution was stirred at 0-5° C. for 15 min, then poured into a mixture of solid 2 M Na$_2$CO$_3$ and ice. A yellow precipitate formed and the slurry was aged for 1 h, then the solid was filtered, washed with water and dried in a vacuum oven over P$_2$O$_5$ at 40-45° C. NMR analysis of the resultant product still showed starting material remaining so the reaction was repeated again using a further 20 mL phosphorous oxychloride. NMR of the resulting solid showed the product to be an adduct with POCl$_3$. Therefore, the solid was dissolved in absolute EtOH (1000 mL) and the suspension warmed to aid dissolution. Saturated aqueous NaHCO$_3$ solution (250 mL) was then added and the mixture was heated to 40° C. and stirred for 2 h. The resultant mixture was then poured into water (500 mL) and the resulting white solid filtered off, washed with water and air dried to afford the title compound (77.5 g).

LCMS (Method 2): Rt 3.94 min, m/z 510 [M($^{79}$Br)+H]$^+$ $^1$H NMR (300 MHz, d$_6$-DMSO): δ10.18 (1H, d, J=2.7 Hz), 8.24 (1H, d, J=1.5 Hz), 7.96 (1H, dd, J=8.0, 1.6 Hz), 7.89-7.76 (3H, m), 7.74-7.64 (2H, m), 5.8 (1H, s), 3.53 (3H, s), 2.06 (3H, s).

Intermediate 7

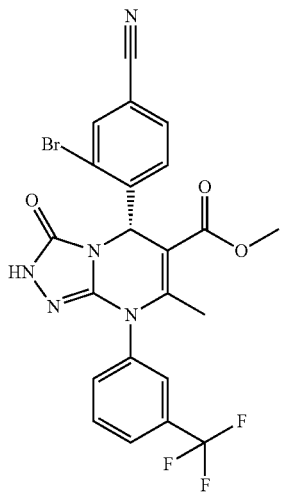 [SMILES: COC(=O)C1=C(C)N(c2cccc(C(F)(F)F)c2)c2n[nH]c(=O)n2[C@@H]1c1ccc(C#N)cc1Br]

(S)-5-(2-Bromo-4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester Intermediate 6 (30.3 g, 59.4 mmol) was dissolved in DCM (500 mL), 2,6-lutidine (19.7 mL, 169 mmol) was added and the solution was cooled to 2° C. While stirring, triphosgene (5.58 g, 18.8 mmol) was then added over a period of 3 min. After 5 min, the reaction was warmed to RT and stirred for 25 min. The reaction was cooled to 2-3° C. and the solution was then transferred via cannula to a cooled (7° C.) mixture of hydrazine solution (1 M in THF, 170 mL) in MeCN (150 mL). The mixture was stirred at 7° C. for a further 5 min. After 2.25 h, the reaction mixture was washed with water, 10% citric acid solution (to remove residual lutidine), water and 50% saturated brine and the organic phase was dried ($Na_2SO_4$), filtered and concentrated in vacuo. Further purification was undertaken by chromatography using silica-gel, and eluting with 40% to 100% EtOAc in cyclohexane to afford Int 7 as a cream coloured solid (17.8 g, 56%)

LCMS (Method 3): Rt 3.61 min, m/z 534 $[M(^{79}Br)+H]^+$ $^1$H NMR (300 MHz, $CDCl_3$): δ8.36 (1H, s), 7.88 (1H, d, J=1.5 Hz), 7.83-7.79 (1H, m), 7.73 (1H, t, J=8.0 Hz), 7.65-7.60 (2H, m), 7.59-7.50 (2H, m), 6.39 (1H, d, J=1.0 Hz), 3.62 (3H, s), 2.25 (3H, d, J=1.0 Hz).

The chiral purity was analysed by Chiralpak IC chiral HPLC column (5 μm particle size, 5% MeOH/DCM, flow rate 5 mL/min) and gave Rt=5.83 min. (100% ee). A racemic sample (Intermediate 4) gave Rt for first and second eluting enantiomers of 3.58 and 5.85 min, respectively.

Intermediate 8

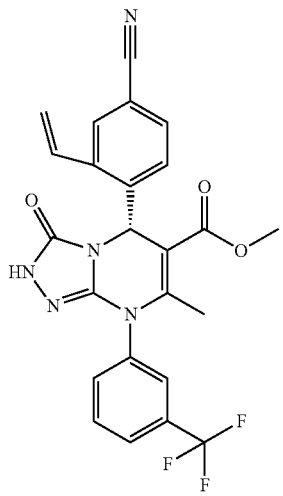 [SMILES: C=Cc1cc(C#N)ccc1[C@@H]1C(C(=O)OC)=C(C)N(c2cccc(C(F)(F)F)c2)c2n[nH]c(=O)n21]

(R)-5-(4-Cyano-2-vinyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 7 (9.0 g, 16.84 mmol) and tributyl vinyl stannane (6.08 g, 18.60 mmol) were dissolved in diglyme (50 mL) and the resulting solution was evacuated and purged with $N_2$ (5 times). Palladium-tetrakis(triphenylphosphine) (0.58 g, 0.50 mmol) was then added, and the reaction mixture was then heated at 150° C. (on a pre-heated block) for 2 h under argon. The reaction mixture was cooled, concentrated in vacuo, diluted with EtOAc (150 mL) and water (150 mL) and filtered through a pad of Celite. The organic layer was separated, washed with water followed by brine, dried ($MgSO_4$), concentrated in vacuo and purified by silica gel chromatography eluting with a gradient of 10-70% EtOAc in cyclohexane to yield the title compound as a yellow foam (7.92 g)).

LC-MS (Method 2): Rt=3.52 min, m/z=482 $[M+H]^+$ (R)-5-[4-Cyano-2-(1,2-dihydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester (Example 1a and Example 1b)

Potassium osmate (VI)dihydrate (8 mg, 21.7 μmol) was added to a solution of Intermediate 8 (1.00 g, 2.08 mmol) and N-methyl morpholine N-oxide hydrate (0.56 g, 4.14 mmol) in acetone (10 mL)–water (1 mL) at RT and stirred overnight. Reaction was quenched using aqueous sodium metabisulfite solution, stirred for 2 h, filtered via Celite and solvent removed in vacuo. The resultant residue was purified by chromatography, eluting with 0-6% MeOH in EtOAc to give the racemic product (0.89 g). Purification by MDAP gave the title compounds 1a (414 mg) and 1b (197 mg) as a white solids.

Example 1a

Diastereoisomer 1

LC-MS (Method 3): Rt=3.87 min, m/z=516.0 $[M+H]^+$ $^1$H NMR (400 MHz, $d_6$-DMSO) δ 11.27 (1H, s), 8.13 (1H, bs), 7.97-7.89 (2H, m), 7.87 (1H, d, J=1.8 Hz), 7.81 (1H, t, J=7.8 Hz), 7.71 (1H, dd, J=8.2 and 1.9 Hz), 7.58 (1H, d, J=8.1 Hz), 6.18 (1H, s), 5.43-5.22 (2H, m), 4.82 (1H, bs), 4.14-3.92 (2H, m), 3.55 (3H, s), 2.10 (3H, s).

Example 1b

Diastereoisomer 2

LC-MS (Method 3): Rt=3.97 min, m/z=516.0 $[M+H]^+$ $^1$H NMR (400 MHz, $d_6$-DMSO) δ 11.44 (1H, s), 8.13 (1H, s), 7.96-7.90 (2H, m), 7.89 (1H, d, J=1.7 Hz), 7.82 (1H, t, J=7.9 Hz), 7.75 (1H, dd, J=8.0 and 1.7 Hz), 7.70 (1H, d, J=8.1 Hz), 6.33 (1H, s), 5.50-5.41 (2H, m), 4.92-4.83 (1H, m), 3.76-3.65 (2H, m), 3.50 (3H, s), 2.18 (3H, s).

Example 2

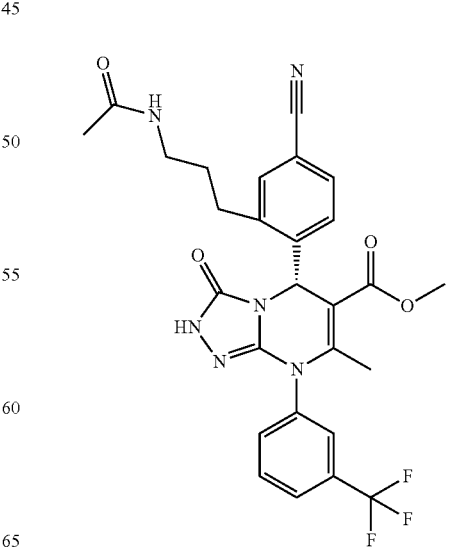

(R)-5-[2-(2-Acetylamino-propyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 9

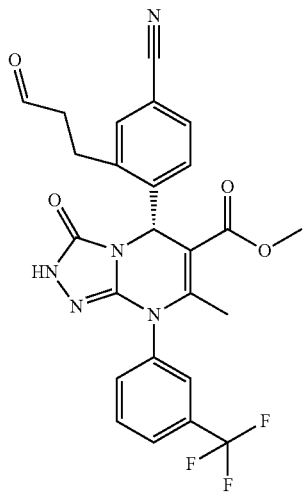 [SMILES: COC(=O)C1=C(C)N(c2cccc(C(F)(F)F)c2)c2n[nH]c(=O)n2[C@@H]1c1ccc(C#N)cc1CCC=O]

(R)-5-[4-Cyano-2-(3-oxo-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester A suspension of tri-tert-butylphosphonium tetrafluoroborate (163 mg, 0.56 mmol) and tris(dibenzylideneacetone)dipalladium(0) in dry dioxane (20 mL) was degassed with argon for 10 mins. To this was added a solution of Intermediate 7 (5.0 g, 9.36 mmol) in dry dioxane (30 mL), followed by allyl alcohol (2.55 mL, 37.43 mmol) and N,N-dicyclohexylmethylamine (4.01 mL, 18.72 mmol). The resulting mixture was stirred at 60° C. for 30 mins then cooled, filtered through Celite and concentrated in vacuo to yield the title compound as a dark yellow foam which was used without further purification (287 mg).

LC-MS (Method 4): Rt=3.32/3.49 min, m/z=512 [M+H]$^+$

Intermediate 10

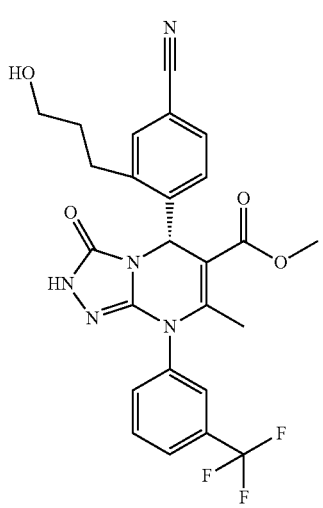 [SMILES: COC(=O)C1=C(C)N(c2cccc(C(F)(F)F)c2)c2n[nH]c(=O)n2[C@@H]1c1ccc(C#N)cc1CCCO]

(R)-5-[4-Cyano-2-(3-hydroxy-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester To a solution of Intermediate 9 (4.30 mmol) in MeOH (40 mL) at 5° C. was added sodium borohydride (163 mg, 4.30 mmol) portion-wise. The mixture was stirred for 30 mins and allowed to warm to RT. The solvent was removed in vacuo and the residue was partitioned between 1 N HCl and EtOAc. The aqueous layer was extracted with EtOAc (×2) and the combined organic extracts dried (Na$_2$SO$_4$) and concentrated in vacuo. The resulting residue was purified by chromatography eluting with a gradient of 0-10% MeOH in DCM to give the title compound as a yellow foam (990 mg).

LC-MS (Method 4): Rt=3.29 min, m/z=514 [M+H]$^+$

Intermediate 11

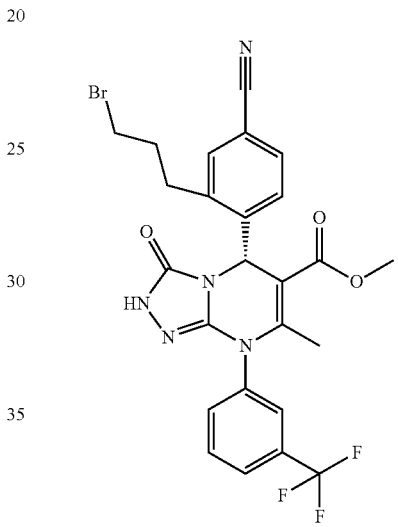

(R)-5-[2-(3-Bromo-propyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester To a solution of intermediate 10 (780 mg, 1.52 mmol) in DCM (20 mL) at 5° C. was added carbon tetrabromide (756 mg, 2.28 mmol) followed by triphenylphosphine (598 mg, 2.28 mmol). The resulting mixture was stirred for 1.5 h and allowed to warm to RT. The solution was diluted with DCM and washed with water and the organic layer dried (Na$_2$SO$_4$) and concentrated in vacuo. The resulting residue was purified by chromatography eluting from 0-50% EtOAc in cyclohexane to give the title compound as a yellow foam (620 mg).

LC-MS (Method 4): Rt=3.90 min, m/z=576 [M($^{79}$Br)+H]$^+$ (R)-5-[2-(2-Acetylamino-propyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester (Example 2)

A solution of Intermediate 11 (205 mg, 0.35 mmol) and ammonia in MeOH (2M, 4 mL, 8.00 mmol) was stirred and heated at 50° C. in a sealed tube overnight. Solvent was removed under a stream of air and the resultant residue re-dissolved in THF (2 mL) and DIPEA (246 μL, 1.42 mmol). A solution of acetyl chloride (74 μL, 1.04 mmol) in THF (1 mL) was added at RT under Argon, stirred for 1 hour and then solvent removed under a stream of air. The resultant residue was dissolved in MeOH (5 mL) and stirred at rt with potassium carbonate (0.12 g, 0.87 mmol). After 1 hour the mixture was added to EtOAc-aqueous HCl and extracted into EtOAc. These extracts were washed with water and brine, dried (MgSO$_4$), filtered and concentrated in vacuo. Purification of the resultant residue by MDAP gave the title compound as a white solid (55 mg).

LC-MS (Method 3): Rt=4.20 min, m/z=555.3 [M+H]$^+$ $^1$H NMR (400 MHz, d$_6$-DMSO) δ 11.19 (1H, bs), 8.11 (1H, s), 7.96-7.89 (3H, m), 7.81 (1H, t, J=7.8 Hz), 7.70-7.60 (3H, m), 6.18 (1H, s), 3.49 (3H, s), 3.25-2.98 (4H, m), 2.14 (3H, s), 2.00-1.84 (2H, m), 1.83 (3H, s).

Example 3

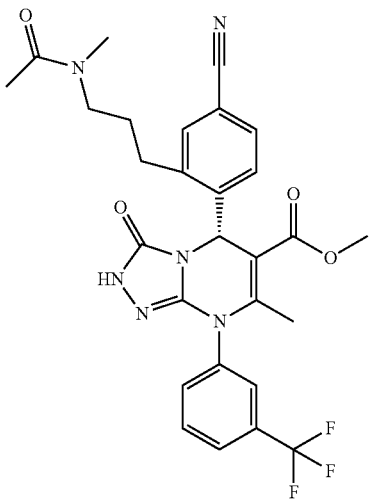 [SMILES: COC(=O)C1=C(C)N(c2cccc(C(F)(F)F)c2)c2n[nH]c(=O)n2[C@@H]1c1ccc(C#N)cc1CCCN(C)C(C)=O]

(R)-5-{2-(3-Acetyl-methyl-amino)-propyl]-4-cyano-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester A solution of Intermediate 11 (200 mg, 0.347 mmol) and methylamine in THF (2M, 1.80 mL, 3.60 mmol) was stirred and heated at 50° C. in a sealed tube overnight. Solvent was removed under a stream of air and the resultant residue re-dissolved in THF (2 mL) and DIPEA (240 μL, 1.39 mmol). A solution of acetyl chloride (75 μL, 1.05 mmol) in THF (1 mL) was added at RT under Argon, stirred for 1 h and then solvent removed under a stream of air. The resultant residue was dissolved in EtOAC, washed with water, aqueous sodium bicarbonate and brine then dried (MgSO$_4$), filtered and concentrated in vacuo. This residue was re-dissolved in MeOH (8 mL) and stirred at rt with potassium carbonate (93 mg, 0.673 mmol). After 2 h the mixture was added to EtOAc-aqueous HCl and extracted into EtOAc. These extracts were washed with water and brine, dried (MgSO$_4$), filtered and concentrated in vacuo. Purification of the resultant residue by MDAP gave the title compound as a white solid (90 mg).

LC-MS (Method 3): Rt=4.27 min, m/z=569.1 [M+H]$^+$ $^1$H NMR (400 MHz, d$_6$-DMSO) δ 11.21-11.15 (1H, m), 8.11 (1H, bs), 7.946-7.86 (2H, m), 7.80 (1H, t, J=7.8 Hz), 7.76-7.60 (3H, m), 6.24-6.19 (1H, m), 3.95-3.71 (1H, m), 3.71-3.61 (1H, m), 3.53-3.47 (3H, m), 3.39-3.14 (2H, m), 3.06-2.90 (3H, m), 2.13 (3H, s), 2.05-2.00 (3H, m).

Example 4

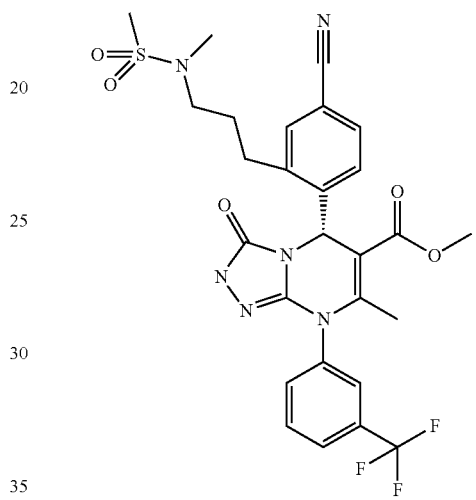

(R)-5-{4-Cyano-2-[3-(methanesulfonyl-1-methyl-amino)-propyl]-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester A solution of Intermediate 11 (250 mg, 0.434 mmol) and methylamine in THF (2M, 2.0 mL, 4.0 mmol) was stirred and heated at 50° C. in a sealed tube overnight. Solvent was removed under a stream of air and the resultant residue re-dissolved in THF (2 mL). This was added to a stirred solution of DIPEA (375 μL, 2.17 mmol) and methanesulfonyl chloride (102 μL, 1.31 mmol) in THF (1.0 mL) at RT under Argon. Solvent was removed under a stream of air after 1 h and the resultant residue dissolved in EtOAc, washed with water, aqueous sodium carbonate and brine then dried (MgSO$_4$), filtered and concentrated in vacuo. Purification of the resultant residue by MDAP gave the title compound as a white solid (106 mg).

LC-MS (Method 3): Rt=4.51 min, m/z=605.1 [M+H]$^+$ $^1$H NMR (400 MHz, d$_6$-DMSO) δ 11.19 (1H, bs), 8.11 (1H, bs), 7.94-7.86 (2H, m), 7.81 (1H, t, J=7.8 Hz), 7.77-7.74 (1H, m), 7.69-7.59 (2H, m), 6.16 (1H, s), 3.51 (3H, s), 3.24-2.91 (4H, m), 2.90 (3H, s), 2.83 (3H, s), 2.23-1.88 (2H, m), 2.13 (3H, s).

Example 5

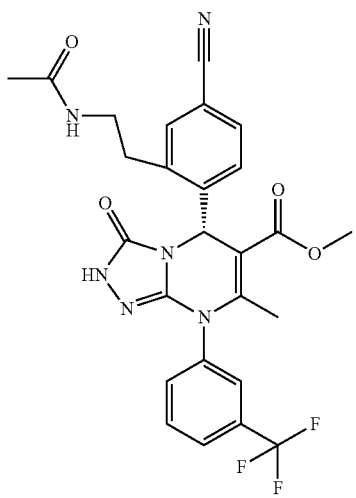 [SMILES: COC(=O)C1=C(C)N(c2cccc(C(F)(F)F)c2)c2n[nH]c(=O)n2[C@@H]1c1ccc(C#N)cc1CCNC(C)=O]

(R)-5-[2-(2-Acetylamino-ethyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 12

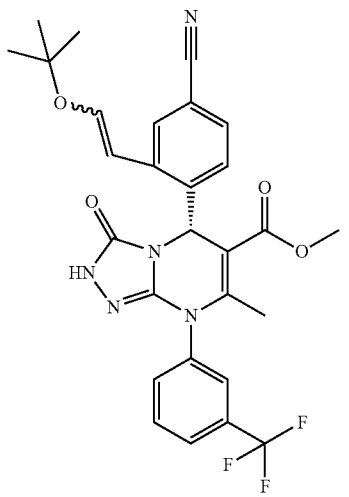 [SMILES: COC(=O)C1=C(C)N(c2cccc(C(F)(F)F)c2)c2n[nH]c(=O)n2[C@@H]1c1ccc(C#N)cc1C=COC(C)(C)C]

(R)-5-[2-(2-tert-Butoxy-vinyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester An autoclave was charged with a mixture of Intermediate 7 (10 g, 18.72 mmol), 2-methyl-2-vinyloxy-propane (6.55 g, 65.50 mmol), tri-tertiary-butyl phosphonium tetrafluoroborate (540 mg, 1.86 mmol), Herrmann-Beller catalyst (trans-di(μ-acetato)bis(O-di-o-tolyl-phosphino)benzyl)dipalladium (II)) (880 mg, 0.94 mmol), 1,2,2,6,6-pentamethylpiperidine (11.5 g, 74.20 mmol). Tetra-ethylene glycol (140 mL) was added and the resulting solution degassed under Argon. The mixture was then heated at 150° C. for 1 h. The mixture was cooled, diluted with EtOAc and aqueous 10% citric acid and the organic extract was washed with water and brine, then dried (Na$_2$SO$_4$) and concentrated in vacuo. The resultant residue was purified by chromatography, eluting with 25-75% EtOAc in cyclohexane to give the title compound as a [3:1] mixture of E/Z isomers and as a yellow foam (7.95 g).

LC-MS (Method 5): Rt=3.87 min, m/z=554.2 [M+H]$^+$

Intermediate 13

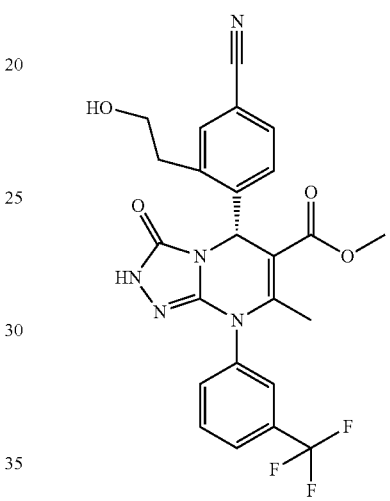

(R)-5-[4-Cyano-2-(2-hydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester A solution of Intermediate 12 (7.87 g, 14.20 mmol) in DCM (130 mL) was cooled to −10° C. using a salt/ice bath and treated drop-wise with TFA (6.35 mL, 85.47 mmol). After stirring the solution at −10° C. for 2 h the resulting solution was poured into ice-cold aqueous Na$_2$CO$_3$ solution. The organic phase was separated and the aqueous phase was further extracted with DCM (70 mL) and the combined DCM extract returned to the salt/ice bath at −5° C. Sodium borohydride (1.57 g, 41.42 mmol) was added portion-wise and after stirring for 15 minutes, MeOH (32 mL) was added to the resulting mixture. The reaction was stirred at −5° C. for 1.5 h, water was added and the resulting mixture allowed to stir vigorously for 15 mins prior to separation of the organic phase. The aqueous phase was further extracted with DCM and the combined organic extract was washed with brine, dried (Na$_2$SO$_4$) and concentrated in vacuo. The resultant residue was purified by chromatography, eluting with EtOAc and gave the title compound as a cream solid (3.7 g).

LC-MS (Method 5): Rt=3.17 min, m/z=500.1 [M+H]$^+$

Intermediate 14

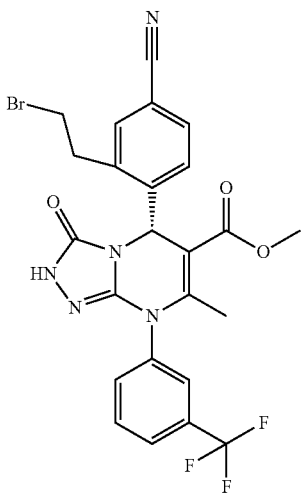 [SMILES: COC(=O)C1=C(C)N(c2cccc(C(F)(F)F)c2)c2n[nH]c(=O)n2[C@@H]1c1ccc(C#N)cc1CCBr]

(R)-5-[2-(2-Bromo-ethyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 13 (23 g, 46.1 mmol) was stirred in DCM (400 mL) at RT as tetrabromomethane (22.95 g, 69.1 mmol) was added. Triphenylphosphine (18.11 g, 69.1 mmol) was then added in portions over 10 min. The reaction mixture was briefly cooled in ice in order to maintain RT (a small initial exotherm occurs). Stirring was continued at RT for 3 h. The mixture was washed with water, the organic phase dried ($Na_2SO_4$), filtered and evaporated and the residue chromatographed, eluting with a gradient of 40% to 75% EtOAc in cyclohexane, yielding the title compound as a white solid (23.6 g).

LC-MS (Method 5): Rt=3.83 min, m/z=562.1 [M($^{79}$Br)+H]$^+$

(R)-5-[2-(2-Acetylamino-ethyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester (Example 5)

A solution of Intermediate 14 (200 mg, 0.35 mmol) and ammonia in MeOH (2M, 4 mL, 8.00 mmol) was stirred and heated at 50° C. in a sealed tube overnight. Solvent was removed under a stream of air and the resultant residue re-dissolved in THF (2 mL) and DIPEA (246 µL, 1.42 mmol). A solution of acetyl chloride (76 µL, 1.07 mmol) in THF (1 mL) was added at rt under Argon, stirred for 1 h and then solvent removed under a stream of air. The resultant residue was dissolved in MeOH (5 mL) and stirred at RT with potassium carbonate (0.12 g, 0.87 mmol). After 1 h the mixture was added to EtOAc-aqueous HCl and extracted into EtOAc. These extracts were washed with water and brine, dried ($MgSO_4$), filtered and concentrated in vacuo. Purification of the resultant residue by MDAP gave the title compound as a white solid (43 mg).

LC-MS (Method 3): Rt=4.16 min, m/z=541.1 [M+H]$^+$ $^1$H NMR (400 MHz, d$_6$-DMSO) δ 11.24 (1H, bs), 8.12 (1H, s), 8.04 (1H, t, J=5.3 Hz), 7.95-7.89 (2H, m), 7.81 (1H, t, J=7.9 Hz), 7.71-7.62 (3H, m), 6.17 (1H, s), 3.51 (3H, s), 3.58-3.44 (2H, m), 3.29-3.14 (2H, m), 2.14 (3H, s), 1.83 (3H, s).

Example 6

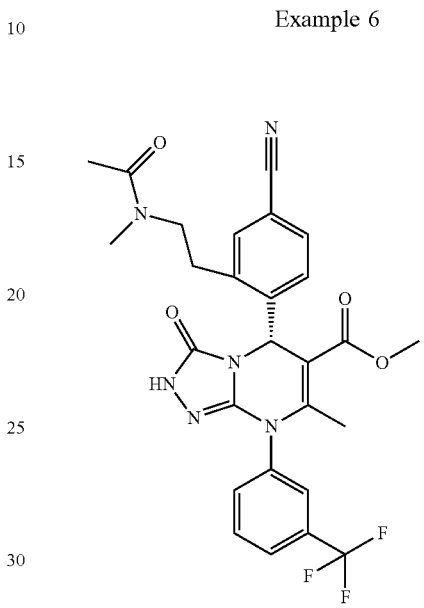

(R)-5-{2-[2-(Acetyl-methyl-amino)-ethyl]-4-cyano-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester A solution of Intermediate 14 (150 mg, 0.267 mmol) and methylamine in THF (2M, 1.34 mL, 2.68 mmol) was stirred and heated at 50° C. in a sealed tube overnight. Solvent was removed under a stream of air and the resultant residue re-dissolved in THF (2 mL) and DIPEA (185 µL, 1.07 mmol). A solution of acetyl chloride (57 µL, 0.80 mmol) in THF (1 mL) was added at RT under Argon, stirred for 1 h and then solvent removed under a stream of air. The resultant residue was dissolved in EtOAC, washed with water, aqueous sodium bicarbonate and brine then dried ($MgSO_4$), filtered and concentrated in vacuo. This residue was re-dissolved in MeOH (8 mL) and stirred at RT with potassium carbonate (71 mg, 0.513 mmol). After 2 hours the mixture was added to EtOAc-aqueous HCl and extracted into EtOAc. These extracts were washed with water and brine, dried ($MgSO_4$), filtered and concentrated in vacuo. Purification of the resultant residue by MDAP gave the title compound as a white solid (40 mg).

LC-MS (Method 3): Rt=4.21 min, m/z=555.1 [M+H]$^+$ $^1$H NMR (400 MHz, d$_6$-DMSO) δ 11.22-11.17 (1H, m), 8.12 (1H, bs), 7.95-7.89 (2H, m), 7.85-7.72 (2H, m), 7.69-7.59 (2H, m), 6.19-6.12 (1H, m), 3.49 (3H, s), 3.47-3.37 (2H, m), 3.20-3.05 (1H, m), 3.02-2.84 (4H, m), 2.22-1.78 (8H, m).

Example 7

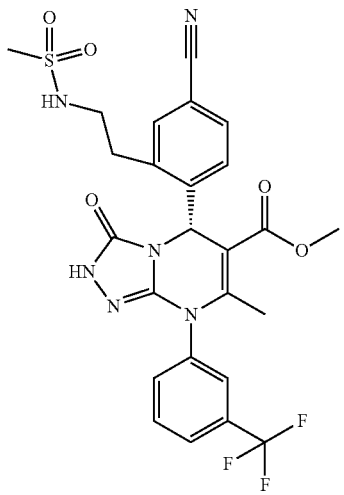

(R)-5-[4-Cyano-2-(2-methanesulfonylamino-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester A solution of Intermediate 14 (100 mg, 0.178 mmol) and ammonia in MeOH (2M, 2 mL) was stirred and heated at 50° C. in a sealed tube overnight. Solvent was removed under a stream of air and the resultant residue re-dissolved in THF (2 mL) This mixture was added to a solution of methane sulfonyl chloride (58μL, 0.748 mmol) and DIPEA (138 μL, 0.796 mmol) in THF (1 mL) at RT, stirred for 30 mins and then solvent removed under a stream of air. Purification of the resultant residue by MDAP gave the title compound as a white solid (21 mg).

LC-MS (Method 3): Rt=4.29 min, m/z=577.0 [M+H]$^+$ $^1$H NMR (400 MHz, d$_6$-DMSO) δ 11.24 (1H, bs), 8.12 (1H, bs), 7.95-7.89 (2H, m), 7.81 (1H, t, J=7.8 Hz), 7.76 (1H, d, J=1.4 Hz), 7.70 (1H, dd, J=8.0 and 1.6 Hz), 7.67 (1H, d, J=8.0 Hz), 7.21 (1H, t, J=5.3 Hz), 6.16 (1H, s), 3.62-3.52 (1H, m), 3.51 (3H, s), 3.44-3.33 (2H, m), 3.27-3.19 (1H, m), 2.95 (3H, s), 2.14 (3H, s).

Example 8

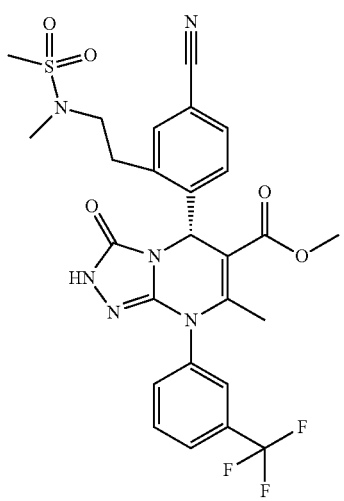

(R)-5-{4-Cyano-2-[3-(methanesulfonyl-1-methyl-amino)-ethyl]-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester A solution of Intermediate 14 (190 mg, 0.329 mmol) and methylamine in THF (2M, 2.0 mL, 4.0 mmol) was stirred and heated at 50° C. in a sealed tube overnight. Solvent was removed under a stream of air and the resultant residue re-dissolved in THF (2 mL). This was added to a stirred solution of DIPEA (285 μL, 1.65 mmol) and methanesulfonyl chloride (78 μL, 1.00 mmol) in THF (1.0 mL) at RT under Argon. Solvent was removed under a stream of air after 1 h and the resultant residue dissolved in EtOAc, washed with water, aqueous sodium carbonate and brine then dried (MgSO$_4$), filtered and concentrated in vacuo. Purification of the resultant residue by MDAP gave the title compound as a white solid (95 mg).

LC-MS (Method 3): Rt=4.46 min, m/z=591.0 [M+H]$^+$ $^1$H NMR (400 MHz, d$_6$-DMSO) δ 11.22 (1H, bs), 8.12 (1H, bs), 7.95-7.89 (2H, m), 7.81 (1H, t, J=7.8 Hz), 7.78-7.76 (1H, m), 7.73-7.63 (2H, m), 6.19 (1H, s), 3.73-3.43 (2H, m), 3.51 (3H, s), 3.30-3.22 (2H, m, obscured by water), 2.95 (3H, s), 2.89 (3H, s), 2.14 (3H, s).

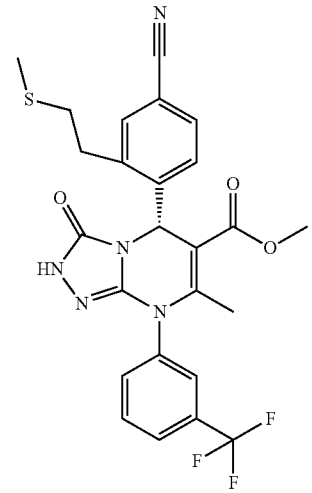

Example 9

(R)-5-[4-Cyano-2-(2-methylsulfanyl-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester Sodium thiomethoxide (30 mg, 0.40 mmol) was added to a solution of Intermediate 14 (100 mg, 0.18 mmol) in IMS (1 mL) and stirred at RT overnight. Solvent was removed in vacuo and the resultant residue partitioned between EtOAc-water. EtOAc extracts were washed with water and brine, dried (MgSO$_4$), filtered and concentrated in vacuo. Purification of the resultant residue by MDAP gave the title compound as a white solid (45 mg).

LC-MS (Method 3): Rt=4.88 min, m/z=530.1 [M+H]$^+$ $^1$H NMR (400 MHz, d$_6$-DMSO) δ 11.20 (1H, s), 8.11 (1H, bs), 7.81 (1H, t, J=7.9 Hz), 7.76 (1H, d, J=1.5 Hz), 7.68 (1H, dd, J=8.1 and 1.6 Hz), 7.63 (1H, d, J=8.1 Hz), 6.15 (1H, s), 3.51 (3H, s), 3.45-3.35 (1H, m), 3.29-3.20 (1H, m), 3.09-3.00 (1H, m), 2.93-2.84 (1H, m), 2.19 (3H, s).

Example 10

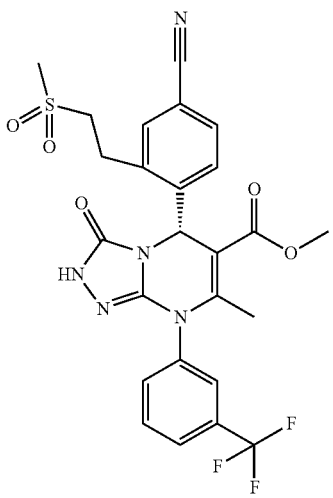 [SMILES: COC(=O)C1=C(C)N(c2cccc(C(F)(F)F)c2)c2n[nH]c(=O)n2[C@@H]1c1ccc(C#N)cc1CCS(C)(=O)=O]

(R)-5-[4-Cyano-2-(2-methanesulfonyl-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester m-Chloroperoxybenzoic acid (50-55%, 0.30 g, 0.95 mmol) was added in portions to a stirred solution of Example 9 (0.23 g, 0.43 mmol) in DCM (5 mL) at RT. When the reaction was complete by LCMS, the mixture was diluted with DCM (10 mL), aqueous NaOH (1M) added and thoroughly shaken. The separated DCM phase was washed with water and brine then isolated using a phase separation cartridge and concentrated in vacuo. Purification of the resultant residue by MDAP gave the title compound as a white solid (35 mg).

LC-MS (Method 3): Rt=4.31 min, m/z=562.0 [M+H]$^+$ $^1$H NMR (400 MHz, d$_6$-DMSO) δ 11.25 (1H, s), 8.13 (1H, bs), 7.95-7.90 (2H, m), 7.85-7.80 (2H, m), 7.73 (1H, dd, J=8.1 and 1.6 Hz), 7.70-7.65 (1H, m), 6.16 (1H, s), 3.91-3.82 (1H, m), 3.66-3.54 (2H, m), 3.52 (3H, s), 3.46-3.37 (1H, m), 3.10 (3H, s), 2.14 (3H, s).

Example 11

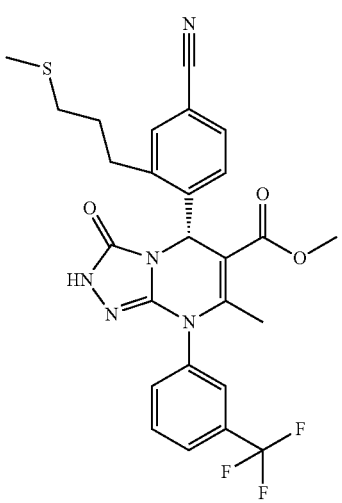

(R)-5-[4-Cyano-2-(2-methylsulfanyl-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester Sodium thiomethoxide (58 mg, 0.79 mmol) was added to a solution of Intermediate 11 (300 mg, 0.52 mmol) in IMS (4 mL) and stirred at RT overnight. Solvent was removed in vacuo and the resultant residue partitioned between EtOAc-water. EtOAc extracts were washed with water and brine, dried (MgSO$_4$), filtered and concentrated in vacuo to give crude product (309 mg). Purification of some of this residue (110 mg) by MDAP gave the title compound as a white solid (76 mg).

LC-MS (Method 3): Rt=4.98 min, m/z=544.0 [M+H]$^+$ $^1$H NMR (400 MHz, d$_6$-DMSO) δ 11.17 (1H, bs), 8.10 (1H, bs), 7.94-7.87 (2H, m), 7.81 (1H, t, J=7.9 Hz), 7.72-7.69 (1H, m), 7.66 (1H, dd, J=8.1 and 1.6 Hz), 7.61 (1H, d, J=8.1 Hz), 6.17 (1H, s), 3.50 (3H, s), 3.26-3.04 (2H, m), 2.63 (2H, t, J=7.2 Hz), 2.19-2.12 (4H, m), 2.11 (3H, s), 2.01-1.90 (1H, m).

Example 12

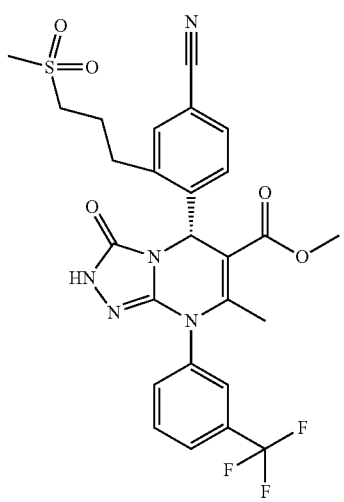

(R)-5-[4-Cyano-2-(2-methanesulfonyl-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester m-Chloroperoxybenzoic acid (50-55%, 0.25 g, 0.72 mmol) was added in portions to a stirred solution of Example 11 (198 mg, 0.36 mmol) in DCM (5 mL) at RT. After 1 h the reaction mixture was diluted with DCM (10 mL), aqueous NaOH (1 M) added and thoroughly shaken. The separated DCM phase was washed with water and brine then isolated using a phase separation cartridge and concentrated in vacuo. Purification of the resultant residue by MDAP gave the title compound as a white solid (60 mg).

LC-MS (Method 3): Rt=4.30 min, m/z=576.0 [M+H]$^+$ $^1$H NMR (400 MHz, d$_6$-DMSO) δ 11.21 (1H, bs), 8.12 (1H, bs), 7.96-7.89 (2H, m), 7.82 (1H, t, J=7.8 Hz), 7.79-7.75 (1H, m), 7.69 (1H, dd, J=8.1 and 1.6 Hz), 7.65 (1H, d, J=8.1 Hz), 6.19 (1H, s), 3.51 (3H, s), 3.32-3.24 (3H, m, obscured by water), 3.21-3.09 (1H, m), 3.03 (3H, s), 2.39-2.26 (1H, m), 2.24-2.12 (4H, m).

Example 13

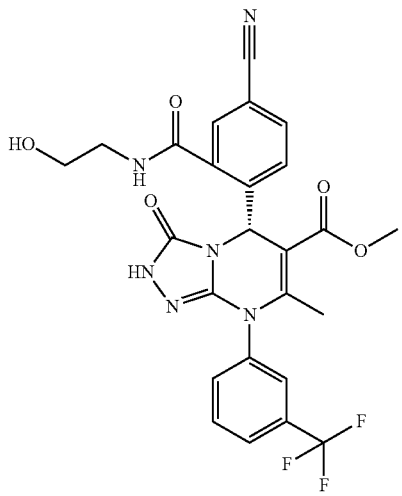 [SMILES: COC(=O)C1=C(C)N(c2cccc(C(F)(F)F)c2)c2n[nH]c(=O)n2[C@@H]1c1ccc(C#N)cc1C(=O)NCCO]

(R)-5-[4-Cyano-2-(2-hydroxy-ethylcarbamoyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

Intermediate 15

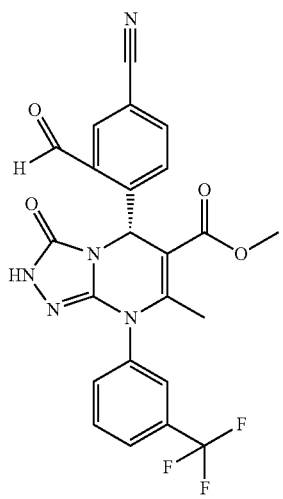 [SMILES: COC(=O)C1=C(C)N(c2cccc(C(F)(F)F)c2)c2n[nH]c(=O)n2[C@@H]1c1ccc(C#N)cc1C=O]

(R)-5-(4-Cyano-2-formyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 8 (7.92 g, 16.45 mmol) was suspended in a mixture of acetone (80 mL) and water (8 mL). 4-Methylmorpholine N-oxide monohydrate (4.45 g, 32.92 mmol) was added, followed by potassium osmate dihydrate (62 mg, 0.17 mmol) and the reaction mixture stirred vigorously at RT for 18 h. $Na_2S_2O_5$ (6.90 g, 36.30 mmol) was then added and the reaction was stirred for a further 20 mins. The resultant mixture was filtered through Celite and then evaporated in vacuo. The resultant residue was taken up in THF (100 mL) and water (100 mL) and then cooled to 0° C. before sodium periodate (7.04 g, 32.91 mmol) was added. The reaction mixture was stirred at <10° C. under argon for 3 h, then diluted with EtOAc. The organic layer was separated, and the aqueous layer extracted with EtOAc. The combined organic layers were washed with water, then brine, dried ($MgSO_4$) and evaporated in vacuo. The resulting residue was purified by silica gel chromatography eluting with a gradient of 0-80% EtOAc in cyclohexane to yield the title compound as a brown foam (6.58 g).

LC-MS (Method 1): Rt=3.20 min, m/z=484 [M+H]$^+$

Intermediate 16

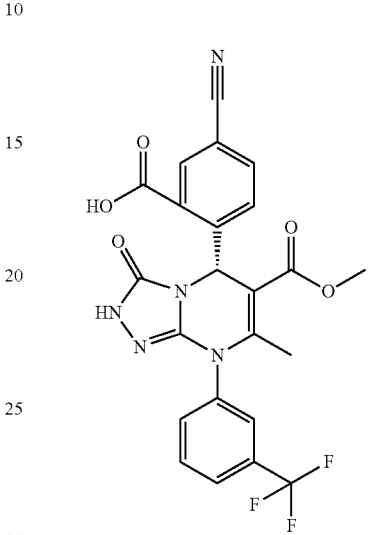

(R)-5-(2-Carboxy-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester A solution of Intermediate 15 (3.50 g, 7.25 mmol), sodium dihydrogenphosphate (861 mg, 7.25 mmol) and 2-methyl-2-butene (2 M in THF; 15.75 mL, 31.50 mmol) in a mixture of t-BuOH: water [44 mL: 12.5 mL] was stirred at RT as sodium chlorite was added portion wise over 10 mins. An exotherm generated was controlled by the rate of addition to the reaction and with ice/water cooling. The reaction was allowed to stir at RT for 4 h then diluted with EtOAc (100 mL) and water (100 mL) and a little aqueous 1 M HCl was added to ensure acidity. The organic phase was washed successively with 10% aqueous $K_2CO_3$ and 10% aqueous citric acid and the combined organic layer was washed with brine, dried ($Na_2SO_4$) and concentrated in vacuo. The resulting residue was purified by silica gel chromatography eluting with a gradient of 0-5% MeOH in DCM containing 0.5% acetic acid, to yield the title compound as a off-white gum (1.47 g).

LC-MS (Method 1): Rt=3.08 min, m/z=500 [M+H]$^+$ (R)-5-[4-Cyano-2-(2-hydroxy-ethylcarbamoyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester (Example 13)

Intermediate 16 (43 mg, 0.086 mmol), ethanolamine (6.6 mg, 0.12 mmol) and DIPEA (44 mg, 0.34 mmol) were dissolved in DMF (0.8 mL) and the resulting mixture was treated with HATU (49 mg, 0.29 mmol) and stirred at RT for 18 hours. The mixture was partitioned between EtOAc and water. The organic layer was separated, washed twice with water, dried ($Na_2SO_4$) and concentrated in vacuo. The resulting residue was purified by MDAP and gave the title compound as a white solid (17 mg).

LC-MS (Method 3): Rt=3.87 min, m/z=543.2 [M+H]⁺

¹H NMR (400 MHz, d₆-DMSO) δ 11.59 (1H, s), 9.28 (1H, m), 8.37-8.02 (2H, bs), 7.96-7.87 (2H, m), 7.86-7.72 (3H, m), 6.51 (1H, m), 4.76 (1H, t, J=5.1 Hz), 3.62-3.53 (2H, m), 3.40 (3H, s), 3.28-3.18 (2H, m), 2.14 (3H, s).

The following examples were prepared from Intermediate 16 and the appropriately substituted amines using an analogous method to Example 13:

| Ex | Structure | Name | LC-MS (Method 3) | NMR |
|---|---|---|---|---|
| 14 | 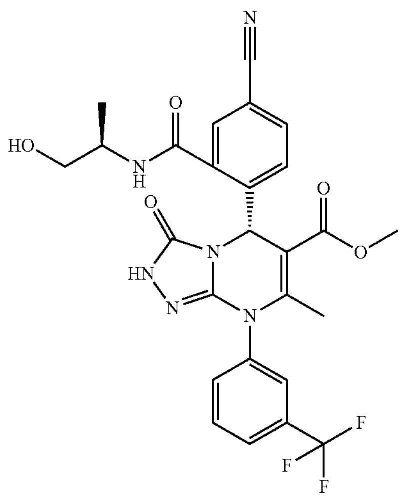 [SMILES: COC(=O)C1=C(C)N(c2cccc(C(F)(F)F)c2)c2n[nH]c(=O)n2[C@@H]1c1ccc(C#N)cc1C(=O)N[C@H](C)CO] | (R)-5-[4-Cyano-2-((R)-2-hydroxy-1-methyl-ethylcarbamoyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester | Rt = 4.03 min, m/z = 557.2 [M + H]⁺ | ¹H NMR (400 MHz, d₆-DMSO) δ 11.57 (1H, s), 9.05 (1H, d, J = 7.5 Hz), 8.19 (2H, bs), 7.95-7.91 (1H, m), 7.90 (1H, dd, J = 8.2, 1.9 Hz), 7.86-7.72 (3H, m), 6.39 (1H, m), 4.08-3.97 (1H, m), 3.50-3.35 (2H, om), 3.42 (3H, s), 2.16 (3H, d, J = 0.9 Hz), 1.20 (3H, d, J = 6.7 Hz). OH not observed. |
| 15 | 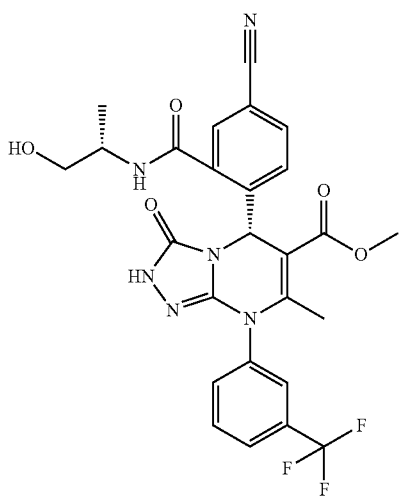 | (R)-5-[4-Cyano-2-((S)-2-hydroxy-1-methyl-ethylcarbamoyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester | Rt = 3.94 min, m/z = 557.2 [M + H]⁺ | ¹H NMR (400 MHz, d₆-DMSO) δ 11.60 (1H, s), 9.19 (1H, d, J = 7.7 Hz), 8.20 (2H, bs), 7.95-7.91 (1H, m), 7.89 (1H, dd, J = 8.1, 1.8 Hz), 7.86-7.71 (3H, m), 6.59 (1H, m), 4.82 (1H, t, J = 5.5 Hz), 4.12-4.00 (1H, m), 3.54-3.44 (2H, m), 3.41 (3H, s), 2.15 (3H, d, J = 0.9 Hz), 1.14 (3H, d, J = 6.8 Hz). |
| 16 | 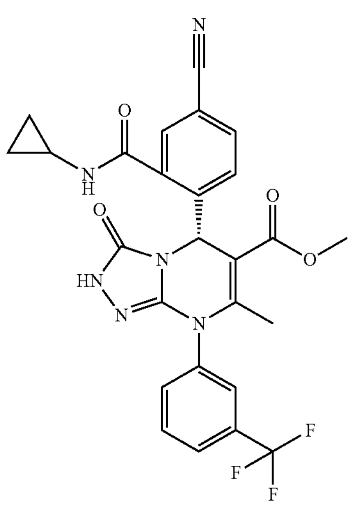 [SMILES: COC(=O)C1=C(C)N(c2cccc(C(F)(F)F)c2)c2n[nH]c(=O)n2[C@@H]1c1ccc(C#N)cc1C(=O)NC1CC1] | (R)-5-(4-Cyano-2-cyclopropylcarbamoyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester | Rt = 4.27 min, m/z = 539.2 [M + H]⁺ | ¹H NMR (400 MHz, d₆-DMSO) δ 11.57 (1H, s), 9.19 (1H, d, J = 7.7 Hz), 8.20 (2H, bs), 7.95-7.91 (1H, m), 7.90 (1H, dd, J = 8.1, 1.8 Hz), 7.86-7.73 (3H, m), 6.27 (1H, m), 3.42 (3H, s), 2.91-2.82 (1H, m), 2.12 (3H, d, J = 0.9 Hz), 0.81-0.69 (2H, m), 0.64-0.51 (2H, m). |

-continued

| Ex | Structure | Name | LC-MS (Method 3) | NMR |
|---|---|---|---|---|
| 17 | 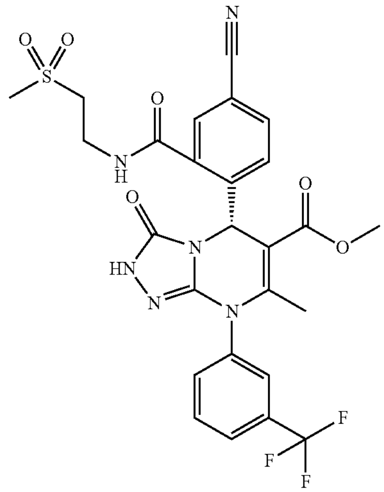 | (R)-5-[4-Cyano-2-(2-methanesulfonyl-ethylcarbamoyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester | Rt = 4.05 min, m/z = 605.1 [M + H]+ | $^1$H NMR (400 MHz, $d_6$-DMSO) δ 11.59 (1H, s), 9.53 (1H, t, J = 5.4 Hz), 8.37-8.02 (2H, bs), 7.96-7.89 (2H, m), 7.87-7.85 (1H, m), 7.85-7.74 (2H, m), 6.50 (1H, d, J = 0.9 Hz), 3.91-3.78 (1H, m), 3.72-3.59 (1H, m), 3.51-3.41 (2H, om), 3.41 (3H, s), 3.07 (3H, s), 2.15 (3H, t, J = 0.9 Hz). |

Examples 18a/18b

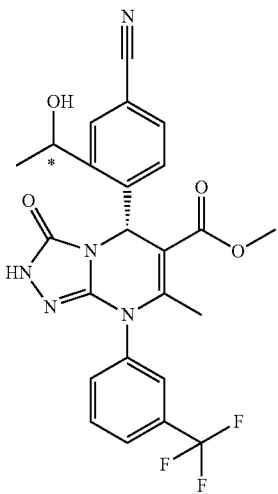

Diastereoisomer 1

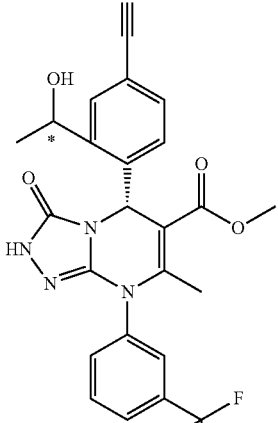

Diastereoisomer 2

18a  (R)-5-[4-Cyano-2-(1-hydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester (diastereoisomers 18a and 18b)

A cooled (0° C.) solution of Intermediate 15 (245 mg, 0.507 mmol) in THF (3.0 mL) was treated with methylmagnesium bromide (1.4 M in toluene; 0.78 mL, 1.10 mmol) and the reaction mixture stirred for 40 mins. Further methylmagnesium bromide (1.4 M in toluene; 0.78 mL, 1.10 mmol) was added and then after stirring for another 40 mins, a final aliquot of methylmagnesium bromide (1.4 M in toluene; 0.78 mL, 1.10 mmol) was added at 0° C. After 10 mins the reaction mixture was partitioned between EtOAc and saturated aqueous NH$_4$Cl solution, and the organic phase was separated, washed with brine, dried (Na$_2$SO$_4$) and concentrated in vacuo. The resulting residue was purified by MDAP and gave the title compounds Example 18a (47 mg) and Example 18b (17 mg) as a white solids.

18b

Example 18a

Diastereoisomer 1

LC-MS (Method 3): Rt=4.12 min, m/z=500.1 [M+H]+
$^1$H NMR (400 MHz, $d_6$-DMSO) δ 11.20 (1H, s), 8.11 (1H, bs), 7.94-7.87 (3H, m), 7.81 (1H, t, J=7.8 Hz), 7.69 (1H, dd, J=8.2, 1.9 Hz), 7.57 (1H, d, J=8.2 Hz), 6.21 (1H, s), 5.52-5.43 (1H, m), 5.22 (1H, d, J=4.4 Hz), 3.55 (3H, s), 2.11 (3H, d, J=0.7 Hz), 1.57 (3H, d, J=6.3 Hz).

Example 18b

Diastereoisomer 2

LC-MS (Method 3): Rt=4.42 min, m/z=500.1 [M]+
$^1$H NMR (400 MHz, $d_6$-DMSO) δ 11.47 (1H, s), 8.12 (1H, bs), 7.96 (1H, d, J=1.9 Hz), 7.94-7.88 (2H, m), 7.82 (1H, t, J=8.0 Hz), 7.74 (1H, dd, J=8.1, 1.8 Hz), 7.69 (1H, d, J=8.1 Hz), 6.37 (1H, s), 5.70-5.61 (1H, m), 5.22 (1H, m), 3.48 (3H, s), 2.17 (3H, d, J=0.7 Hz), 1.46 (3H, d, J=6.4 Hz).

Example 19

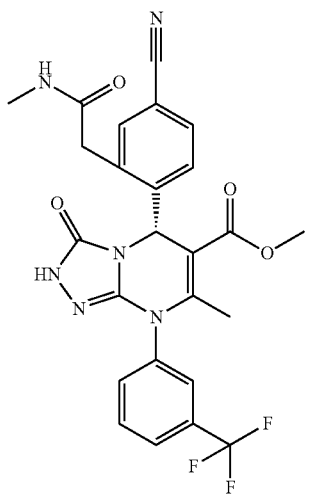

(R)-5-(4-Cyano-2-methylcarbamoylmethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

Intermediate 17

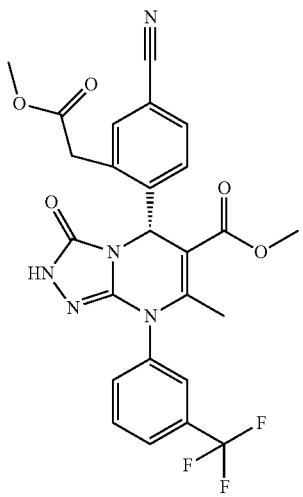

(R)-5-(4-Cyano-2-methoxycarbonylmethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester A microwave vial was charged with Intermediate 7 (2.5 g, 4.67 mmol), palladium(0)bis(dibenzylideneacetone) (132 mg, 0.23 mmol), zinc fluoride (242 mg, 2.34 mmol) and dry DMF (12 mL), then degassed under an argon atmosphere. A solution of tri(tert-butyl)phosphine (1 M in toluene; 475 μL, 0.19 mmol) and 1-(tert-butyldimethyl silyloxy)-1-methoxyethene (3.05 mL, 14 mmol) were added to the reaction, followed by further degassing. The mixture was heated under microwave irradiation at 135° C. for 4 h. Further 1-(tert-butyldimethylsilyloxy)-1-methoxyethene (0.7 mL, 3.2 mmol) was added and the mixture heated under microwave irradiation for a further 1 h at 135° C. The resultant mixture was partitioned between EtOAc and water, and the aqueous layer was extracted with EtOAc. The combined organic extract was washed with brine, dried (MgSO$_4$) and then concentrated in vacuo. The resultant residue was dissolved in MeOH, treated with TFA (5 drops) and allowed to stir for 18 h at RT (this process removes the TBDMS group from the initially generated silylated product). The reaction mixture was concentrated in vacuo and then purified by chromatography, eluting with 0-100% EtOAc in cyclohexane, to afford the title compound as a white solid (1.82 g).

LC-MS (Method 4): Rt=3.45 min, m/z=528.3 [M+H]$^+$

Intermediate 18

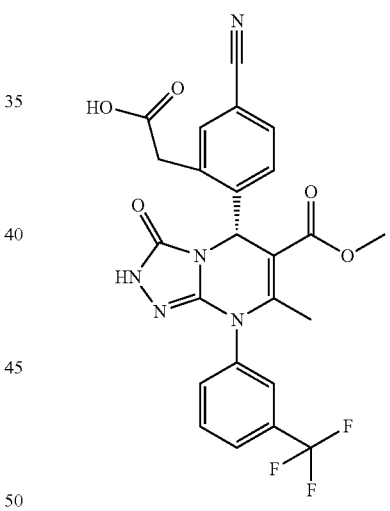

(R)-5-(2-Carboxymethyl-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 17 (900 mg, 1.71 mmol) and LiOH.H$_2$O (146 mg, 3.48 mmol) were dissolved in a mixture of water/THF (2.6 mL: 13 mL) and the resulting solution was stirred at RT for 2 h. The reaction was diluted with EtOAc (100 mL) and water (100 mL) and a little aqueous 1 M HCl was added to ensure acidity. The organic phase was washed with brine, dried (Na$_2$SO$_4$) and concentrated in vacuo. The resultant residue was triturated with DCM to give the title compound as a cream solid (0.50 g).

LC-MS (Method 3): Rt=3.99 min, m/z=514.2 [M+H]+

(R)-5-(4-Cyano-2-methoxycarbonylmethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester (Example 19)

A solution of Intermediate 18 (137 mg, 0.267 mmol) in THF (2 mL) was treated with CDI (86.5 mg, 0.534 mmol) and the resulting solution was stirred at RT for 1 h. A solution of methylamine (2 M in THF; 342 μL, 0.684 mmol) was added and the mixture was stirred for a further 18 h at RT. The reaction was partitioned between EtOAc and water. The organic layer was separated, washed with brine, dried (Na$_2$SO$_4$) and concentrated in vacuo. The resulting residue was purified by MDAP and gave the title compound as a white solid (81 mg).

LC-MS (Method 3): Rt=4.03 min, m/z=527.1 [M+H]+

$^1$H NMR (400 MHz, d$_6$-DMSO) δ 11.26 (1H, s), 8.13 (1H, bs), 8.05-7.97 (1H, m), 7.96-7.87 (2H, m), 7.81 (1H, t, J=7.8 Hz), 7.74-7.63 (3H, m), 6.20 (1H, m), 4.05 (1H, d, J=15.7 Hz), 3.89 (1H, d, J=15.7 Hz), 3.42 (3H, s), 2.65 (3H, d, J=4.6 Hz), 2.17 (3H, s).

The following examples were prepared from Intermediate 18 and the appropriately substituted amines using an analogous method to Example 19:

| Ex | Structure | Name | LC-MS (Method 3) | NMR |
|---|---|---|---|---|
| 20 | 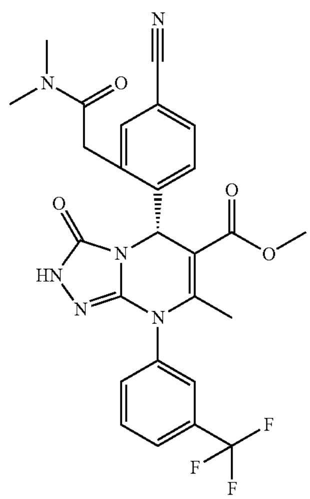 | (R)-5-(4-Cyano-2-dimethylcarbamoylmethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester | Rt = 4.14 min, m/z = 541.2 [M + H]+ | $^1$H NMR (400 MHz, d$_6$-DMSO) δ 11.22 (1H, s), 8.12 (1H, bs), 7.92 (2H, d, J = 7.7 Hz), 7.82 (1H, t, J = 7.8 Hz), 7.76-7.67 (2H, m), 7.42-7.39 (1H, m), 6.09 (1H, m), 4.35 (1H, d, J = 16.6 Hz), 4.24 (1H, d, J = 16.6 Hz), 3.46 (3H, s), 3.07 (3H, s), 2.96 (3H, s), 2.17 (3H, s). |
| 21 | 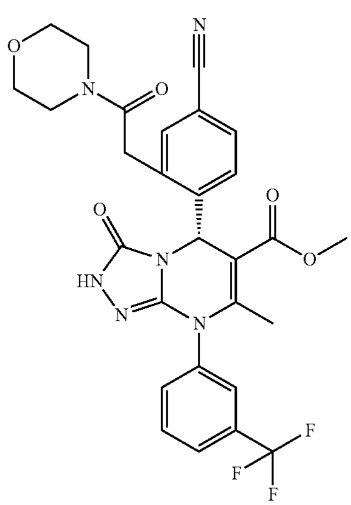 [SMILES: COC(=O)C1=C(C)N(c2cccc(C(F)(F)F)c2)c2n[nH]c(=O)n2[C@@H]1c1ccc(C#N)cc1CC(=O)N1CCOCC1] | (R)-5-[4-Cyano-2-(2-morpholin-4-yl-2-oxo-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester | Rt = 4.13 min, m/z = 583.2 [M + H]+ | $^1$H NMR (400 MHz, d$_6$-DMSO) δ 11.27 (1H, s), 8.13 (1H, bs), 7.92 (2H, d, J = 7.7 Hz), 7.82 (1H, t, J = 7.8 Hz), 7.77-7.67 (2H, m), 7.45 (1H, d, J = 1.3 Hz), 6.09 (1H, m), 4.41 (1H, d, J = 16.7 Hz), 4.22 (1H, d, J = 16.7 Hz), 3.70-3.43 (8H, m), 3.47 (3H, s), 2.17 (3H, s). |

Example 22

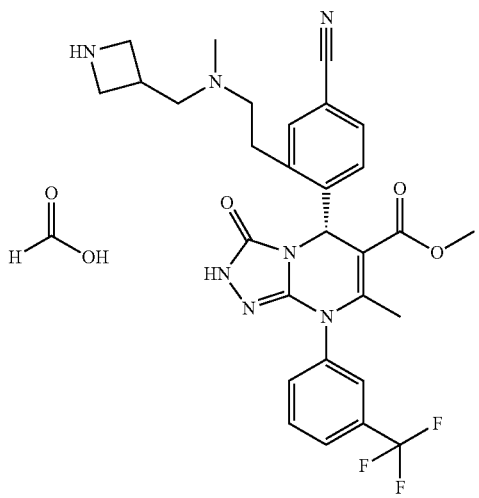 [SMILES: O=CO ; COC(=O)C1=C(C)N(c2cccc(C(F)(F)F)c2)c2n[nH]c(=O)n2[C@@H]1c1ccc(C#N)cc1CCN(C)CC1CNC1]

(R)-5-{2-[2-(Azetidin-3-ylmethyl-methyl-amino)-ethyl]-4-cyano-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester formate salt Intermediate 19

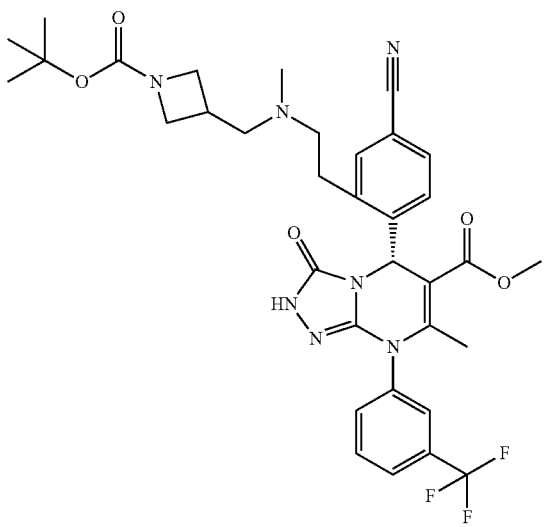 [SMILES: COC(=O)C1=C(C)N(c2cccc(C(F)(F)F)c2)c2n[nH]c(=O)n2[C@@H]1c1ccc(C#N)cc1CCN(C)CC1CN(C(=O)OC(C)(C)C)C1]

(R)-5-(2-{2-[(1-tert-Butoxycarbonyl-azetidin-3-ylmethyl)-methyl-amino]-ethyl}-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester A solution of Intermediate 14 (100 mg, 0.178 mmol) and 1-boc-3-(methylaminomethyl)-azetidine (78 mg, 0.39 mmol) in MeCN (2 mL) was stirred and heated at 50° C. for 4 h. Solvent was removed in vacuo and the resultant residue was dissolved in EtOAC, washed with water and brine then dried ($Na_2SO_4$), filtered and concentrated in vacuo. This resultant residue was purified by chromatography, eluting with 2.5-5% MeOH in DCM then 5% (2 M $NH_3$ in MeOH) in DCM and afforded the title compound as a white solid (92 mg).

LC-MS (Method 4): Rt=2.82 min, m/z=682.4 $[M+H]^+$ (R)-5-{2-[2-(Azetidin-3-ylmethyl-methyl-amino)-ethyl]-4-cyano-phenyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester formate salt (Example 22)

A solution of Intermediate 19 (81 mg, 0.119 mmol) in DCM (2 mL) was treated with water (30 μL) and TFA (0.30 mL) and stirred at RT for 3½ h. Solvent was removed in vacuo and the resultant residue was purified by MDAP and gave the title compound (45 mg) as a white solid.

LC-MS (Method 4): Rt=2.83 min, m/z=582.2 $[M+H]^+$ $^1$H NMR (400 MHz, $d_6$-DMSO) δ 10.50 (1H, v. bs), 8.39 (1H, s, formate), 8.10 (1H, bs), 7.95-7.86 (2H, m), 7.81 (1H, t, J=7.9 Hz), 7.71 (1H, s), 7.68-7.59 (2H, m), 6.15 (1H, m), 3.93-3.79 (2H, m), 3.60-3.46 (2H, om), 3.51 (3H, s), 3.35-3.21 (2H, m), 3.15-3.03 (1H, m), 3.02-2.91 (1H, m), 2.89-2.77 (1H, m), 2.73-2.58 (2H, m), 2.26 (3H, s), 2.13 (3H, s). Amine NH not observed/obscured.

The following examples were prepared from Intermediate 14 and the appropriately substituted mono-Boc protected bis-amines using an analogous method to Example 22:

| Ex | Structure | LC-MS (Method 3) | NMR |
|---|---|---|---|
| 23 | 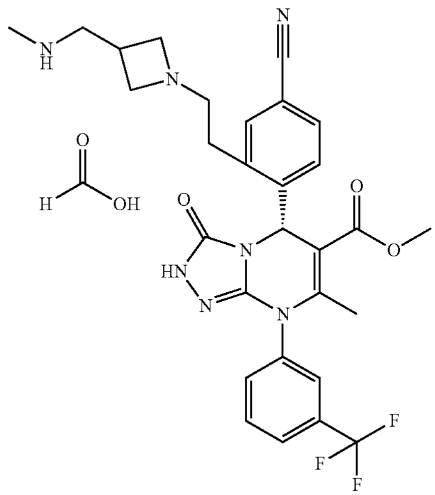 | Rt = 2.83 min, m/z = 582.3 [M + H]+ | ¹H NMR (400 MHz, d₆-DMSO) δ 11.21 (1H, v. bs), 8.28 (1H, s, formate), 8.11 (1H, bs), 7.97-7.88 (2H, m), 7.81 (1H, t, J = 7.8 Hz), 7.70 (1H, s), 7.68-7.59 (2H, m), 6.12 (1H, m), 3.50 (3H, s), 3.43-3.35 (2H, m), 3.16-3.03 (2H, m), 3.02-2.91 (4H, m), 2.90-2.81 (1H, m), 2.80-2.69 (1H, m), 2.69-2.59 (1H, m), 2.45 (3H, s), 2.13 (3H, s). Amine NH not observed/ obscured. |
| 24 | 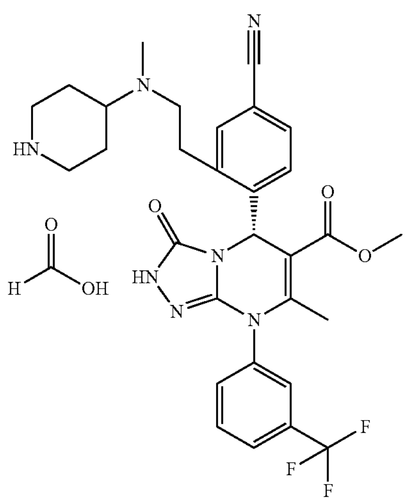 | Rt = 2.84 min, m/z = 596.3 [M + H]+ | ¹H NMR (400 MHz, d₆-DMSO) δ 11.23 (1H, v. bs), 8.32 (1H, s, formate), 8.10 (1H, bs), 7.97-7.87 (2H, m), 7.82 (1H, t, J = 7.9 Hz), 7.73 (1H, s), 7.68-7.58 (2H, m), 6.15 (1H, m), 3.51 (3H, s), 3.29-3.15 (3H, m), 3.15-3.02 (1H, m), 3.02-2.88 (1H, m), 2.83-2.62 (4H, m), 2.32 (3H, s), 2.13 (3H, s), 1.89-1.76 (2H, m), 1.70-1.51 (2H, m). Amine NH not observed/ obscured. |
| 25* | 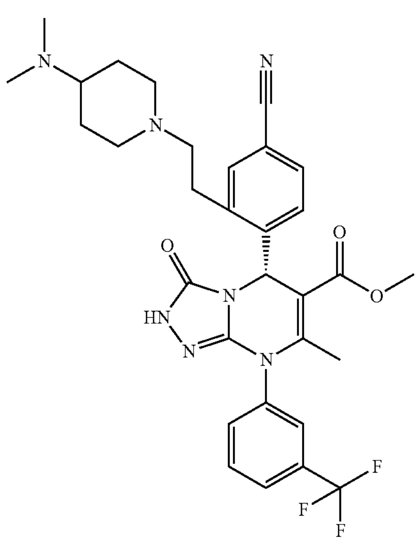 | Rt = 2.92 min, m/z = 610.2 [M + H]+ | ¹H NMR (400 MHz, d₆-DMSO) δ 11.19 (1H, s), 8.09 (1H, bs), 7.99-7.88 (2H, m), 7.81 (1H, t, J = 8.0 Hz), 7.71 (1H, m), 7.68-7.58 (2H, m), 6.14 (1H, m), 3.50 (3H, s), 3.26-3.09 (2H, om), 3.08-2.97 (2H, m), 2.83-2.68 (1H, m), 2.66-2.54 (1H, m), 2.19 (6H, s), 2.13 (3H, s), 2.12-1.94 (3H, m), 1.80-1.70 (2H, m), 1.46-1.31 (2H, m). |

-continued

| Ex | Structure | LC-MS (Method 3) | NMR |
|---|---|---|---|
| 26* | 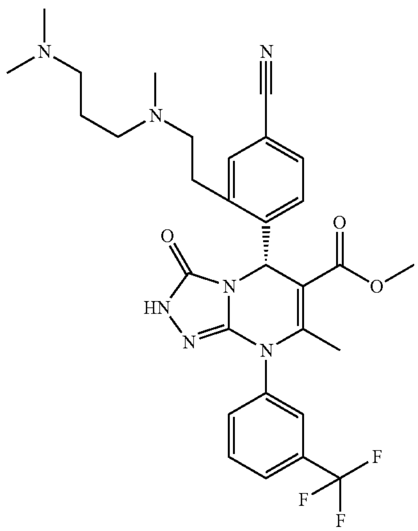 | Rt = 2.91 min, m/z = 598.2 [M + H]+ | $^1$H NMR (400 MHz, d$_6$-DMSO) δ 11.19 (1H, s), 8.11 (1H, bs), 7.96-7.87 (2H, m), 7.81 (1H, t, J = 7.8 Hz), 7.74 (1H, s), 7.68-7.58 (2H, m), 6.15 (1H, m), 3.51 (3H, s), 3.29-3.19 (1H, om), 3.17-3.06 (1H, m), 2.89-2.76 (1H, m), 2.73-2.59 (1H, m), 2.47-2.40 (2H, m), 2.28 (3H, s), 2.27-2.21 (2H, om), 2.13 (9H, 2xs), 1.59 (2H, quin, J = 7.1 Hz). |

*= no Boc protection of amine required in synthesis. Compound purified using silica gel chromatography, eluting from 2-10% (2 M NH$_3$ in MeOH) in DCM.

Example 27

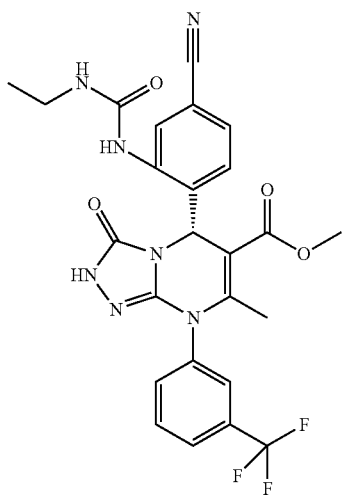 [SMILES: CCNC(=O)Nc1cc(C#N)ccc1[C@@H]1C(C(=O)OC)=C(C)N(c2cccc(C(F)(F)F)c2)c2n[nH]c(=O)n21]

(R)-5-[4-Cyano-2-(3-ethyl-ureido)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 16 (80 mg, 0.160 mmol) and DIPEA (44 mg, 0.34 mmol) were dissolved in a mixture of toluene/dioxane (1 mL: 0.5 mL) and diphenylphosphoryl azide (48 mg, 0.175 mmol) was added, and the resultant stirred mixture was warmed to 85° C. and aged for 5 minutes. The reaction mixture was cooled slightly and ethylamine (2 M in MeOH; 0.24 mL, 0.48 mmol) was added and the resulting mixture was allowed to cool to RT and stirred for a further 1 h. The reaction was partitioned between EtOAc and aqueous sodium bicarbonate and the organic layer was separated, washed twice with water, dried (Na$_2$SO$_4$), filtered and concentrated in vacuo. This resultant residue was purified by chromatography, eluting from 60-75% EtOAc in DCM and afforded the title compound as a cream solid (26 mg).

LC-MS (Method 3): Rt=4.15 min, m/z=542.0 [M+H]+

$^1$H NMR (400 MHz, d$_6$-DMSO) δ 11.36 (1H, bs), 8.39 (1H, bs), 8.17-8.11 (2H, m), 7.97-7.88 (2H, m), 7.81 (1H, t, J=7.9 Hz), 7.64-7.55 (1H, m), 7.45 (1H, dd, J=8.1, 1.7 Hz), 7.03 (1H, t, J=5.3 Hz), 6.16 (1H, d, J=0.9 Hz), 3.39 (3H, s), 3.22-3.13 (2H, m), 2.18 (3H, d, J=0.8 Hz), 1.11 (3H, t, J=7.2 Hz).

The following examples were prepared from Intermediate 16 and the appropriately substituted amines using an analogous method to Example 27:

| Ex | Structure | LC-MS (Method 3) | NMR |
|---|---|---|---|
| 28* | 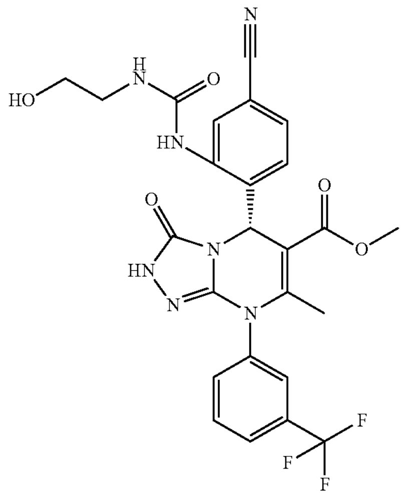 [SMILES: COC(=O)C1=C(C)N(c2cccc(C(F)(F)F)c2)c2n[nH]c(=O)n2[C@@H]1c1ccc(C#N)cc1NC(=O)NCCO] | Rt = 3.80 min, m/z = 558.2 [M + H]⁺ | ¹H NMR (400 MHz, d₆-DMSO) δ 11.32 (1H, bs), 8.54 (1H, bs), 8.23-8.19 (1H, m), 8.15 (1H, bs), 7.98-7.87 (2H, m), 7.86-6.77 (1H, m), 7.63-7.54 (1H, m), 7.43 (1H, dd, J = 8.1, 1.7 Hz), 7.12 (1H, t, J = 4.8 Hz), 6.21 (1H, d, J = 0.7 Hz), 4.78 (1H, t, J = 5.2 Hz), 3.54-3.47 (2H, m), 3.40 (3H, s), 3.30-3.22 (1H, m), 3.22-3.13 (1H, m), 2.17 (3H, d, J = 0.8 Hz). |
| 29 | 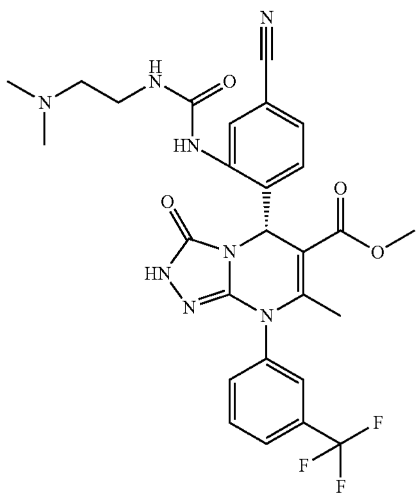 | Rt = 3.29 min, m/z = 585.1 [M + H]⁺ | ¹H NMR (400 MHz, d₆-DMSO) δ 11.32 (1H, bs), 8.57 (1H, bs), 8.24-8.19 (1H, m), 8.15 (1H, bs), 7.98-7.87 (2H, m), 7.81 (1H, t, J = 7.9 Hz), 7.63-7.54 (1H, m), 7.42 (1H, dd, J = 8.0, 1.8 Hz), 7.05 (1H, t, J = 5.1 Hz), 6.22 (1H, m), 3.39 (3H, s), 3.29-3.16 (2H, om), 2.43-2.34 (2H, m), 2.21 (6H, s), 2.17 (3H, s). |

*= Purified by MDAP.

Example 30

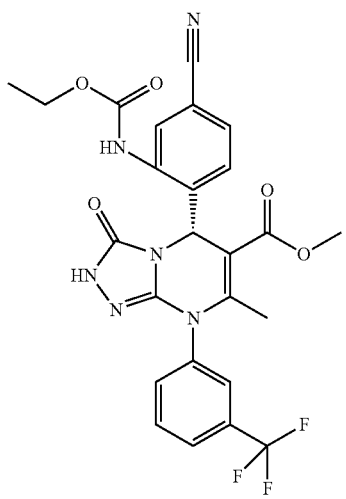 [SMILES: CCOC(=O)Nc1cc(C#N)ccc1[C@@H]1C(C(=O)OC)=C(C)N(c2cccc(C(F)(F)F)c2)c2n[nH]c(=O)n21]

(R)-5-(4-Cyano-2-ethoxycarbonylamino-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 16 (50 mg, 0.100 mmol), DIPEA (28.4 mg, 0.22 mmol) and ethanol (18 mg, 0.39 mmol) were dissolved in toluene and diphenylphosphoryl azide (30 mg, 0.109 mmol) was added. The resulting solution was stirred at RT for 5 mins prior to warming to 85° C. for 1 h. The reaction was partitioned between EtOAc and aqueous sodium bicarbonate and the organic layer was separated, washed twice with water, dried (Na₂SO₄), filtered and concentrated in vacuo. This resultant residue was purified by chromatography, eluting from 20-25% EtOAc in DCM and afforded the title compound as a cream solid (13 mg).

LC-MS (Method 3): Rt=4.60 min, m/z=543.1 [M+H]⁺

¹H NMR (400 MHz, d₆-DMSO) δ 11.52 (1H, bs), 9.26 (1H, m), 8.11 (1H, bs), 7.99-7.95 (1H, m), 7.94-7.87 (2H, m), 7.81 (1H, t, J=7.9 Hz), 7.77-7.72 (1H, m), 7.64 (1H, dd, J=8.1, 1.7 Hz), 6.18 (1H, m), 4.23-4.12 (2H, m), 3.40 (3H, s), 2.20 (3H, d, J=0.8 Hz), 1.26 (3H, t, J=7.2 Hz).

The following example was prepared from Intermediate 16 and 2-dimethylamino-ethanol using an analogous method to Example 30:

| Ex | Structure | LC-MS (Method 3) | NMR |
|---|---|---|---|
| 31* | 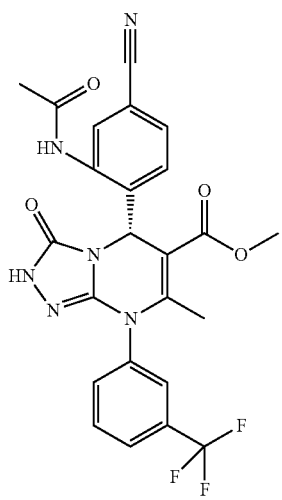 | Rt = 3.40 min, m/z = 586.2 [M + H]+ | $^1$H NMR (400 MHz, $d_6$-DMSO) δ 11.53 (1H, bs), 9.27 (1H, bs), 8.16 (1H, s, formate), 8.11 (1H, bs), 7.98 (1H, d, J = 1.7 Hz), 7.95-7.88 (2H, m), 7.81 (1H, t, J = 7.8 Hz), 7.77-7.72 (1H, m), 7.64 (1H, dd, J = 8.1, 1.7 Hz), 6.19 (1H, d, J = 0.8 Hz), 4.29-4.15 (2H, m), 3.40 (3H, s), 3.56 (2H, t, J = 5.8 Hz), 2.22 (6H, s), 2.21 (3H, d, J = 0.8 Hz). |

*= Dioxane was added to RXN mixture to aid solubility of reagents. Compound was purified by MDAP.

Example 32

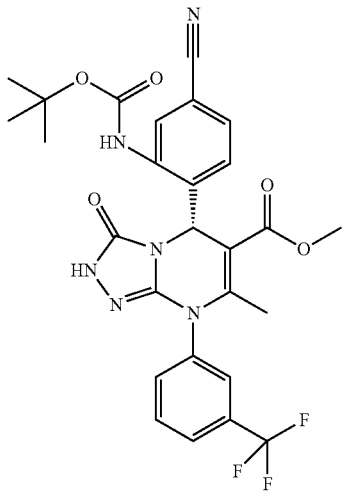 [SMILES: COC(=O)C1=C(C)N(c2cccc(C(F)(F)F)c2)c2n[nH]c(=O)n2[C@@H]1c1ccc(C#N)cc1NC(=O)OC(C)(C)C]

(R)-5-(2-Acetylamino-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 20

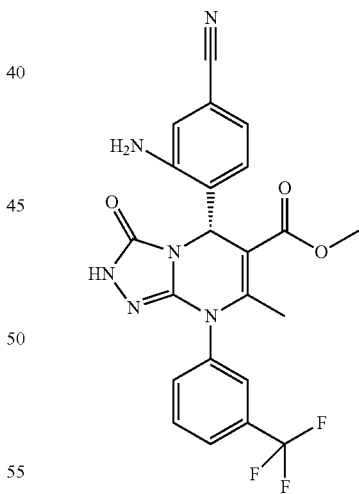

(R)-5-(2-tert-Butoxycarbonylamino-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester The title compound was prepared from Intermediate 16 (300 mg, 0.601 mmol) and 2-methyl-propan-2-ol (2.5 mL) using an analogous method to Example 30 from Intermediate 16 and gave the product as an amber gum (111 mg).

LC-MS (Method 1): Rt=3.72 min, m/z=571.0 [M+H]+

Intermediate 21

(R)-5-(2-Amino-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester The title compound was prepared from Intermediate 20 (105 mg, 0.184 mmol) using an analogous method to that used in the final stage of the synthesis of Example 22, and afforded the product as a beige solid (60 mg).

LC-MS (Method 3): Rt=4.25 min, m/z=471.0 [M+H]+

(R)-5-(2-Acetylamino-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester Example 32

Intermediate 21 (15 mg, 0.032 mmol) and DIPEA (28 µL, 0.16 mmol) were dissolved in 1,2-dichloroethane (0.5 mL) and acetyl chloride (7 µL, 0.096 mmol) was added. The resulting solution was stirred at 50° C. for 1½ h then a crystal of 4-dimethylamino-pyridine and further acetyl chloride (7 µL, 0.096 mmol) were added and the heating continued for 30 mins at 50° C. The resulting solution was treated with $K_2CO_3$ (40 mg, 0.29 mmol), MeOH (1 mL) and water (5 drops) and stirred at RT for 1½ h. The reaction was partitioned between DCM and water and the organic layer was separated, washed with water, dried ($Na_2SO_4$), filtered and concentrated in vacuo. This resultant residue was purified by chromatography, eluting from 50-75% EtOAc in DCM and afforded the title compound as a cream solid (13 mg).

LC-MS (Method 3): Rt=4.09 min, m/z=513.1 [M+H]$^+$ $^1$H NMR (400 MHz, d$_6$-DMSO) δ 11.51 (1H, bs), 9.89 (1H, bs), 8.12 (1H, s), 8.04-8.01 (1H, m), 7.94-7.88 (2H, m), 7.84-7.78 (1H, m), 7.77-7.71 (1H, m), 7.65-7.59 (1H, m), 6.30 (1H, s), 3.37 (3H, s), 2.21 (3H, d, J=0.8 Hz), 2.20 (3H, os).

Examples 33a/33b

33a

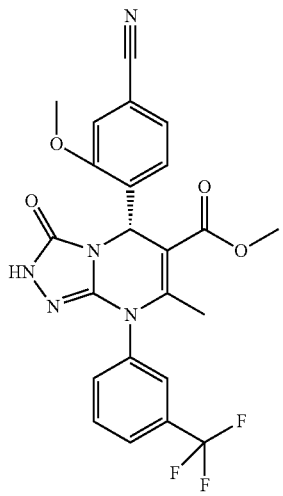 [SMILES: COC(=O)C1=C(C)N(c2cccc(C(F)(F)F)c2)c2n[nH]c(=O)n2[C@@H]1c1ccc(C#N)cc1N]

33b

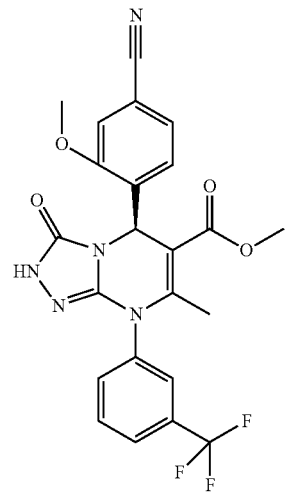

(R) and (S)-5-(2-Acetylamino-4-cyano-phenyl)-7-methyl-3-oxo-8-(3-trifluoro methyl-phenyl)-2,3,5,8-tetrahydro-[1,2,4]triazolo[4,3-a]pyrimidine-6-carboxylic acid methyl ester Intermediate 22

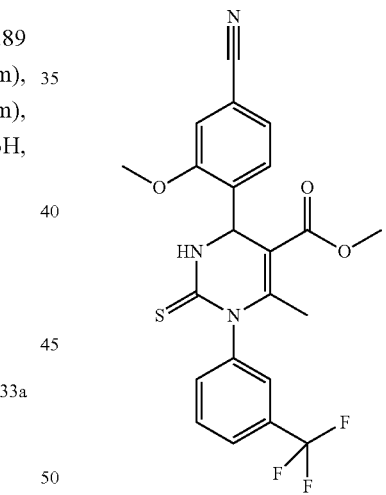

4-(4-Cyano-2-methoxy-phenyl)-6-methyl-2-thioxo-1-(3-trifluoromethyl-phenyl)-1,2,3,4-tetrahydro-pyrimidine-5-carboxylic acid methyl ester A stirred solution in DME (65 mL) of 4-formyl-3-methoxy-benzonitrile (3.22 g, 19.98 mmol), 3-trifluoromethylphenyl thiourea (4.40 g, 19.98 mol) and trimethylsilyl-polyphosphoric acid (6.50 g, 2 wt equiv.) was treated with methyl acetoacetate (2.53 g, 2.35 mL, 21.78 mmol). The resulting mixture was warmed to 70° C. for 18 h and the reaction was concentrated in vacuo to give a yellow/orange foam, which was partitioned between EtOAc and water. The aqueous extract was further extracted with EtOAc (×2) and the combined organic extract was washed with water and brine, then dried (Na$_2$SO$_4$), filtered and concentrated in vacuo to give the title compound as an orange foam (9.79 g).

LCMS (Method 1): Rt 3.69 min, m/z 461.9 [M+H]$^+$

(R) and (S)-5-(2-Acetylamino-4-cyano-phenyl)-7-methyl-3-oxo-8-(3-trifluoro methyl-phenyl)-2,3,5,8-tetrahydro-[1,2,4]triazolo[4,3-a]pyrimidine-6-carboxylic acid methyl ester (Examples 33a/33b)

The racemic mixture of Examples 33a and 33b was prepared from Intermediate 22 (5.60 g, 12.14 mmol) using an analogous method to that employed for Intermediate 7 from Intermediate 6. Following isolation of the racemic mixture of Examples 33a and 33b (2.88 g), the title compounds were obtained by purification using chiral SFC chromatography on a chiral YMC Amylose C column (5 μM; 21.2×250 mm), eluting with MeOH/CO$_2$ [30:70] at 100 mL/min (40° C./40 psi).

Example 33a

SFC R$_t$=1.24 min

LC-MS (Method 3): Rt=4.36 min, m/z=486.2 [M+H]$^+$ $^1$H NMR (400 MHz, d$_6$-DMSO) δ 11.09 (1H, s), 7.94 (1H, bs), 7.93-7.87 (1H, m), 7.85-7.78 (2H, m), 7.55 (1H, d, J=6.7 Hz), 7.54 (1H, s), 7.42 (1H, dd, J=7.8, 1.6 Hz), 6.04 (1H, d, J=0.9 Hz), 3.84 (3H, s), 3.53 (3H, s), 2.10 (3H, d, J=0.9 Hz).

Example 33b

SFC R$_t$=2.75 min

LC-MS (Method 3): Rt=4.36 min, m/z=486.2 [M+H]$^+$ $^1$H NMR (400 MHz, d$_6$-DMSO) δ 11.09 (1H, s), 7.94 (1H, bs), 7.93-7.87 (1H, m), 7.85-7.78 (2H, m), 7.55 (1H, d, J=6.7 Hz), 7.54 (1H, s), 7.42 (1H, dd, J=7.8, 1.6 Hz), 6.04 (1H, d, J=0.9 Hz), 3.84 (3H, s), 3.53 (3H, s), 2.10 (3H, d, J=0.9 Hz).

Examples 34a/34b

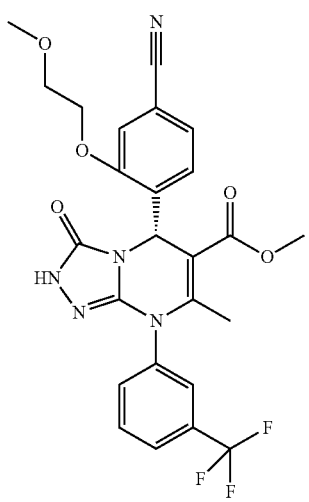

34a

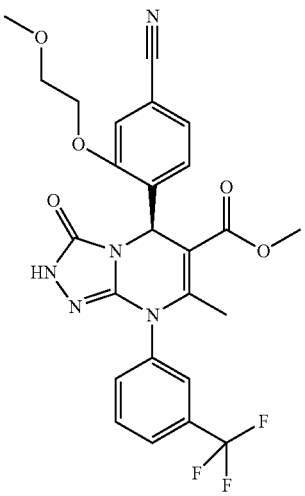

34b

(R) and (S)-5-[4-Cyano-2-(2-methoxy-ethoxy)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

Intermediate 23

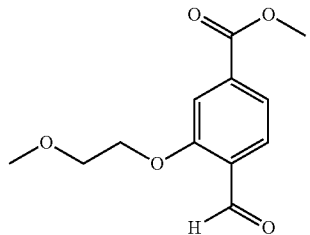

4-Formyl-3-(2-methoxy-ethoxy)-benzoic acid methyl ester

A mixture of 4-formyl-3-hydroxy-benzoic acid methyl ester (1.80 g, 9.99 mmol) and K$_2$CO$_3$ (2.76 g, 19.97 mmol) in DMF (20 mL) was treated with 1-bromo-2-methoxy-ethane (1.20 mL, 12.77 mmol) and heated to 75° C. for 18 h under nitrogen. The reaction mixture was concentrated in vacuo and partitioned between EtOAc and water. The aqueous extract was further extracted with EtOAc (×2) and the combined organic extract was washed with water and brine, then dried (Na$_2$SO$_4$), filtered and concentrated in vacuo to give the title compound as an dark brown waxy solid (1.88 g).

$^1$H NMR (400 MHz, CDCl$_3$) δ 10.56 (1H, d, J=0.5 Hz), 7.88 (1H, dd, J=7.8, 0.5 Hz), 7.70-7.69 (1H, m), 7.68 (1H, s), 4.39-4.28 (2H, m), 3.95 (3H, s), 3.85-4.81 (2H, m), 3.4 (3H, s).

Intermediate 24

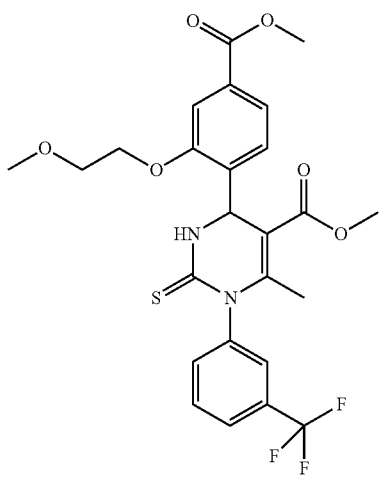

4-[4-Methoxycarbonyl-2-(2-methoxy-ethoxy)-phenyl]-6-methyl-2-thioxo-1-(3-trifluoromethyl-phenyl)-1,2,3,4-tetrahydro-pyrimidine-5-carboxylic acid methyl ester Intermediate 24 was prepared from Intermediate 23 (1.88 g, 7.89 mmol) using an analogous method to that employed for Intermediate 22, and gave the desired product as a yellow glass (2.57 g).
LC-MS (Method 1): Rt=3.86 min, m/z=539.0 [M+H]$^+$

Intermediate 25

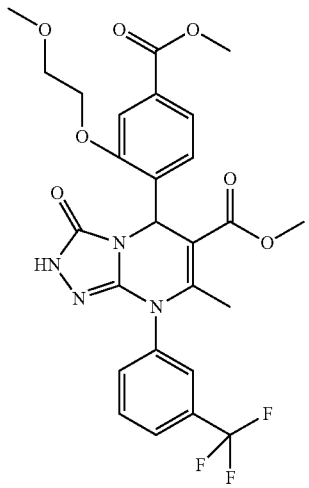

5-[4-Methoxycarbonyl-2-(2-methoxy-ethoxy)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 25 was prepared from Intermediate 24 (2.56 g, 4.75 mmol) using an analogous method to that employed to prepare Intermediate 7 from Intermediate 6, and afforded the desired product as a white solid (1.20 g).
LC-MS (Method 1): Rt=3.29 min, m/z=563.0 [M+H]$^+$

Intermediate 26

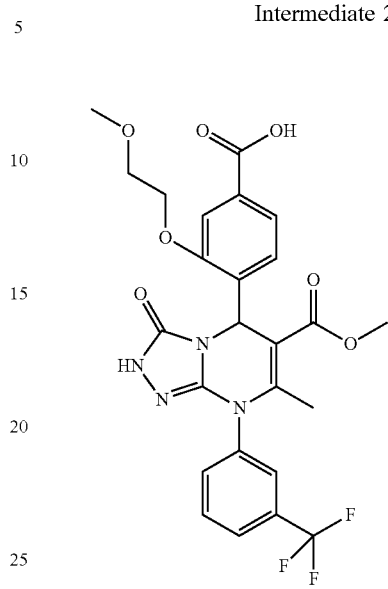

5-[4-Carbamoyl-2-(2-methoxy-ethoxy)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester A solution of Intermediate 25 (1.20 g, 2.13 mmol) in dioxane (15 mL) was treated with aqueous 1 M NaOH (4.8 mL) and the resulting solution was stirred for 18 h at RT. The reaction was diluted with EtOAc (100 mL) and water (100 mL) and aqueous 1 M HCl (5.0 mL) was added to ensure acidity. The organic phase was washed with brine, dried (Na$_2$SO$_4$) and concentrated in vacuo. The resultant residue was triturated with DCM to give the title compound as a white solid (0.91 g).
LC-MS (Method 1): Rt=2.97 min, m/z=547.1 [M−H]

Intermediate 27

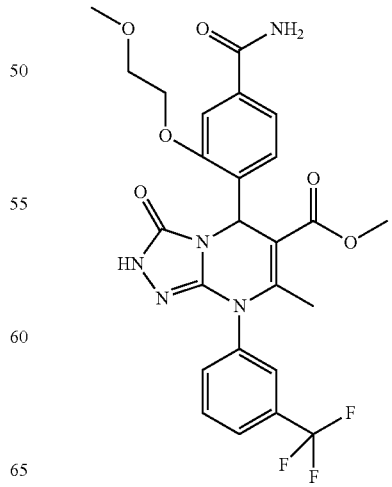

5-[4-Carbamoyl-2-(2-methoxy-ethoxy)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester Intermediate 27 was prepared from Intermediate 26 (0.80 g, 1.46 mmol) and ammonium chloride (0.32 g, 5.98 mmol) using an analogous method to that employed in the final stage of the preparation of Example 13 from Intermediate 16. The desired product was obtained as an off white gum (0.38 g).

LC-MS (Method 4): Rt=2.97 min, m/z=548.2 [M+H]$^+$ (R) and (S)-5-[4-Cyano-2-(2-methoxy-ethoxy)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester (Examples 34a/34b)

An ice cold solution of Intermediate 27 (450 mg, 0.82 mmol) in DMF (2 mL) was treated with cyanuric chloride (227 mg, 1.23 mmol) and the resulting solution was stirred for 1½ h at RT. The reaction mixture was cooled using an ice/water bath and a solution of $K_2CO_3$ (380 mg, 2.75 mmol) in a mixture of acetone/water (2 mL: 2 mL) was added. The cooling bath was removed and further quantity of water (15 mL) was added and the resulting mixture allowed to stir at RT for 18 h. The reaction was diluted with water and EtOAc (×3) and the combined organic phase was washed with water and brine, then dried ($Na_2SO_4$), filtered and concentrated in vacuo. This resultant residue was purified by chromatography, eluting from 0-10% MeOH in DCM and afforded the racemate of Example 33 as a white solid (230 mg).

Following isolation of the racemic mixture of Examples 34a and 34b, the title compounds were obtained by purification using chiral chromatography with a ChiralPak IA column (5 μM; 20×250 mm), eluting with a mixture of 20% ethanol/30% n-heptane/50% DCM (isocratic), running at 18 mL/min and measuring absorbance at 254 nm.

Example 34a

Chiral chromatograpghy R$_t$=3.8 min
LC-MS (Method 3): Rt=4.50 min, m/z=530.2 [M+H]$^+$
$^1$H NMR (400 MHz, d$_6$-DMSO) δ 11.07 (1H, s), 8.04 (1H, s), 7.92-7.83 (2H, m), 7.83-7.68 (1H, m), 7.57-7.52 (2H, m), 7.40 (1H, dd, J=7.8, 1.5 Hz), 6.06 (1H, d, J=0.9 Hz), 4.36-4.28 (1H, m), 4.27-4.18 (1H, m), 3.69-3.57 (2H, m), 3.50 (3H, s), 3.26 (3H, s), 2.08 (3H, d, J=0.9 Hz).

Example 34b

Chiral chromatography R$_t$=9.2 min
LC-MS (Method 3): Rt=4.50 min, m/z=530.2 [M+H]$^+$
$^1$H NMR (400 MHz, d$_6$-DMSO) δ $^1$H NMR (400 MHz, d6-DMSO) δ 11.07 (1H, s), 8.04 (1H, s), 7.92-7.83 (2H, m), 7.83-7.68 (1H, m), 7.57-7.52 (2H, m), 7.40 (1H, dd, J=7.8, 1.5 Hz), 6.06 (1H, d, J=0.9 Hz), 4.36-4.28 (1H, m), 4.27-4.18 (1H, m), 3.69-3.57 (2H, m), 3.50 (3H, s), 3.26 (3H, s), 2.08 (3H, d, J=0.9 Hz).

Examples 35a/35b

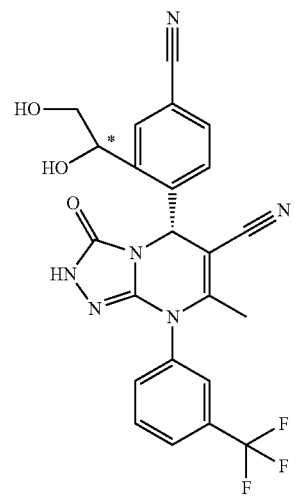

Diastereoisomer 1

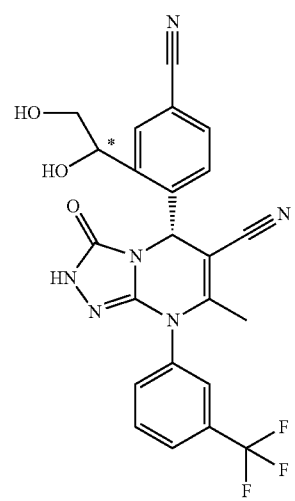

Diastereoisomer 2

(R)-5-[4-Cyano-2-(1,2-dihydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carbonitrile (diastereoisomers 35a and 35b)

Intermediate 28

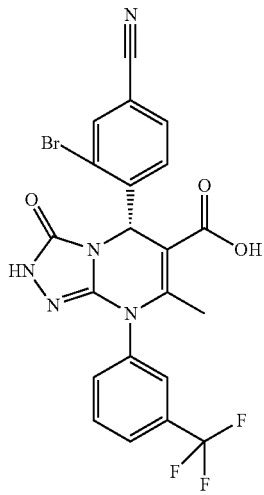 [SMILES: CC1=C(C(=O)O)[C@@H](c2ccc(C#N)cc2Br)n2c(n[nH]c2=O)N1c1cccc(C(F)(F)F)c1]

(S)-5-(2-Bromo-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid A cooled (−50° C.), stirred solution of Intermediate 7 (10.70 g, 20.04 mmol) in DCM (200 mL) was treated drop-wise with BBr$_3$ (1 M solution DCM; 100 mL, 0.10 mol) at such a rate as to moderate an exotherm observed. The resulting solution was allowed to warm to 0° C. over 1 h then to RT over a further 1½ h. The reaction mixture was cooled to 0° C. and carefully quenched via addition of water (25 mL). The DCM layer was separated and the aqueous layer extracted with DCM (×2). The combined organic extract was washed with water and brine, then dried (Na$_2$SO$_4$), filtered and concentrated in vacuo. This residue was purified by chromatography, eluting from 0-10% MeOH in DCM and afforded the semi-pure product as a pale orange solid (9.42 g). This material was dissolved in EtOAc and the organic phase was extracted with saturated aqueous NaHCO$_3$ (×3). The combined aqueous extract was carefully acidified with concentrated aqueous hydrochloric acid and the resulting precipitate was collected by filtration and dried in vacuo to give the title compound as a white solid (3.38 g).

LC-MS (Method 1): Rt=2.97 min, m/z=520.1 [M($^{79}$Br)+H]$^+$

Intermediate 29

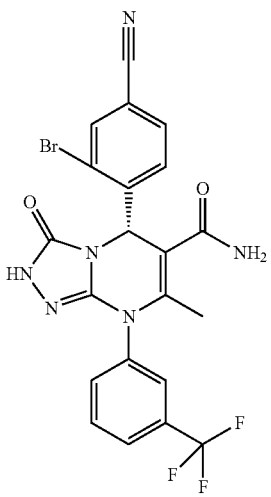 [SMILES: CC1=C(C(N)=O)[C@@H](c2ccc(C#N)cc2Br)n2c(n[nH]c2=O)N1c1cccc(C(F)(F)F)c1]

(S)-5-(2-Bromo-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid amide Intermediate 29 was prepared from Intermediate 28 (3.90 g, 7.50 mmol) and ammonium chloride (1.62 g, 30.0 mmol) using an analogous method to that employed in the final stage of the preparation of Example 13 from Intermediate 16. The title compound was afforded as a pale yellow solid (2.87 g).

LC-MS (Method 4): Rt=2.83 min, m/z=519.2 [M($^{79}$Br)+H]$^+$

Intermediate 30

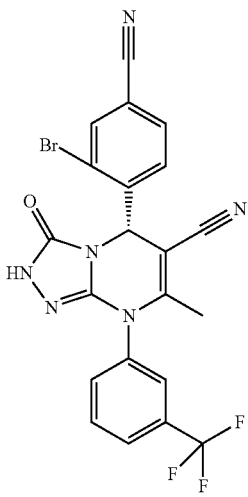 [SMILES: CC1=C(C#N)[C@@H](c2ccc(C#N)cc2Br)n2c(n[nH]c2=O)N1c1cccc(C(F)(F)F)c1]

(S)-5-(2-Bromo-4-cyano-phenyl)-7-methyl-3-oxo-8-(3-trifluoromethyl-phenyl)-2,3,5,8-tetrahydro-[1,2,4]triazolo[4,3-a]pyrimidine-6-carbonitrile A solution of Intermediate 29 (2.87 g, 5.53 mmol) in THF (100 mL) was treated with Burgess reagent (1-methoxy-N-triethylammoniosulfonyl-methanimidate), (3.94 g, 16.55 mmol) and the resulting solution was stirred at RT for 2 h. The reaction mixture was diluted with water and EtOAc (×3)

and the combined organic phase was washed with water and brine, then dried (Na$_2$SO$_4$), filtered and concentrated in vacuo. This resultant residue was purified by chromatography, eluting from 0-50% EtOAc in DCM and afforded the title compound as a white solid (2 g).

LC-MS (Method 4): Rt=2.83 min, m/z=519.2 [M($^{79}$Br)+H]$^+$ (R)-5-[4-Cyano-2-(1,2-dihydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carbonitrile (Examples 35a/35b)

The title compounds were prepared from Intermediate 30 (1.0 g, 2.0 mmol) using similar procedures to those used to prepare Examples 1a/1b from Intermediate 7. Purification by chromatography, eluting from 0-5% MeOH in EtOAc, afforded the title compounds as a white solids 35a (150 mg) and 35b (20 mg) as a white solids.

Example 35a

Diastereoisomer 1

LC-MS (Method 3): Rt=3.73 min, m/z=483.0 [M+H]$^+$
$^1$H NMR (400 MHz, d$_6$-DMSO) δ 11.20 (1H, s), 8.05 (1H, bs), 7.92-7.90 (1H, m), 7.90-7.86 (2H, m), 7.82-7.77 (1H, m), 7.76 (1H, dd, J=8.1, 1.8 Hz), 7.61 (1H, d, J=8.1 Hz), 6.16 (1H, m), 5.33 (1H, d, J=4.4 Hz), 5.14-5.05 (1H, m), 4.57 (1H, t, J=5.8 Hz), 3.94-3.84 (1H, m), 3.59-3.49 (1H, m), 1.84 (3H, d, J=1.2 Hz).

Example 35b

Diastereoisomer 2

LC-MS (Method 3): Rt=3.77 min, m/z=481.3 [M+H]$^+$
$^1$H NMR (400 MHz, d$_6$-DMSO) δ 11.13 (1H, s), 8.05 (1H, bs), 7.92-7.90 (1H, m), 7.90-7.86 (2H, m), 7.82-7.77 (1H, m), 7.76 (1H, dd, J=8.1, 1.8 Hz), 7.71 (1H, d, J=8.1 Hz), 6.14 (1H, m), 5.31-5.27 (2H, m), 4.55 (1H, t, J=5.7 Hz), 3.68-3.59 (1H, m), 3.58-3.49 (1H, m), 1.99 (3H, d, J=1.2 Hz).

Example 36

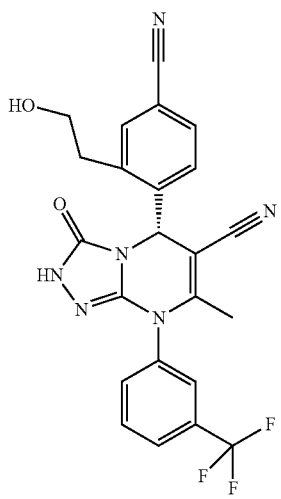 [SMILES: CC1=C(C#N)[C@@H](c2ccc(C#N)cc2CCO)n2c(n[nH]c2=O)N1c1cccc(C(F)(F)F)c1]

(R)-5-[4-Cyano-2-(2-hydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carbonitrile The title compound was prepared from Intermediate 30 (0.95 g, 1.895 mmol) using similar procedures to those used to prepare Intermediate 13 from Intermediate 7. Following this procedure afforded the tittle compound as a colorless glass (60 mg).

LC-MS (Method 3): Rt=3.98 min, m/z=467.0 [M+H]$^+$
$^1$H NMR (400 MHz, d$_6$-DMSO) δ 11.39 (1H, s), 8.32-8.03 (1H, v. bs), 7.95-7.85 (2H, m), 7.84-7.79 (1H, m), 7.78 (1H, s), 7.77 (1H, dd, J=7.8, 1.7 Hz), 7.73-7.64 (1H, m), 6.05 (1H, s), 4.83 (1H, bs), 3.82-3.61 (2H, m), 3.19-2.94 (2H, m), 1.94 (3H, d, J=1.1 Hz).

Example 37

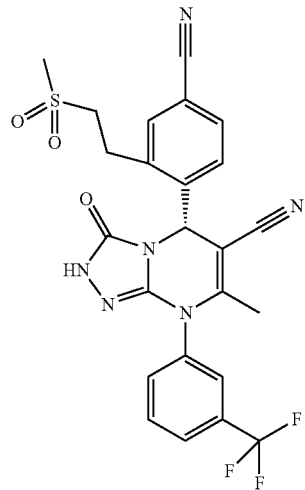 [SMILES: CC1=C(C#N)[C@@H](c2ccc(C#N)cc2CCS(C)(=O)=O)n2c(n[nH]c2=O)N1c1cccc(C(F)(F)F)c1]

(R)-5-[4-Cyano-2-(2-methanesulfonyl-ethyl)-phenyl]-7-methyl-3-oxo-8-(3-trifluoromethyl-phenyl)-2,3,5,8-tetrahydro-[1,2,4]triazolo[4,3-a]pyrimidine-6-carbonitrile Intermediate 31

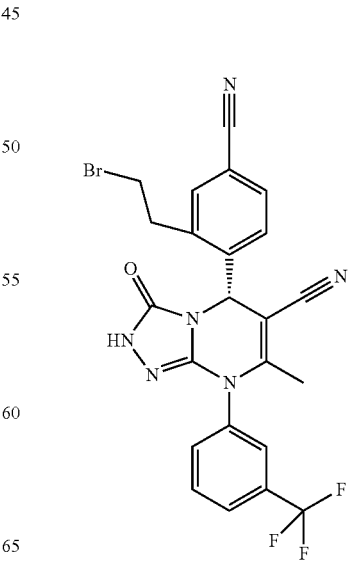

(R)-5-[2-(2-Bromo-ethyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carbonitrile The title compound was prepared from Example 36 (35 mg, 0.075 mmol) using a similar procedure to that used to prepare Intermediate 14 from Intermediate 13, and gave the desired product as a white glass (18 mg).

LC-MS (Method 1): Rt=3.41 min, m/z=528.9 [M($^{79}$Br)+H]$^+$

(R)-5-[4-Cyano-2-(2-methanesulfonyl-ethyl)-phenyl]-7-methyl-3-oxo-8-(3-trifluoromethyl-phenyl)-2,3,5,8-tetrahydro-[1,2,4]triazolo[4,3-a]pyrimidine-6-carbonitrile Example 37

A solution of Intermediate 31 (18 mg, 0.034 mmol) in DMF (0.5 mL) was treated with sodium methanesulfinate, (10 mg, 0.098 mmol) under argon and the resulting mixture was stirred at 70° C. for 3 h. The reaction was concentrated in vacuo and the residue was partitioned between water and EtOAc (×3), and the combined organic phase was washed with water and brine, then dried (Na$_2$SO$_4$), filtered and concentrated in vacuo. This resultant residue was purified by chromatography, eluting from 0-10% MeOH in DCM and afforded the title compound as a colorless glass (14 mg).

LC-MS (Method 3): Rt=4.07 min, m/z=529.1 [M+H]$^+$ $^1$H NMR (400 MHz, d$_6$-DMSO) δ 11.40 (1H, s), 8.13 (1H, v. bs), 7.95-7.88 (2H, m), 7.87-7.68 (4H, m), 6.03 (1H, s), 3.79-3.60 (2H, m), 3.56-3.44 (2H, m), 3.07 (3H, s), 1.84 (3H, d, J=1.2 Hz).

Examples 38a/38b

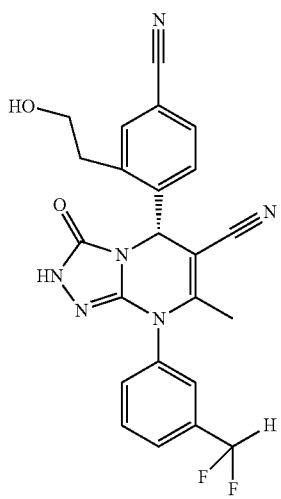

38a

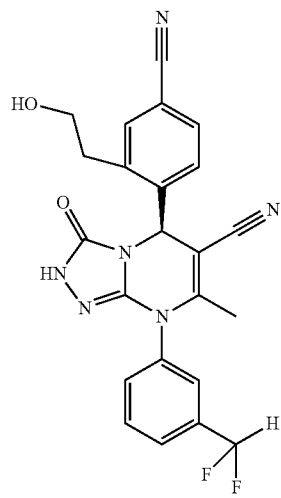

38b

(R) and (S)-5-[4-Cyano-2-(2-hydroxy-ethyl)-phenyl]-8-(3-difluoromethyl-phenyl)-7-methyl-3-oxo-2,3,5,8-tetrahydro-[1,2,4]triazolo[4,3-a]pyrimidine-6-carbonitrile Intermediate 32

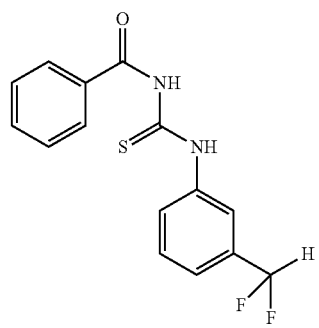 [SMILES: O=C(NC(=S)Nc1cccc(C(F)F)c1)c1ccccc1]

1-Benzoyl-3-(3-difluoromethyl-phenyl)-thiourea

A solution of benzoyl isocyanate (9.06 mL, 67.42 mmol) in acetone (45 mL) was added to a cooled (5° C.) solution in acetone (45 mL) of 3-difluoromethyl-phenylamine (9.65 g, 67.42 mmol) and the resulting solution was heated to reflux 30 mins. The reaction mixture was poured onto crushed ice (300 mL) with rapid stirring and the resulting yellow precipitate was collected by filtration and dried in vacuo to afford the title compound (>20.65 g—wet)

$^1$H NMR (400 MHz, d$_6$-DMSO) δ 12.65 (1H, bs), 11.64 (1H, bs), 8.03-7.97 (3H, m), 7.82 (1H, d, J=8.1 Hz), 7.68 (1H, dd, J=7.5, 1.2 Hz), 7.61-7.52 (3H, m), 7.48 (1H, d, J=7.6 Hz), 7.08 (1H, t, J=55.8 Hz).

Intermediate 33

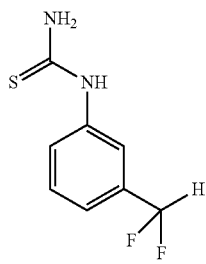 [SMILES: NC(=S)Nc1cccc(C(F)F)c1]

(3-Difluoromethyl-phenyl)-thiourea

Intermediate 32 (20.65 g, 67.4 mmol) was suspended in 1 M aqueous NaOH (135 mL, 135.0 mmol) and the resulting mixture heated to 80° C. with stirring for 1 h. The reaction mixture was cooled and the pH adjusted to pH 4 with formic acid to give a pale orange solid precipitate. The suspension was basified to pH 8 using saturated aqueous NaHCO$_3$ to give an off-white solid, which was collected by filtration. The solid was dissolved in DCM (300 mL) and the organic phase was washed with 1 M aqueous Na$_2$CO$_3$, water and brine, then dried (Na$_2$SO$_4$), filtered and concentrated in vacuo to afford the title compound as a tan colored solid (11.11 g).

LC-MS (Method 1): Rt=2.31 min, m/z=203.0 [M+H]$^+$

Intermediate 34

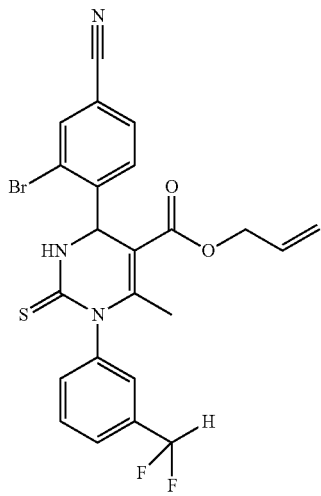 [SMILES: C=CCOC(=O)C1=C(C)N(c2cccc(C(F)F)c2)C(=S)NC1c1ccc(C#N)cc1Br]

4-(2-Bromo-4-cyano-phenyl)-1-(3-difluoromethyl-phenyl)-6-methyl-2-thioxo-1,2,3,4-tetrahydro-pyrimidine-5-carboxylic acid allyl ester The title compound was prepared from Intermediate 33, 3-bromo-4-formyl-benzonitrile and 3-oxo-butyric acid allyl ester using a similar procedure to that used to prepare Intermediate 22.

LC-MS (Method 1): Rt=3.86 min, m/z=517.9 [M($^{79}$Br)+H]$^+$

Intermediate 35

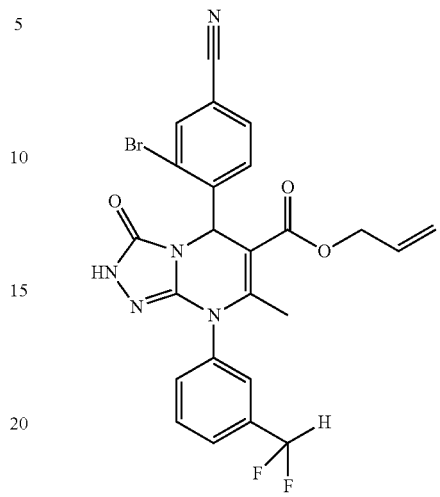

5-(2-Bromo-4-cyano-phenyl)-8-(3-difluoromethyl-phenyl)-7-methyl-3-oxo-2,3,5,8-tetrahydro-[1,2,4]triazolo[4,3-a]pyrimidine-6-carboxylic acid allyl ester The title compound was prepared from Intermediate 34 (1.94 g, 3.74 mmol) using a similar procedure to that used to prepare Intermediate 7 from Intermediate 6, and afforded the desired product as an yellow foam (1.01 g).

LC-MS (Method 1): Rt=3.39 min, m/z=541.9 [M($^{79}$Br)+H]$^+$

Intermediate 36

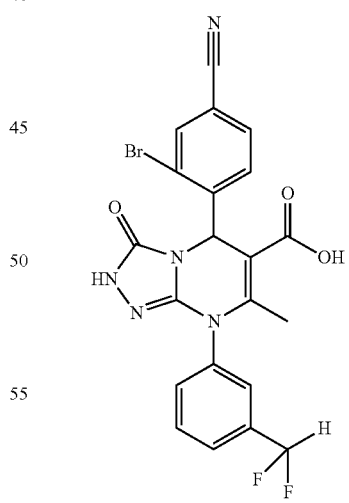

5-(2-Bromo-4-cyano-phenyl)-8-(3-difluoromethyl-phenyl)-7-methyl-3-oxo-2,3,5,8-tetrahydro-[1,2,4]triazolo[4,3-a]pyrimidine-6-carboxylic acid A solution of Intermediate 35 (814 mg, 1.50 mmol) and morpholine (0.23 mL, 2.63 mmol) in THF (15 mL) was treated with tetrakis(triphenylphosphine)palladium(0) (9 mg, 0.008 mmol) and the resulting solution was stirred at RT for 18 h under argon. Further tetrakis(triphenylphosphine)palladium(0) (2×9 mg, 2×0.008 mmol) was added and the stirring continued over 3 days. The reaction mixture was diluted with water (25 mL) and EtOAc (150 mL) and the organic phase separated and washed with 10% aqueous citric acid solution, water and brine, then dried ($Na_2SO_4$), filtered and concentrated in vacuo. This resultant residue was purified by chromatography, eluting from 0-100% EtOAc in DCM, and afforded the title compound as a white solid (104 mg).

LC-MS (Method 1): Rt=2.72 min, m/z=501.9 [M($^{79}$Br)+H]$^+$

Intermediate 37

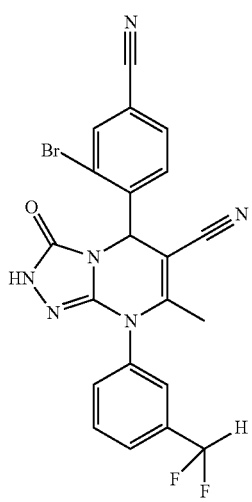

5-(2-Bromo-4-cyano-phenyl)-8-(3-difluoromethyl-phenyl)-7-methyl-3-oxo-2,3,5,8-tetrahydro-[1,2,4]triazolo[4,3-a]pyrimidine-6-carbonitrile The title compound was prepared from Intermediate 36 (100 mg, 0.20 mmol) using similar procedures to those used to prepare Intermediate 30 from Intermediate 28, and gave the product as an white foam (67 mg).

LC-MS (Method 1): Rt=3.06 min, m/z=482.9 [M($^{79}$Br)+H]$^+$ (R) and (S)-5-[4-Cyano-2-(2-hydroxy-ethyl)-phenyl]-8-(3-difluoromethyl-phenyl)-7-methyl-3-oxo-2,3,5,8-tetrahydro-[1,2,4]triazolo[4,3-a]pyrimidine-6-Carbonitrile Example 38a/38b The title compounds were prepared from Intermediate 37 (222 mg, 0.46 mmol) using similar procedures to those used to prepare Intermediate 13 from Intermediate 7. Following isolation of the racemic mixture of Examples 38a and 38b (64 mg), the title compounds were obtained following purification using chiral chromatography using a ChiralPak IA column (5 µM; 20×250 mm), eluting with 2% IPA in DCM at 18 mL/min and a wavelength of 254 nm.

Example 38a 22 mg

Chiral column R$_t$=9.50 min.
LC-MS (Method 3): Rt=3.64 min, m/z=449.2 [M+H]$^+$
$^1$H NMR (400 MHz, d$_6$-DMSO) δ 11.36 (1H, bs), 7.95-7.80 (1H, bm), 7.78 (1H, bs), 7.70-7.69 (4H, m), 7.68-7.60 (1H, m), 7.13 (1H, t, J=55.7 Hz), 6.06 (1H, s), 4.80 (1H, t, J=5.1 Hz), 3.84-3.62 (2H, m), 3.19-2.94 (2H, m), 1.93 (3H, d, J=1.1 Hz).

Example 38b 26 mg

Chiral column R$_t$=14.5 min.
LC-MS (Method 3): Rt=3.64 min, m/z=449.2 [M+H]$^+$
$^1$H NMR (400 MHz, d$_6$-DMSO) δ 11.36 (1H, bs), 7.95-7.80 (1H, bm), 7.78 (1H, bs), 7.70-7.69 (4H, m), 7.68-7.60 (1H, m), 7.13 (1H, t, J=55.7 Hz), 6.06 (1H, s), 4.80 (1H, t, J=5.1 Hz), 3.84-3.62 (2H, m), 3.19-2.94 (2H, m), 1.93 (3H, d, J=1.1 Hz).

Examples 39a/39b/39c/39d

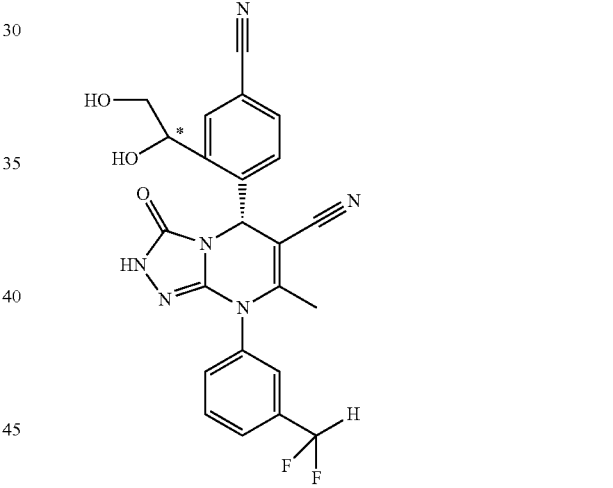

39a

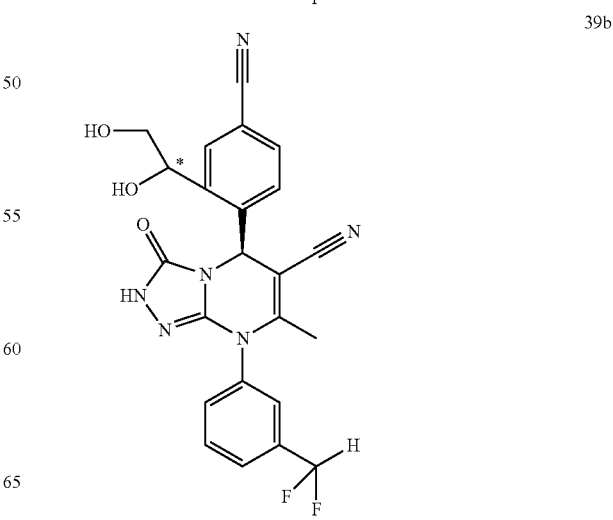

39b

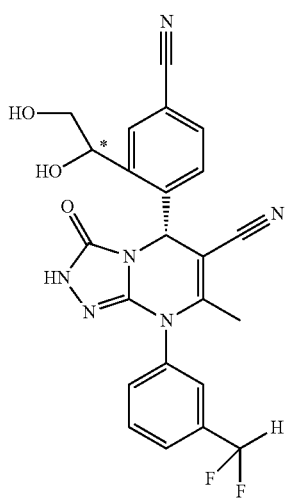

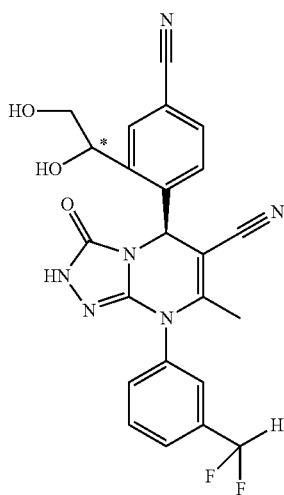

(R) and (S)-5-[4-Cyano-2-(1,2-dihydroxy-ethyl)-phenyl]-8-(3-difluoromethyl-phenyl)-7-methyl-3-oxo-2,3,5,8-tetrahydro-[1,2,4]triazolo[4,3-a]pyrimidine-6-carbonitrile The title compounds were prepared from Intermediate 37 (340 mg, 0.70 mmol) using similar procedures to those used to prepare Examples 1a and 1b from Intermediate 7. Purification by chromatography, eluting from 0-5% MeOH in EtOAc, afforded diastereosomer 1 (as a mixture of enantiomer 1 and 2) and diastereosomer 2 (as a mixture of enantiomer 1 and 2) as white solids. Following isolation of the racemate of diastereoisomer 1 and diastereoisomer 2, the pure enantiomers were obtained following purification using chiral chromatography using a ChiralPak IC column (5 μM; 20×250 mm), eluting with EtOH-n-heptane-DCM (30:45:25) DCM at 18 mL/min and a wavelength of 254 nm.

Example 39a (Diastereoisomer 1/Enantiomer 1): (13 mg)

Chiral chromatography $R_t$=11.6 min
LC-MS (Method 3): Rt=3.39 min, m/z=465.1 [M+H]$^+$
$^1$H NMR (400 MHz, d$_6$-DMSO) δ 11.41 (1H, s), 7.92 (1H, d, J=1.7 Hz), 7.87 (1H, vbs), 7.81 (1H, dd, J=8.1, 1.8 Hz), 7.78-7.68 (2H, om), 7.74 (1H, s), 7.61 (1H, d, J=8.1 Hz), 7.12 (1H, t, J=55.7 Hz), 6.13 (1H, m), 5.61 (1H, d, J=4.5 Hz), 5.21-4.98 (1H, m), 4.93-4.72 (1H, m), 4.16-4.69 (1H, m), 3.51-3.40 (1H, m), 1.92 (3H, d, J=1.1 Hz).

Example 39b (Diastereoisomer 1/Enantiomer 2): (13 mg)

Chiral chromatograpghy $R_t$=16.6 min
LC-MS (Method 3) was identical to Example 39a
$^1$H NMR (400 MHz, d$_6$-DMSO) was identical to Example 39a Example 39c (Diastereoisomer 2/Enantiomer 1): (5.5 mg Chiral chromatograpghy $R_t$=11.1 min
LC-MS (Method 3): Rt=3.47 min, m/z=465.1 [M+H]$^+$
$^1$H NMR (400 MHz, d$_6$-DMSO) δ 11.30 (1H, s), 7.93 (1H, d, J=1.8 Hz), 7.88 (1H, vbs), 7.82 (1H, dd, J=8.0, 1.7 Hz), 7.79-7.65 (4H, m), 7.12 (1H, t, J=55.6 Hz), 6.12 (1H, m), 5.61 (1H, m), 5.43-5.19 (1H, m), 4.86 (1H, t, J=5.8 Hz), 3.79-4.50 (1H, m), 3.51-3.39 (1H, m), 1.97 (3H, m).

Example 39d (Diastereoisomer 2/Enantiomer 2): (5 mg)

Chiral chromatography $R_t$=14.7 min
LC-MS (Method 3) was identical to Example 39c
$^1$H NMR (400 MHz, d$_6$-DMSO) was identical to Example 39c Biological Assay Compounds of this invention were tested for potency in a human neutrophil elastase (HNE) enzyme activity assay.

HNE Enzyme Assay

Assays were performed in 96-well plates in a total assay volume of 100 μL. The final concentration of elastase enzyme (human leukocyte elastase, Sigma E8140) was 0.00072 U/mL. The peptide substrate (MeOSuc-Ala-Ala-Pro-Val-AMC, Calbiochem #324740) was used at a final concentration of 100 μM. The final concentration of DMSO was 1% in the assay buffer (0.05M Tris.HCl, 0.1M NaCl, 0.1M CaCl$_2$, 0.0005% brij-35, pH 7.5). The enzymatic reaction was started by addition of the enzyme and incubated at 25° C. for 30 minutes. After incubation, the reaction was stopped by addition of soybean trypsin inhibitor (Sigma T9003) at a final concentration of 50 μg/well. Fluorescence was measured using a Molecular Devices fluorescence plate reader using 380 nm excitation and 460 nm emission wavelengths.

A dose response to each compound was performed and the effect of the compound in each experiment was expressed as a percentage inhibition of the control enzyme fluorescence. Dose response curves were plotted and compound potency (IC$_{50}$) was determined. Compounds were tested in at least two separate experiments.

IC$_{50}$s for tested Examples, representative of the present invention, are shown in the following table:

| Example | HNE inhibition |
|---|---|
| 1-33a, 34a, 35a, 35b, 36, 37, 38a, 39a, 39c | ++++ |
| 33b, 34b, 39d | +++ |
| 38b, 39b | ++ |

In the table above, HNE enzyme inhibition (IC$_{50}$ values) are indicated as follows: >500 nM '+'; 100-500 nM '++'; 20-100 nM '+++'; <20 nM '++++'.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

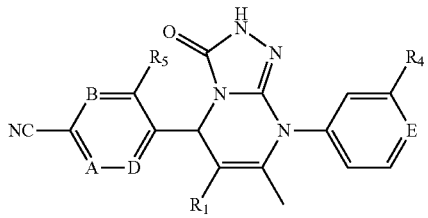

wherein
A is CH or N;
B is CH or N;
D is CH or N;
E is CH or N;
$R_1$ is —CN or a group —C(O)—V$R_2$;
V is —O—, —(CH$_2$)—, or —NH—;
$R_2$ is hydrogen or —(C$_1$-C$_6$)alkyl, optionally substituted with one or more substituents selected from the group consisting of halogen, O$R_3$, and —N$R_3R_7$;
$R_3$ is hydrogen or optionally substituted (C$_1$-C$_6$)alkyl;
$R_4$ is —CF$_3$ or —CHF$_2$,
$R_5$ is a group selected from the group consisting of:

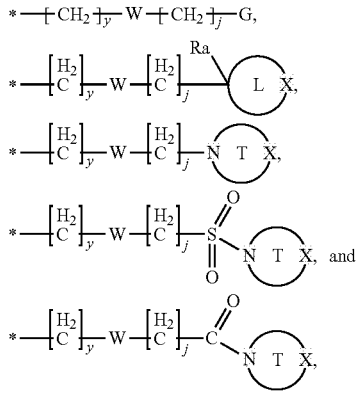

j is 0 or an integer of from 1 to 4;
y is 0 or an integer of from 1 to 4;
L and T are independently a 4 to 8-membered heterocyloalkyl ring bringing an —X— group in any of the free positions;
X is —O—, —S—, —S(O$_2$)—, or —N$R_6$;
W is —N($R_3$)—, —O—, —C(O)—, —OC(O)N($R_3$)—, —N($R_3$)C(O)N($R_3$)—, —C(O)N($R_3$)—, —N$R_3$C(O)—, —SO$_2$—, —SO$_2$N($R_3$)—, —N$R_3$S(O$_2$)—, —S—, —C(O)O—, —OC(O)—, optionally substituted (C$_1$-C$_6$)alkylene, optionally substituted (C$_3$-C$_6$)cycloalkylene, or optionally substituted (C$_4$-C$_7$)heterocycloalkylene;
G is hydrogen, halogen, —CN, —N($R_3$)($R_7$), —O$R_3$, —OC(O)O$R_3$, —OC(O)N$R_3R_7$, —N($R_3$)C(N)N($R_3$)($R_7$), —N($R_3$)C(O)N($R_3$)($R_7$), —C(O)N($R_3$)($R^7$), —N($R_3$)C(O)$R_7$, —S(O$_2$)$R_3$, —S(O$_2$)N($R_3$)($R_7$), —N($R_3$)S(O$_2$)($R_7$), —S$R_3$, —C(O)O$R_3$, —OC(O)$R_3$, optionally substituted (C$_1$-C$_6$)alkyl, optionally substituted (C$_3$-C$_6$)cycloalkyl, or optionally mono- or bi-substituted (C$_4$-C$_7$)heterocycloalkyl;
Ra is hydrogen, —OH, —NH$_2$, or optionally substituted (C$_1$-C$_6$)alkyl;
$R_6$ is hydrogen, —S(O$_2$)$R_7$, —CO$_2R_7$, —CON$R_3R_7$, —SO$_2$N$R_3R_7$, or optionally substituted (C$_1$-C$_6$)alkyl;
$R_7$ is hydrogen or optionally substituted (C$_1$-C$_6$)alkyl;
wherein, unless otherwise specified, optionally substituted means optionally substituted by one or more substituents selected from the group consisting of (C$_1$-C$_6$)alkyl, (C$_1$-C$_6$)alkoxy, (C$_1$-C$_6$)hydroxyalkyl, —OH, —NH$_2$, halogen, —CF$_3$, —OCF$_3$, and —N$R_3R_7$;
or a pharmaceutically acceptable salt thereof,
with the provisos that:
(1) when y is an integer ranging from 1 to 4, W is —O— and j is 0, then G is not hydrogen or (C$_1$-C$_6$)alkyl optionally substituted by one or more (C$_1$-C$_6$)alkoxy;
(2) when y is an integer ranging from 1 to 4, W is —N($R_3$)—, $R_3$ is hydrogen or (C$_1$-C$_6$)alkyl and j is 0, then G is not hydrogen or (C$_1$-C$_6$)alkyl;
(3) when y is 0, W is —C(O)N($R_3$)—, $R_3$ is hydrogen or (C$_1$-C$_6$)alkyl and j is 0, then G is not H or (C$_1$-C$_6$)alkyl optionally substituted with —N$R_3R_7$, wherein $R_3$ and $R_7$ are independently H or (C$_1$-C$_6$)alkyl;
(4) when y is 0, W is —S(O$_2$)— and j is 0, then G is not (C$_1$-C$_6$)alkyl optionally substituted with —OH;
(5) when y is 0, W is —S(O$_2$)N($R_3$)—, $R_3$ is H and j is 0, then G is not hydrogen; and
(6) when y is 0, W is —S(O$_2$)N($R_3$)—, $R_3$ is H or (C$_1$-C$_4$)alkyl and j is 0, then G is not hydrogen or (C$_1$-C$_6$)alkyl.

2. A compound or pharmaceutically acceptable salt according to claim 1, wherein $R_5$ is a group

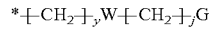

wherein W is —C(O)—, —OC(O)N($R_3$)—, —N($R_3$)C(O)N($R_3$)—, —N$R_3$C(O)—, —N$R_3$S(O$_2$)—, —S—, —C(O)O—, —OC(O)—, optionally substituted (C$_1$-C$_6$)alkylene, optionally substituted (C$_3$-C$_6$)cycloalkylene, or optionally substituted (C$_4$-C$_7$)heterocycloalkylene.

3. A compound or pharmaceutically acceptable salt according to claim 1, wherein $R_5$ is a group

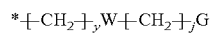

wherein y is 2, W is —N$R_3$S(O$_2$), $R_3$ is hydrogen or optionally substituted (C$_1$-C$_6$)alkyl, j is 1, and G is hydrogen.

4. A compound or pharmaceutically acceptable salt according to claim 1, wherein $R_5$ is a group

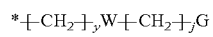

wherein y is 2 or 3, W is —S—, j is 0, and G is optionally substituted (C$_1$-C$_6$)alkyl.

5. A compound or pharmaceutically acceptable salt according to claim 1, wherein $R_5$ is a group $$*\text{-}\!\!\left[\text{CH}_2\right]_y\!\!\text{-}W\text{-}\!\!\left[\text{CH}_2\right]_j\!\!\text{-}G$$

wherein y is 2 or 3, W is —$SO_2$—, j is 0, and G is optionally substituted ($C_1$-$C_6$)alkyl.

6. A compound or pharmaceutically acceptable salt according to claim 1, wherein $R_5$ is a group $$*\text{-}\!\!\left[\text{CH}_2\right]_y\!\!\text{-}W\text{-}\!\!\left[\text{CH}_2\right]_j\!\!\text{-}G$$

wherein y is 2 or 3, W is —$NR_3C(O)$—, $R_3$ is hydrogen or optionally substituted ($C_1$-$C_6$)alkyl, j is 1, and G is hydrogen.

7. A compound or pharmaceutically acceptable salt according to claim 1, wherein $R_4$ is —$CF_3$.

8. A compound or pharmaceutically acceptable salt according to claim 1, wherein $R_4$ is —$CHF_2$.

9. A compound or pharmaceutically acceptable salt according to claim 1, wherein $R_1$ is —CN or a group —C(O)—$VR_2$; V is —O—; $R_2$ is —($C_1$-$C_6$)alkyl optionally substituted with one or more substituents selected from the group consisting of halogen, $OR_3$, and —$NR_3R_7$.

10. A compound or pharmaceutically acceptable salt according to claim 1, wherein $R_5$ is a group selected from the group consisting of

[chemical structures]

wherein Ra is hydrogen, —OH, —$NH_2$, or optionally substituted ($C_1$-$C_6$)alkyl; L and T are each independently a 4 to 8-membered heterocycloalkyl ring bringing an —X— group in any of the free positions; X is —O—, —S—, —$S(O_2)$—, or —$NR_6$—; $R_6$ is hydrogen, —$SO_2R_7$, —$CO_2R_7$, —$CONR_3R_7$, —$SO_2NR_3R_7$, or optionally substituted ($C_1$-$C_6$)alkyl; $R_3$ and $R_7$ are each independently hydrogen or optionally substituted ($C_1$-$C_6$)alkyl.

11. A compound or pharmaceutically acceptable salt according to claim 1, which is a compound of formula (I)′ and has the absolute configuration of carbon (1) shown below:

(I)″

[chemical structure]

12. A compound or pharmaceutically acceptable salt according to claim 1, which is in the form of a pharmaceutically acceptable salt.

13. A pharmaceutical composition, comprising a compound or pharmaceutically acceptable salt according to claim 1 and a pharmaceutically acceptable carrier or excipient.

14. A pharmaceutical composition according to claim 13, which is in a form suitable for oral administration or administration by the pulmonary route.

15. A method of treating a disease or condition selected from the group consisting of chronic obstructive pulmonary disease, bronchiectasis, chronic bronchitis, lung fibrosis, pneumonia, acute respiratory distress syndrome, pulmonary emphysema, smoking-induced emphysema, cystic fibrosis, and asthma, comprising administering, to a subject in need thereof, an effective amount of a compound or pharmaceutically acceptable salt according to claim 1.

16. A pressurized metered dose inhaler, which contains a compound or pharmaceutically acceptable salt according to claim 1.

17. A dry powder inhaler, which contains a compound or pharmaceutically acceptable salt according to claim 1.

18. A method according to claim 15, wherein said disease or condition is chronic obstructive pulmonary disease.

19. A method according to claim 15, wherein said disease or condition is bronchiectasis.

20. A method according to claim 15, wherein said disease or condition is chronic bronchitis.

21. A method according to claim 15, wherein said disease or condition is lung fibrosis.

22. A method according to claim 15, wherein said disease or condition is pneumonia.

23. A method according to claim 15, wherein said disease or condition is acute respiratory distress syndrome.

24. A method according to claim 15, wherein said disease or condition is pulmonary emphysema.

25. A method according to claim 15, wherein said disease or condition is smoking-induced emphysema.

26. A method according to claim 15, wherein said disease or condition is cystic fibrosis.

27. A method according to claim 15, wherein said disease or condition is asthma.

* * * * *